US007816324B2

(12) United States Patent
Ahn et al.

(10) Patent No.: US 7,816,324 B2
(45) Date of Patent: Oct. 19, 2010

(54) COMPOSITION AND METHOD FOR THE TREATMENT OF DISEASES AFFECTED BY A PEPTIDE RECEPTOR

(75) Inventors: Jung-Mo Ahn, Richardson, TX (US); Martin Beinborn, Newton, MA (US)

(73) Assignee: Board of Regents, The University of Texas System, Austin, TX (US)

( * ) Notice: Subject to any disclaimer, the term of this patent is extended or adjusted under 35 U.S.C. 154(b) by 54 days.

(21) Appl. No.: 12/048,199

(22) Filed: Mar. 13, 2008

(65) Prior Publication Data
US 2008/0300193 A1 Dec. 4, 2008

Related U.S. Application Data

(60) Provisional application No. 60/894,580, filed on Mar. 13, 2007.

(51) Int. Cl.
*A61K 38/26* (2006.01)
*A61K 38/10* (2006.01)
(52) U.S. Cl. .............................. 514/14; 514/2; 530/308
(58) Field of Classification Search ........................ None
See application file for complete search history.

(56) References Cited

U.S. PATENT DOCUMENTS

| 5,212,203 | A | 5/1993 | Shroot et al. | |
|---|---|---|---|---|
| 5,929,114 | A | 7/1999 | Domagala et al. | |
| 2005/0261346 | A1* | 11/2005 | Zhu et al. | 514/332 |

OTHER PUBLICATIONS

Ahn, J.-M., et al., "A new approach to search for the bioactive conformation of glucagon: positional cyclization scanning." J. Med. Chem. (2001), 44:3109-3116.
Ahn, J.-M., et al., "Development of potent truncated glucagon antagonists." J. Med. Chem. (2001), 44:1372-1379.
Ahn, J.-M., et al., "Peptidomimetics and peptide backbone modifications." Mini-Reviews in Medicinal Chemistry (2002), 2:463-473.
Bulotta, et al., "ACultured pancreatic ductal cells undergo cell cycle re-distribution and beta-cell-like differentiation in response to glucagon-like peptide-1." J. Mol. Endocrinol. (2002), 29:347-360.
Burgess, K., et al., "Solid-phase syntheses of β-turn analogues to mimic or disrupt protein-protein interactions". Acc. Chem. Res. (2001), 34:826-835.
Cavaghan, M. K., et al., "Interactions between insulin resistance and insulin secretion in the development of glucose intolerance." J. Clin. Invest. (2000), 106:329-333.
Chang, L. L., et al., "Substituted imidazoles as glucagon receptor antagonists." Bioorg. Med. Chem. Lett. (2001), 11:2549-2553.
Chapuis, H. P., et al., "Shorter puromycin analog synthesis by means of an efficient Staudinger-Vilarrasa coupling." Tetrahedron (2006), 62:12108-12115.
Chen, D., et al., "A nonpeptidic agonist of glucagon-like peptide 1 receptors with efficacy in diabetic db/db mice." Proc. Natl. Acad. Sci. U.S.A. (2007), 104:943-948.

Defronzo, R. A., et al., "Effects of exenatide (exendin-4) on glycemic control and weight over 30 weeks in metformin-treated patients with type 2 diabetes." Diabetes Care (2005), 28:1092-1100.
Drucker, D. J. et al., "The incretin system: glucagon-like peptide-1 receptor agonists and dipeptidyl peptidase-4 inhibitors in type 2 diabetes." Lancet (2006), 368:1696-1705.
Edwards, C. M. B., et al., "Exendin-4 reduces fasting and postprandial glucose and decreases energy intake in healthy volunteers." Am. J. Physiol. Endocrinol. Metab. (2001), 281:E155-E161.
Egan, J. M., et al., "GLP-1 receptor agonists are growth and differentiation factors for pancreatic islet beta cells." Diabetes/Metab. Res. Rev. (2003), 19:115-123.
Elbronds, B., et al., "Pharmacokinetics, pharmacodynamics, safety, and tolerability of a single-dose of NN2211, a long-acting glucagon-like peptide 1 derivative, in healthy male subjects." Diabetes Care (2002), 25:1398-1404.
Ernst, J. T., et al., "Design and application of an α-helixmimetic scaffold based on an oligoamide-foldamer strategy: antagonism of the Bak BH-3/BcI-xL complex." Angew. Chem. Int. Ed. (2003), 42:535-539.
Hoare, S. R. J., et al., "Mechanisms of peptide and nonpeptide ligand binding to class B G-proteincoupled receptors." Drug Discovery Today (2005), 10:417-427.
Hruby, V. J., et al., "Design in topographical space of peptide and peptidomimetic ligands that affect behavior a chemist's glimpse at the mind-body problem." Acc. Chem. Res. (2001), 34:389-397.
Jacoby, E., et al., "Biphenyls as potential mimetics of protein α-helix." Bioorg. Med. Chem. Lett. (2002), 12:891-893.
Knudsen, L. B., et al., "Glucagon-like peptide-1: the basis of a new class of treatment for type 2 diabetes." J. Med. Chem. (2004), 47:4128-4134.
Knudsen, L. B., et al., "Small-molecule agonists for the glucagon-like peptide 1 receptor." Proc. Natl. Acad. Sci. U.S.A. (2007), 104:937-942.
Kolterman, O. G., et al., "Synthetic exendin-4 (exenatide) significantly reduces postprandial and fasting plasma glucose in subjects with type 2 diabetes." J. Clin. Endocrinol. Metab. (2003), 88:3082-3089.
Ling, A., et al., "Identification of alkylidene hydrazides as glucagon receptor antagonists." J. Med. Chem. (2001), 44:3141-3149.
Madsen, P., et al., "Optimization of alkylidene hydrazide based human glucagon receptor antagonists. Discovery of the highly potent and orally available 3-cyano-4-hydroxybenzoic acid [1-(2,3,5,6-tetramethylbenzyl)-1H-indol-4-ylmethylene]hydrazide." J. Med. Chem. (2002), 45:5755-5775.

(Continued)

*Primary Examiner*—Christina Bradley
(74) *Attorney, Agent, or Firm*—Chainey P. Singleton; Edwin S. Flores; Chalker Flores, LLP

(57) ABSTRACT

The present invention includes peptidomimetic compound compositions and methods of making and using peptidomimetic compounds to modulate the activity of a peptide receptor for the treatment of one or more of hyperglycemia, insulin resistance, hyperinsulinemia, obesity, hyperlipidemia, hyperlipoproteinemia or other symptoms that relate to the function of the targeted receptor. The peptidomimetic includes an oligo-benzamide compound having at least three optionally substituted benzamides.

6 Claims, 82 Drawing Sheets

OTHER PUBLICATIONS

Mahato, R. I., et al., "Emerging trends in oral delivery of peptide and protein drugs." Critical Reviews in Therapeutic Drug Carrier Systems (2003), 20:153-214.

Murphy, K. G.; "Nonpeptidic glucagon-like peptide 1 receptor agonists: A magic bullet for diabetes?" Proc. Natl. Acad. Sci. U.S.A. (2007), 104:689-690.

Neidigh, J. W., et al., "Exendin-4 and glucagon-likepeptide-1: NMR structural comparisons in the solution and micelle-associated states." Biochemistry (2001), 40:13188-13200.

Oguri, H., et al., "Design and synthesis of a trans-fused polycyclic ether skeleton as an a-helix mimetic scaffold." Tetrahedron Lett. (2005), 46:2179-2183.

Orner, B. P., et al., "Toward proteomimetics: Terphenyl derivatives as structural and functional mimics of extended regions of an α-helix." J. Am. Chem. Soc. (2001), 123:5382-5383.

Peczuh, M. W., et al., "Peptide and protein recognition by designed molecules." Chem. Rev. (2000), 100:2479-2494.

Perry, T. A..,et al., "The glucagon-like peptides: a double-edged therapeutic sword?" Trends Pharmacol. Sci. (2003), 24:377-383.

Rickard, D. J., et al., "Intermittent treatment with parathyroid hormone (PTH) as well as a non-peptide small molecule agonist of the PTH1 receptor inhibits adipocyte differentiation in human bone marrow stromal cells." Bone (2006), 39:1361-1372.

Runge, S., et al., "Different domains of the glucagon and glucagon-like peptide-1 receptors provide the critical determinants of ligand selectivity." Br. J. Pharmacol. (2003), 138:787-794.

Souers, A. J., et al., "β-Turn mimetic library synthesis: scaffolds and applications." Tetrahedron (2001), 57:7431-7448.

Stoffers, D. A., et al., "Insulinotropic glucagon-like peptide 1 agonists stimulate expression of homeodomain protein IDX-1 and increase islet size in mouse pancreas." Diabetes (2000), 49:741-748.

Tibaduiza, E. C., et al., "A small molecule ligand of the glucagon-like peptide 1 receptor targets its amino-terminal hormone binding domain." J. Biol. Chem. (2001), 276:37787-37793.

Toft-Nielsen, M. B., et al., "Determinants of the effectiveness of glucagon-like peptide-1 in type 2 diabetes." J. Clin. Endocrinol. Metab. (2001), 86:3853-3860.

Vilsboll, T., et al., "No reactive hypoglycaemia in type 2 diabetic patients after subcutaneous administration of GLP-1 and intravenous glucose." Diabetic Med. (2001), 18:144-149.

Zander, M., et al., "Effect of 6-week course of glucagon-like peptide 1 on glycaemic control, insulin sensitivity, and beta-cell fuction in type 2 diabetes: a parallel-group study." Lancet (2002), 359:824-830.

Zhang, B. B., et al., "New approaches in the treatment of type 2 diabetes." Curr. Opin. Chem. Biol. (2000), 4:461-467.

International Search Report and Written Opinion for PCT/US2008/056920 dated Aug. 1, 2008.

International Search Report and Written Opinion for PCT/US2008/056918 dated Sep. 10, 2008.

Ahn, et al., "Facile synthesis of benzamides to mimic an alpha helix," Tetrahedron Letters (2007), 48:3543-3547.

Konig, et al., "Solid-Phase Synthesis of Oligo(p-benzamide) Foldamers," Organnic Letters (2006), 8:1819-1822.

Konig, et al., "Supramolecular PEG-co-Oligo(p-benzamide)s Prepared on a Peptide Synthezier, " J Am Chem Soc (2007), published on Web Dec. 23, 2006, 129:704-708.

Tanatani, et al., "Helical Structures of N-Alkylated Poly(p-benzamide)s," J Am Chem Soc (2005), 127:8553-8561.

* cited by examiner

His⁷-Ala-Glu-Gly¹⁰-Thr-Phe-Thr-Ser-Asp¹⁵-Val-Ser-Ser-Tyr-Leu²⁰-Glu-Gly-Gln-Ala-Ala²⁵-Lys-Glu-Phe-Ile-Ala³⁰-Trp-Leu-Val-Lys-Gly-Arg³⁶-NH₂

FIG. 14

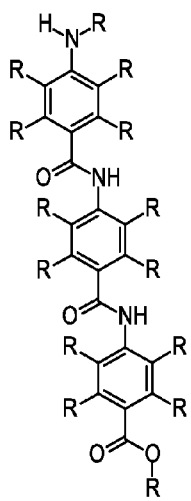 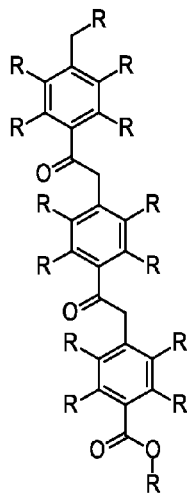 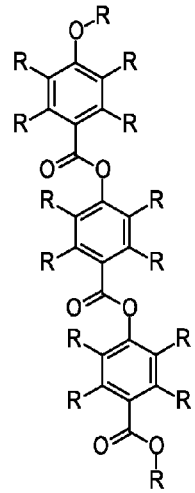 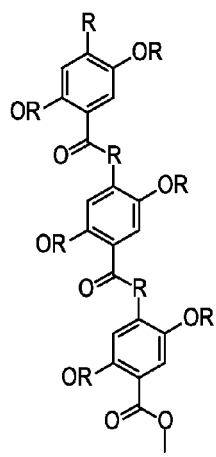
FIG. 16A  FIG. 16B  FIG. 16C  FIG. 16D
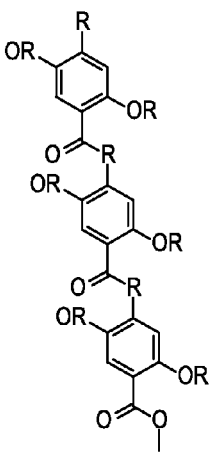 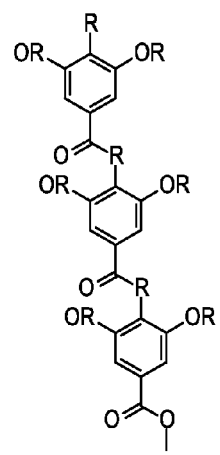 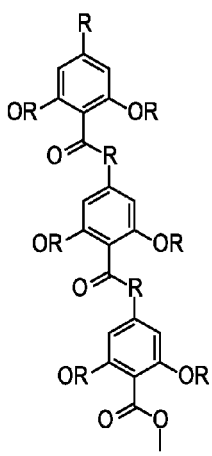
FIG. 16E  FIG. 16F  FIG. 16G
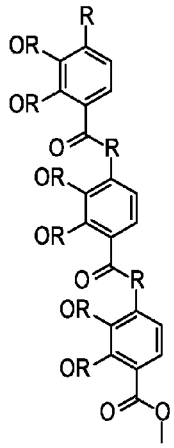 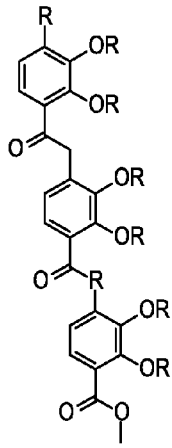 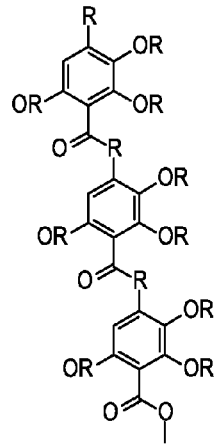 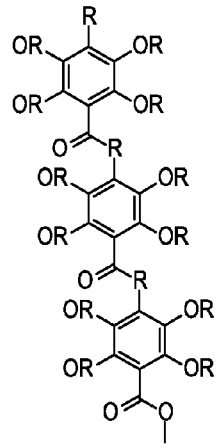
FIG. 16H  FIG. 16I  FIG. 16J  FIG. 16K

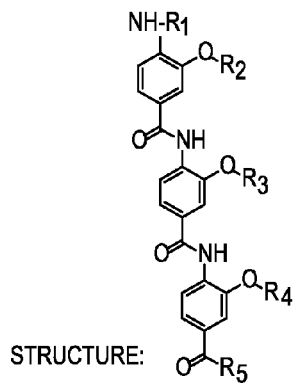

STRUCTURE:

| COMPOUND NUMBER | R1 | R2 | R3 | R4 | R5 |
|---|---|---|---|---|---|
| 101 | Ac | benzyl | isopropyl | 4-F-benzyl | OMe |
| 102 | Ac | phenethyl | isopropyl | 4-F-benzyl | OMe |
| 103 | Ac | pentafluorobenzyl | isopropyl | 4-F-benzyl | OMe |
| 104 | Ac | 4-F-benzyl | isopropyl | 4-F-benzyl | OMe |
| 105 | Ac | 4-OH-phenethyl | isopropyl | 4-F-benzyl | OMe |
| 106 | Ac | 2-naphthylmethyl | isopropyl | 4-F-benzyl | OMe |
| 107 | Ac | 1-naphthylmethyl | isopropyl | 4-F-benzyl | OMe |
| 108 | Ac | 3-thienylethyl | isopropyl | 4-F-benzyl | OMe |
| 109 | Ac | imidazolylethyl | isopropyl | 4-F-benzyl | OMe |
| 110 | Ac | benzyl | -CH$_3$ | 4-F-benzyl | OMe |
| 111 | Ac | benzyl | sec-butyl | 4-F-benzyl | OMe |

FIG. 18A-1

| | | | | | |
|---|---|---|---|---|---|
| 112 | Ac | benzyl | n-butyl | 4-F-benzyl | OMe |
| 113 | Ac | benzyl | isobutyl | 4-F-benzyl | OMe |
| 114 | Ac | benzyl | cyclohexylmethyl | 4-F-benzyl | OMe |
| 115 | Ac | benzyl | cyclopropylmethyl | 4-F-benzyl | OMe |
| 116 | Ac | benzyl | 4-F-benzyl | 4-F-benzyl | OMe |
| 117 | Ac | benzyl | benzyl | benzyl | OMe |
| 118 | Ac | benzyl | isobutyl | benzyl | OMe |
| 119 | Ac | benzyl | isopropyl | pentafluorobenzyl | OMe |
| 120 | Ac | benzyl | isobutyl | 4-OH-phenethyl | OMe |
| 121 | Ac | benzyl | isobutyl | 2-naphthylmethyl | OMe |
| 122 | Ac | benzyl | isobutyl | 1-naphthylmethyl | OMe |
| 123 | Ac | benzyl | isobutyl | 3-thienylmethyl | OMe |
| 124 | Ac | benzyl | isobutyl | imidazolylmethyl | OMe |
| 125 | Ac | imidazolylethyl | imidazolylethyl | imidazolylethyl | OMe |
| 126 | Ac | imidazolylethyl | isobutyl | 4-OH-phenethyl | OMe |
| 127 | Ac | imidazolylethyl | isobutyl | 4-OH-phenethyl | OMe |
| 128 | Ac | benzyl | phenethyl | phenethyl | OMe |
| 129 | Ac | benzyl | pentafluorobenzyl | pentafluorobenzyl | OMe |
| 130 | Ac | -CH₃ | -CH₃ | -CH₃ | OMe |

FIG. 18A-2

| | | | | | |
|---|---|---|---|---|---|
| 131 | Ac | isobutyl | isobutyl | isobutyl | OMe |
| 132 | Ac | isobutyl | isobutyl | isobutyl | OMe |
| 133 | Ac | n-butyl | n-butyl | n-butyl | OMe |
| 134 | Ac | ~~OH | ~~OH | ~~OH | OMe |
| 135 | Ac | ~~OH | ~~OH | ~~(CH2)2COOH | OMe |
| 136 | Ac | ~~(CH2)2COOH | ~~(CH2)2NH2 | ~~(CH2)2COOH | OMe |
| 137 | Ac | ~~(CH2)2NH2 | ~~(CH2)2COOH | ~~(CH2)2NH2 | OMe |
| 138 | Ac | ~~CH(OH)CH3 | ~~(CH2)2COOH | ~~(CH2)2NH2 | OMe |
| 139 | Ac | ~~CH2OH | ~~(CH2)2COOH | ~~(CH2)3NHC(NH)NH2 | OMe |
| 140 | Ac | ~~(CH2)2COOH | ~~(CH2)3NHC(NH)NH2 | ~~(CH2)2COOH | OMe |
| 141 | Ac | ~~(CH2)3NHC(NH)NH2 | ~~(CH2)3NHC(NH)NH2 | ~~(CH2)3NHC(NH)NH2 | OMe |
| 142 | Ac | ~~CH2-imidazole | ~~CH2Ph | ~~(CH2)2COOH | OMe |
| 143 | Ac | ~~CH2Ph | ~~(CH2)2COOH | ~~CH2-(4-F-Ph) | OMe |
| 144 | Ac | ~~CH2Ph | ~~(CH2)2COOH | ~~CH2-(4-OH-Ph) | OMe |
| 145 | Ac | –CH3 | ~~CH2Ph | ~~CH2-naphthyl | OMe |
| 146 | Ac | –CH3 | ~~CH2CH2Ph | ~~CH2-naphthyl | OMe |
| 147 | Ac | –CH3 | ~~CH2-(4-F-Ph) | ~~CH2-naphthyl | OMe |
| 148 | Ac | –CH3 | ~~CH2-naphthyl | ~~CH2-naphthyl | OMe |
| 149 | Ac | –CH3 | ~~CH2-naphthyl | ~~CH2-naphthyl | OMe |
| 150 | Ac | –CH3 | ~~CH2-(pentafluorophenyl) | ~~CH2-naphthyl | OMe |

FIG. 18A-3

| | | | | | |
|---|---|---|---|---|---|
| 152 | Ac | §–CH₃ | 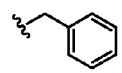 | 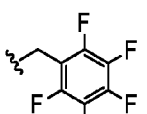 | OMe |
| 153 | Ac | §–CH₃ | 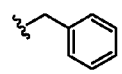 | 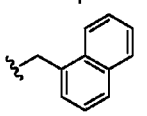 | OMe |
| 154 | Ac | §–CH₃ | 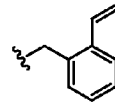 | 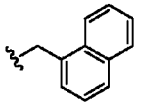 | OMe |
| 155 | Ac | §–CH₃ | 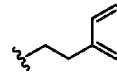 | 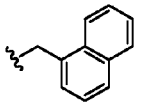 | OMe |
| 156 | Ac | §–CH₃ | 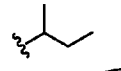 | 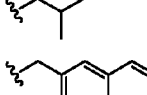 | OMe |
| 157 | Ac | §–CH₃ | 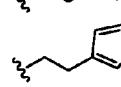 | 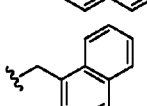 | OMe |
| 158 | Ac | §–CH₃ | 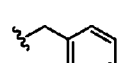 | 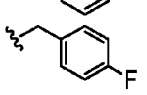 | OMe |
| 159 | Ac | 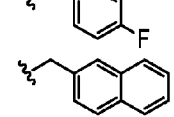 | 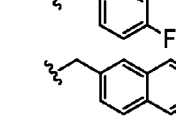 | 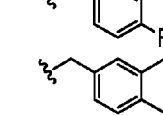 | OMe |
| 160 | Ac | 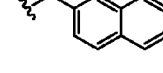 | 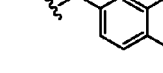 | 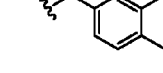 | OMe |
FIG. 18A-4

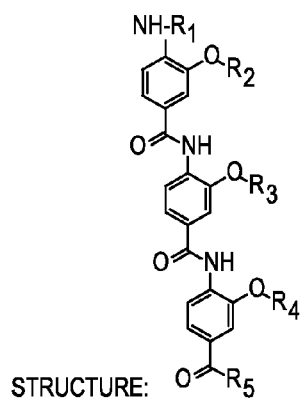

STRUCTURE:

| COMPOUND NUMBER | R1 | R2 | R3 | R4 | R5 |
|---|---|---|---|---|---|
| 161 | His-Gly | benzyl | isopropyl | 4-fluorobenzyl | OMe |
| 162 | His-Gly | phenethyl | isopropyl | 4-fluorobenzyl | OMe |
| 163 | His-Gly | pentafluorobenzyl | isopropyl | 4-fluorobenzyl | OMe |
| 164 | His-Gly | 4-fluorobenzyl | isopropyl | 4-fluorobenzyl | OMe |
| 165 | His-Gly | 4-hydroxyphenethyl | isopropyl | 4-fluorobenzyl | OMe |
| 166 | His-Gly | 2-naphthylmethyl | isopropyl | 4-fluorobenzyl | OMe |
| 167 | His-Gly | 1-naphthylmethyl | isopropyl | 4-fluorobenzyl | OMe |
| 168 | His-Gly | thienylethyl | isopropyl | 4-fluorobenzyl | OMe |
| 169 | His-Gly | imidazolylethyl | isopropyl | 4-fluorobenzyl | OMe |
| 170 | His-Gly | benzyl | —CH$_3$ | 4-fluorobenzyl | OMe |
| 171 | His-Gly | benzyl | sec-butyl | 4-fluorobenzyl | OMe |
| 172 | His-Gly | benzyl | n-butyl | 4-fluorobenzyl | OMe |

FIG. 18B-1

| | | | | | |
|---|---|---|---|---|---|
| 190 | His-Gly | -CH₃ | -CH₃ | -CH₃ | OMe |
| 191 | His-Gly | isobutyl | isobutyl | isobutyl | OMe |
| 192 | His-Gly | sec-butyl | sec-butyl | sec-butyl | OMe |
| 193 | His-Gly | n-butyl | n-butyl | n-butyl | OMe |
| 194 | His-Gly | CH₂CH₂OH | CH₂CH₂OH | CH₂CH₂OH | OMe |
| 195 | His-Gly | CH₂CH₂OH | CH₂CH₂OH | (CH₂)₃COOH | OMe |
| 196 | His-Gly | (CH₂)₃COOH | (CH₂)₄NH₂ | (CH₂)₃COOH | OMe |
| 197 | His-Gly | (CH₂)₄NH₂ | (CH₂)₃COOH | (CH₂)₄NH₂ | OMe |
| 198 | His-Gly | CH₂CH(OH)CH₃ | (CH₂)₃COOH | (CH₂)₄NH₂ | OMe |
| 199 | His-Gly | CH₂CH₂OH | (CH₂)₃COOH | (CH₂)₃NHC(=NH)NH₂ | OMe |
| 200 | His-Gly | (CH₂)₃COOH | (CH₂)₃NHC(=NH)NH₂ | (CH₂)₃COOH | OMe |
| 201 | His-Gly | (CH₂)₃NHC(=NH)NH₂ | (CH₂)₃NHC(=NH)NH₂ | (CH₂)₃NHC(=NH)NH₂ | OMe |
| 202 | His-Gly | CH₂-imidazole | CH₂CH₂-Ph | (CH₂)₃COOH | OMe |
| 203 | His-Gly | CH₂-Ph | (CH₂)₃COOH | CH₂-Ph(4-F) | OMe |
| 204 | His-Gly | CH₂-Ph | (CH₂)₃COOH | CH₂CH₂-Ph(4-OH) | OMe |
| 205 | His-Gly | -CH₃ | CH₂-Ph | CH₂-naphthyl | OMe |
| 206 | His-Gly | -CH₃ | CH₂CH₂-Ph | CH₂-naphthyl | OMe |
| 207 | His-Gly | -CH₃ | CH₂-Ph(4-F) | CH₂-naphthyl | OMe |
| 208 | His-Gly | -CH₃ | CH₂-naphthyl | CH₂-naphthyl | OMe |

FIG. 18B-3

| | | | | | |
|---|---|---|---|---|---|
| 209 | His-Gly | ξ-CH₃ | 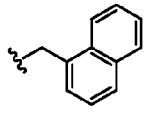 | 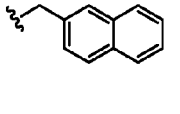 | OMe |
| 210 | His-Gly | ξ-CH₃ | 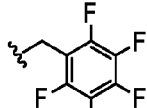 | 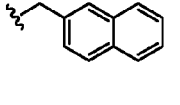 | OMe |
| 212 | His-Gly | ξ-CH₃ | 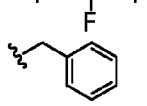 | 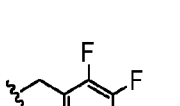 | OMe |
| 213 | His-Gly | ξ-CH₃ | 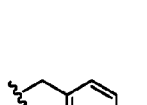 | 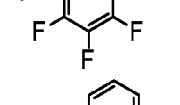 | OMe |
| 214 | His-Gly | ξ-CH₃ | 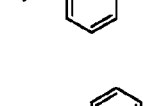 | 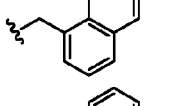 | OMe |
| 215 | His-Gly | ξ-CH₃ | 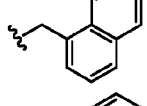 | 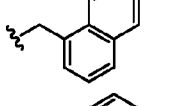 | OMe |
| 216 | His-Gly | ξ-CH₃ | 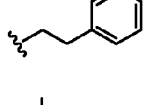 | 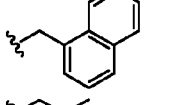 | OMe |
| 217 | His-Gly | ξ-CH₃ | 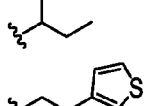 | 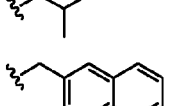 | OMe |
| 218 | His-Gly | ξ-CH₃ | 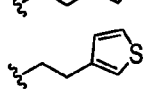 | 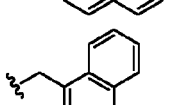 | OMe |
| 219 | His-Gly | 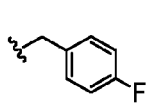 | 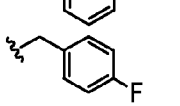 | 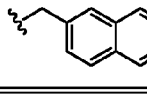 | OMe |
| 220 | His-Gly | 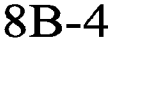 |  |  | OMe |
FIG. 18B-4

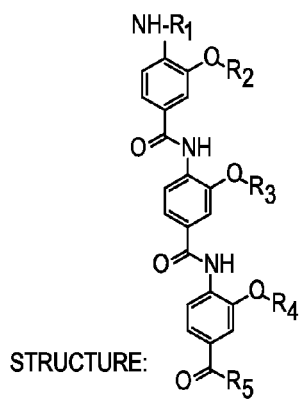

STRUCTURE:

| COMPOUND NUMBER | R1 | R2 | R3 | R4 | R5 |
|---|---|---|---|---|---|
| 221 | His | benzyl | isopropyl | 4-F-benzyl | OMe |
| 222 | His | phenethyl | isopropyl | 4-F-benzyl | OMe |
| 223 | His | pentafluorobenzyl | isopropyl | 4-F-benzyl | OMe |
| 224 | His | 4-F-benzyl | isopropyl | 4-F-benzyl | OMe |
| 225 | His | 4-OH-phenethyl | isopropyl | 4-F-benzyl | OMe |
| 226 | His | 2-naphthylmethyl | isopropyl | 4-F-benzyl | OMe |
| 227 | His | 1-naphthylmethyl | isopropyl | 4-F-benzyl | OMe |
| 228 | His | 3-thienylpropyl | isopropyl | 4-F-benzyl | OMe |
| 229 | His | imidazolylpropyl | isopropyl | 4-F-benzyl | OMe |
| 230 | His | benzyl | $-CH_3$ | 4-F-benzyl | OMe |
| 231 | His | benzyl | sec-butyl | 4-F-benzyl | OMe |
| 232 | His | benzyl | n-butyl | 4-F-benzyl | OMe |

FIG. 18C-1

| | | | | | |
|---|---|---|---|---|---|
| 233 | His | benzyl | isobutyl | 4-F-benzyl | OMe |
| 234 | His | benzyl | cyclohexylmethyl | 4-F-benzyl | OMe |
| 235 | His | benzyl | cyclopropylmethyl | 4-F-benzyl | OMe |
| 236 | His | benzyl | 4-F-benzyl | 4-F-benzyl | OMe |
| 237 | His | benzyl | benzyl | benzyl | OMe |
| 238 | His | benzyl | isobutyl | benzyl | OMe |
| 239 | His | benzyl | isobutyl | pentafluorobenzyl | OMe |
| 240 | His | benzyl | isobutyl | 4-OH-benzyl | OMe |
| 241 | His | benzyl | isobutyl | 2-naphthylmethyl | OMe |
| 242 | His | benzyl | isobutyl | 1-naphthylmethyl | OMe |
| 243 | His | benzyl | isobutyl | 3-thienylmethyl | OMe |
| 244 | His | benzyl | isobutyl | imidazolylmethyl | OMe |
| 245 | His | imidazolylethyl | imidazolylmethyl | imidazolylmethyl | OMe |
| 246 | His | imidazolylethyl | isobutyl | 4-OH-benzyl | OMe |
| 247 | His | imidazolylethyl | isobutyl | 4-OH-benzyl | OMe |
| 248 | His | benzyl | phenethyl | phenethyl | OMe |
| 249 | His | benzyl | pentafluorobenzyl | pentafluorobenzyl | OMe |
| 250 | His | -CH₃ | -CH₃ | -CH₃ | OMe |
| 251 | His | isobutyl | isobutyl | isobutyl | OMe |

FIG. 18C-2

| | | | | | |
|---|---|---|---|---|---|
| 252 | His | isobutyl | isobutyl | isobutyl | OMe |
| 253 | His | n-butyl | n-butyl | n-butyl | OMe |
| 254 | His | -CH₂CH₂OH | -CH₂CH₂OH | -CH₂CH₂OH | OMe |
| 255 | His | -CH₂CH₂OH | -CH₂CH₂OH | -(CH₂)₃COOH | OMe |
| 256 | His | -(CH₂)₃COOH | -(CH₂)₄NH₂ | -(CH₂)₃COOH | OMe |
| 257 | His | -(CH₂)₄NH₂ | -(CH₂)₃COOH | -(CH₂)₄NH₂ | OMe |
| 258 | His | -CH₂CH(OH)CH₃ | -(CH₂)₃COOH | -(CH₂)₄NH₂ | OMe |
| 259 | His | -CH₂CH₂OH | -(CH₂)₃COOH | -(CH₂)₃NHC(NH)NH₂ | OMe |
| 260 | His | -(CH₂)₃COOH | -(CH₂)₃NHC(NH)NH₂ | -(CH₂)₃COOH | OMe |
| 261 | His | -(CH₂)₃NHC(NH)NH₂ | -(CH₂)₃NHC(NH)NH₂ | -(CH₂)₃NHC(NH)NH₂ | OMe |
| 262 | His | -CH₂-imidazole | -CH₂CH₂-Ph | -(CH₂)₃COOH | OMe |
| 263 | His | -CH₂-Ph | -(CH₂)₃COOH | -CH₂-(4-F-Ph) | OMe |
| 264 | His | -CH₂-Ph | -(CH₂)₃COOH | -CH₂CH₂-(4-OH-Ph) | OMe |
| 265 | His | -CH₃ | -CH₂-Ph | -CH₂-naphthyl | OMe |
| 266 | His | -CH₃ | -CH₂CH₂-Ph | -CH₂-naphthyl | OMe |
| 267 | His | -CH₃ | -CH₂-(4-F-Ph) | -CH₂-naphthyl | OMe |
| 268 | His | -CH₃ | -CH₂-naphthyl | -CH₂-naphthyl | OMe |
| 269 | His | -CH₃ | -CH₂-(1-naphthyl) | -CH₂-naphthyl | OMe |
| 270 | His | -CH₃ | -CH₂-C₆F₅ | -CH₂-naphthyl | OMe |

FIG. 18C-3

| 272 | His | ξ-CH₃ | 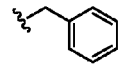 | 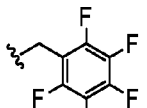 | OMe |
| 273 | His | ξ-CH₃ | 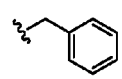 | 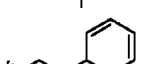 | OMe |
| 274 | His | ξ-CH₃ |  | 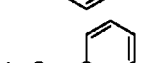 | OMe |
| 275 | His | ξ-CH₃ | 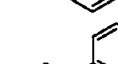 | 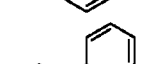 | OMe |
| 276 | His | ξ-CH₃ | 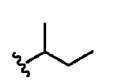 | 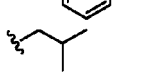 | OMe |
| 277 | His | ξ-CH₃ | 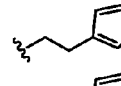 | 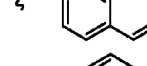 | OMe |
| 278 | His | ξ-CH₃ | 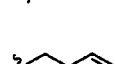 | 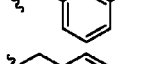 | OMe |
| 279 | His | 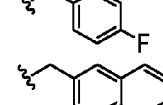 | 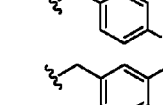 | 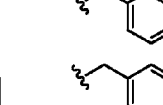 | OMe |
| 280 | His | 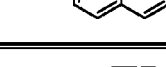 | 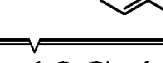 |  | OMe |
FIG. 18C-4

STRUCTURE:

(structure showing a diaryl amide with NH-R₁, O-R₂ on one ring and O-R₃, C(O)-R₄ on the other)

| COMPOUND NUMBER | R1 | R2 | R3 | R4 |
|---|---|---|---|---|
| 281 | His | benzyl | 4-fluorobenzyl | OMe |
| 282 | His | phenethyl | 4-fluorobenzyl | OMe |
| 283 | His | pentafluorobenzyl | 4-fluorobenzyl | OMe |
| 284 | His | 4-fluorobenzyl | 4-fluorobenzyl | OMe |
| 285 | His | 4-hydroxyphenethyl | 4-fluorobenzyl | OMe |
| 286 | His | 2-naphthylmethyl | 4-fluorobenzyl | OMe |
| 287 | His | 1-naphthylmethyl | 4-fluorobenzyl | OMe |
| 288 | His | 3-thienylmethyl | 4-fluorobenzyl | OMe |
| 289 | His | (1H-imidazol-4-yl)methyl | 4-fluorobenzyl | OMe |
| 290 | His | -CH₃ | 4-fluorobenzyl | OMe |
| 291 | His | isobutyl | 4-fluorobenzyl | OMe |
| 292 | His | sec-butyl | 4-fluorobenzyl | OMe |
| 293 | His | n-pentyl | 4-fluorobenzyl | OMe |
| 294 | His | isobutyl | 4-fluorobenzyl | OMe |

FIG. 18D-1

| 295 | His | phenethyl | 4-fluorobenzyl | OMe |
| 296 | His | cyclohexylmethyl | 3,4-difluorobenzyl | OMe |
| 297 | His | cyclopropylmethyl | cyclopropylmethyl | OMe |
| 298 | His | cyclopropylmethyl | benzyl | OMe |
| 299 | His | benzyl | pentafluorobenzyl | OMe |
| 300 | His | benzyl | 4-hydroxyphenethyl | OMe |
| 301 | His | benzyl | 2-naphthylmethyl | OMe |
| 302 | His | benzyl | 1-naphthylmethyl | OMe |
| 303 | His | benzyl | 3-thienylmethyl | OMe |
| 304 | His | benzyl | imidazolylethyl | OMe |
| 305 | His | imidazolylethyl | imidazolylethyl | OMe |
| 306 | His | imidazolylethyl | 4-hydroxyphenethyl | OMe |
| 307 | His | imidazolylethyl | cyclohexylmethyl | OMe |
| 308 | His | benzyl | phenethyl | OMe |
| 309 | His | benzyl | pentafluorobenzyl | OMe |
| 310 | His | -CH$_3$ | -CH$_3$ | OMe |
| 311 | His | isobutyl | isobutyl | OMe |
| 312 | His | sec-butyl | sec-butyl | OMe |
| 313 | His | pentyl | pentyl | OMe |
| 314 | His | hydroxyethyl | hydroxyethyl | OMe |

FIG. 18D-2

| # | | | | |
|---|---|---|---|---|
| 315 | His | ⁓OH | ⁓COOH | OMe |
| 316 | His | ⁓COOH | ⁓COOH | OMe |
| 317 | His | ⁓(CH$_2$)$_2$NH$_2$ | ⁓(CH$_2$)$_2$NH$_2$ | OMe |
| 318 | His | ⁓CH(OH)CH$_3$ | ⁓(CH$_2$)$_2$NH$_2$ | OMe |
| 319 | His | ⁓OH | ⁓NHC(NH)NH$_2$ | OMe |
| 320 | His | ⁓COOH | ⁓COOH | OMe |
| 321 | His | ⁓NHC(NH)NH$_2$ | ⁓NHC(NH)NH$_2$ | OMe |
| 322 | His | ⁓(imidazole) | ⁓COOH | OMe |
| 323 | His | ⁓Bn | ⁓(4-F-Ph) | OMe |
| 324 | His | ⁓Bn | ⁓(4-OH-Ph) | OMe |
| 325 | His | –CH$_3$ | ⁓Bn | OMe |
| 326 | His | –CH$_3$ | ⁓(pentafluorophenyl) | OMe |
| 327 | His | –CH$_3$ | ⁓(4-F-Ph) | OMe |
| 328 | His | –CH$_3$ | ⁓(4-OH-Ph) | OMe |
| 329 | His | –CH$_3$ | ⁓(2-naphthyl) | OMe |
| 330 | His | –CH$_3$ | ⁓(1-naphthyl) | OMe |
| 332 | His | –CH$_3$ | ⁓(3-thienyl) | OMe |
| 333 | His | –CH$_3$ | ⁓(imidazole) | OMe |

FIG. 18D-3

| STRUCTURE: | | | | | | | |
|---|---|---|---|---|---|---|---|
| COMPOUND NUMBER | R1 | R2 | R3 | R4 | R5 | R6 | R7 |
| 621 | His | benzyl | isopropyl | 4-F-benzyl | (CH2)2OH | 4-F-benzyl | OMe |
| 622 | His | phenethyl | isopropyl | 4-F-benzyl | (CH2)2OH | 4-F-benzyl | OMe |
| 623 | His | 2,3,5,6-tetrafluorobenzyl | isopropyl | 4-F-benzyl | (CH2)2OH | 4-F-benzyl | OMe |
| 624 | His | 3-F-benzyl | isopropyl | 4-F-benzyl | (CH2)2OH | 4-F-benzyl | OMe |
| 625 | His | 4-OH-phenethyl | isopropyl | 4-F-benzyl | (CH2)2OH | 4-F-benzyl | OMe |

SEQUENCE LISTING

<160> NUMBER OF SEQ ID NOS: 1

<210> SEQ ID NO 1
<211> LENGTH: 30
<212> TYPE: PRT

```
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

COMPOSITION AND METHOD FOR THE TREATMENT OF DISEASES AFFECTED BY A PEPTIDE RECEPTOR

CROSS-REFERENCE TO RELATED APPLICATIONS

This application claims priority to U.S. Provisional Application Ser. No. 60/894,580 filed Mar. 13, 2007, the contents of which is incorporated by reference herein in its entirety.

TECHNICAL FIELD OF THE INVENTION

The present invention relates in general to the field of peptidomimetics and specifically to compositions of matter, kits and methods of making and using the compositions to mimic peptides for the treatment of diseases.

BACKGROUND OF THE INVENTION

Without limiting the scope of the invention, its background is described in connection with compositions that mimic peptides and proteins, methods of making the compositions and using the compositions in the treatment of diseases. Diabetes mellitus, and associated complications, is the third leading cause of death in the United States and one of the most widespread degenerative diseases. Generally, diabetes mellitus affects the conversion of sugars and starches into glucose during digestion. A pancreatic hormone, insulin, plays a key role in the storage and use of carbohydrates, protein and fat as a source of energy for the body. Insulin deficiency is a common and serious pathologic condition, which may lead to blindness, kidney failure and limb amputations.

Diabetes is a chronic disease characterized by multiple metabolic abnormalities resulting in impaired management of glucose. Generally, diabetes can be classified into insulin-dependent diabetes mellitus (Type I) and non-insulin-dependent diabetes mellitus (Type II). Insulin-dependent diabetes mellitus (Type I) is characterized by the production of little or no insulin by the pancreas and requires daily insulin injections for treatment. Non-insulin-dependent diabetes mellitus (Type II) is characterized by a combination of reduced insulin responsiveness and a relative deficiency of insulin production. The most common form of diabetes is Type II, which affects about 90-95% of diabetic patients.[1,2] The treatment of non-insulin-dependent diabetes mellitus (Type II) is more challenging due to the complex pathogenesis involving progressive development of insulin resistance and deficiency in insulin secretion.[4]

The major pancreatic islet hormones, glucagon, insulin and somatostatin, interact with and/or originate from specific pancreatic cell types to modulate the secretory response. Glucagon is derived from the processing of proglucagon, which is in itself derived from the 360 base pair preproglucagon gene. However, proglucagon also contains two other discrete and highly homologous peptide regions designated glucagon, glucagon-like peptide-1 (GLP-1) and glucagon-like peptide-2 (GLP-2). The 30-amino acid glucagon-like peptide-1 (GLP-1) has been shown to function as a stimulus of insulin secretion.

GLP-1[14] is produced by intestinal L-cells through the proteolytical processing of preproglucagon.[5-8] GLP-1 functions by acting on a cognate peptide receptor (GLP-1R). In addition to enhancing insulin secretion and restoring glucose sensitivity to the islets, this peptide also increases expression of the glucose transporter and glucokinase.[14-16]

Additionally, GLP-1 displays numerous beneficial effects on regulating β-cell mass by stimulating replication and growth of existing β-cells, inhibiting apoptosis, and triggering neogenesis of new β-cells from duct precursor cells.[17,18] GLP-1 also inhibits secretion of glucagon which is often found in abnormally high concentrations in diabetic patients.[19,20] Apart from these effects, it is a potent inhibitor of gastric emptying,[21] and causes an inhibition of appetite with suppression of food intake. This results in a decrease in body weight, making GLP-1 an efficient treatment of obesity which often accompanies diabetes.[22,23] Since all these GLP-1 induced functions are extremely favorable to the treatment of Type II diabetes, therapies based on this peptide hold considerable clinical promise.[24]

For example, one method for regulation of glucose and lipid metabolism, generally to reduce hyperglycemia, insulin resistance, obesity, hyperlipidemia, and hyperlipoproteinemia, is taught in U.S. Pat. No. 7,157,429 issued to Bachovchin, et al. entitled Method of regulating glucose metabolism and reagents related thereto. It includes dipeptidylpeptidase inhibitors, which are able to inhibit the proteolysis of GLP-1 and accordingly increase the plasma half-life of that hormone. The subject inhibitors may be peptidyl, peptidomimetic (e.g. boronyl peptidomimetics), or non-peptidyl nitrogen containing heterocycles.

Conventional methods for identifying such inhibitors include the preparation and screening of chemical libraries to discover lead compounds although often with little success.

SUMMARY OF THE INVENTION

The present inventors recognized that a rational design approach provides a compelling alternative to conventional methods. The present inventors recognized that based on a structural knowledge of the interface of protein complexes. The present inventors recognized that α-helix mimetics may be used to modulate protein-protein or protein-peptide interaction. In particular, synthetic scaffolds that mimic key elements found in the interface can potentially lead to develop potent small molecule modulators. The present inventors recognized that mimetics can be used to interact with complexes of various types. For example the mimetics can be used to interact with a peptide receptor, including a GLP-1 receptor for diabetes application. The present inventors also recognized that the mimetics of the present invention may be used to interact with other cellular proteins, surface proteins and protein complexe.

The present inventors recognized that numerous drugs (e.g., insulin, insulin-sensitizing drugs, and cancer treatment drugs) are employed to treat diabetes, but they do not address the issue of dying pancreatic β-cells, a fundamental dysfunction observed in diabetes. Furthermore, treatment with these drugs tends to increase body weight and often carries an enhanced risk of triggering accidental hypoglycemic episodes where blood glucose levels are temporarily too low.

The present inventors recognized that glucagon-like peptide-1 (GLP-1) agonists have unique antidiabetic functions (e.g., by stimulating insulin secretion, restoring glucose sensitivity to the pancreatic islets, regulating β-cell mass, and suppressing glucagon secretion). However, as a result of their peptide structure the currently known agonists are susceptible to rapid enzymatic degradation, and require i.v. or s.c. administration. In addition, there is a risk of developing an immune response against these peptide therapeutics.

The present inventors recognized a need for stable small molecules possessing the capability to activate the GLP-1 receptor (GLP-1R) but lacking the limitations of the peptide structure. The present invention provides a class of small molecules that are stable and capable of activating the GLP-1 receptor (GLP-1R) but lacking the limitations of the peptide structure. These small molecules include α-helix mimetics that represent helical segments in GLP-1.

The present invention provides a method of modifying glucose metabolism in a glucose intolerant subject by administering an oligo-benzamide peptidomimetic to the subject suspected of being glucose intolerant. The oligo-benzamide peptidomimetic compound includes at least two optionally substituted benzamides, with each of the substituted benzamides having one or more substitutions on a benzene ring. The oligo-benzamide peptidomimetic compound modifies glucose metabolism by reducing one or more of hyperglycemia, insulin resistance, glucose intolerance, obesity, hyperlipidemia, or hyperlipoproteinemia.

Another embodiment of the present invention is the addition of a third optionally substituted benzamide connected to one of the at least two optionally substituted benzamides, and the third optionally substituted benzamide may include one or more substitutions on a benzene ring. The present invention also provides an oligo-benzamide peptidomimetic compound that includes at least two optionally substituted benzamides with one or more substitutions on a benzene ring.

The present invention also provides a peptidomimetic compound that at least partially activates or inhibits a peptide receptor. The peptidomimetic compound includes a tris-benzamide peptidomimetic, three optionally substituted benzamides and one or more substituted groups attached to each of the substituted benzamides individually by a chemical bond including ether, thioether, amine, aminde, carbamate, urea, and carbon-carbon (single, double, and triple) bonds.

The present invention provides a method for treating a subject that would benefit from stimulating or inhibiting a peptide receptor by administering to the subject an oligo-benzamide peptidomimetic compound comprising more than two optionally substituted benzamides and one or more substituted groups attached to each of the substituted benzamides individually by a chemical bond including ether, thioether, amine, amide, carbamate, urea, and carbon-carbon (single, double, and triple) bonds. The pharmaceutical peptidomimetic compound may be adapted for oral, dermatological, transdermal or parenteral administration.

Peptide receptors typically reside on the cell membrane and serve as recognition sites of peptide hormones/transmitters (such as GLP-1). These peptides may be either locally produced (within the same tissue) or may be generated elsewhere in the body and are transported to the target tissue via the blood stream (such as GLP-1). Binding of the peptide to its cognate receptor modulates a wide range of cellular functions such as intracellular signaling, growth, apoptosis, secretion, differentiation, electrical excitation or inhibition, gene expression, and many others.

Peptide receptors are known to comprise two major superfamilies. One of these includes single transmembrane domain proteins which often function as dimers, e.g. receptors responding to insulin, epidermal growth factor, and erythropoietin. Another receptor superfamily comprises G-protein coupled receptors (GPCRs). Within the latter group, peptide receptors are mostly found in the class A (rhodopsin-like) and class B subfamilies. The GLP-1R falls within the class B GPCR subfamily.

Endogenous peptide ligands which act on peptide receptors typically have a distinct tertiary structure that enables these molecules to selectively recognize receptors with high affinity and to modulate their functions. One defining structural feature of such peptides are α-helices, i.e. structures in which the amino acid side chains are placed in a circular orientation with a characteristic angle of 100° between adjacent residues. For example, this structural hallmark plays an important role in the function of GLP-1 and of other ligands that act on class B GPCRs.

The present invention provides a pharmaceutical peptidomimetic composition for treating one or more glucose metabolism diseases (e.g., hyperglycemia, insulin resistance, hyperinsulinemia, obesity, hyperlipidemia, hyperlipoproteinemia or a combination thereof) and other medical symptoms related to peptide receptors. The pharmaceutical peptidomimetic composition includes a therapeutically effective amount of an oligo-benzamide peptidomimetic compound or a salt, a solvate, or a derivative thereof having an oligo-benzamide peptidomimetic compound and one or more pharmaceutically acceptable carriers. The oligo-benzamide peptidomimetic compound includes more than two optionally substituted benzamides (e.g., substituted and/or non-substituted benzamides) and one or more substituted groups attached to each of the substituted benzamides individually by a chemical bond including ether, thioether, amine, amide, carbamate, urea, and carbon-carbon (single, double, and triple) bonds.

The present invention provides a peptidomimetic compound having the formulas:

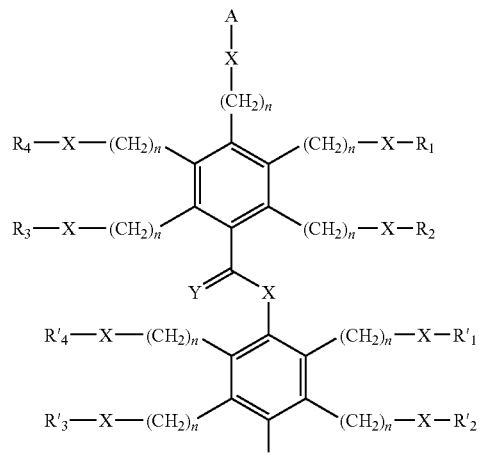

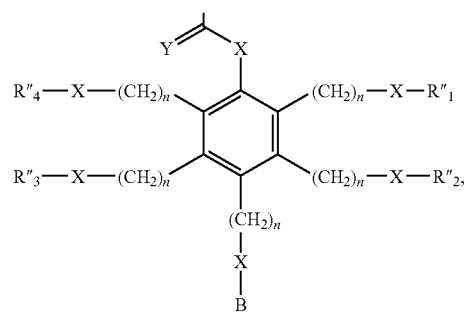

-continued

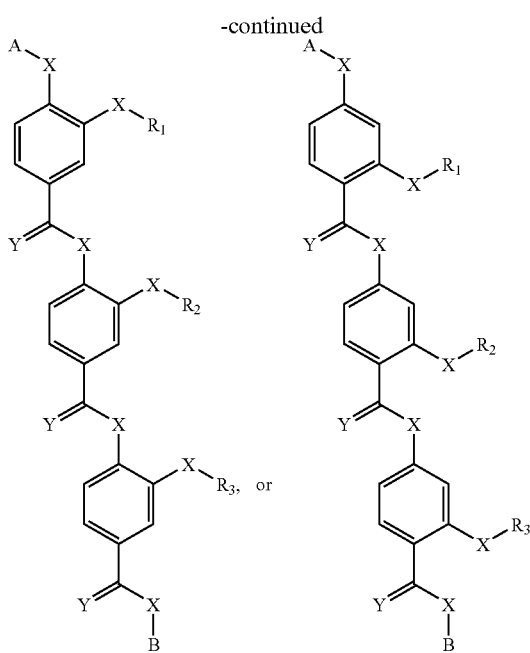

The present invention provides an oligo-benzamide peptidomimetic compound containing at least two optionally substituted benzamides. Each of the optionally substituted benzamides may be optionally substituted on the benzene ring with one or more substitutions.

BRIEF DESCRIPTION OF THE DRAWINGS

For a more complete understanding of the features and advantages of the present invention, reference is now made to the detailed description of the invention along with the accompanying figures and in which:

FIG. 14 is the primary structure of GLP-1 (SEQ ID NO: 1);

FIGS. 16A-16K are structures of various α-helix peptidomimetics compounds;

FIGS. 18A-18K are structures of additional subset of the α-helix peptidomimetics compounds described in the current invention.

DETAILED DESCRIPTION OF THE INVENTION

Figure 1A:
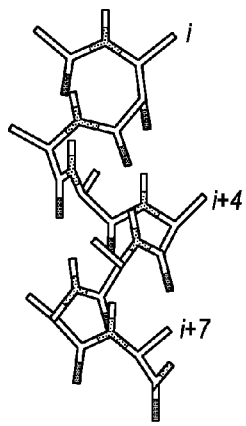
FIGS. 1A-1E are images of the structure of α-helix peptidomimetic compounds that represent one α-helical face of a peptide.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein an "Agonist" is a molecule that selectively binds to a specific receptor and triggers a response. Generally, an Agonist mimics the action of an endogenous biochemical molecule (e.g., hormone or neurotransmitter) that binds to the receptor. As used herein an "Antagonist" binds to the receptor but does not activate the receptor and actually blocks it from activation by agonists. As used herein a "Partial Agonist" activates a receptor, but only produces a partial response compared to a full agonist. As used herein a "Co-agonist" works with other co-agonists to produce the desired effect together. As used herein, an "Inverse Agonist" provides responses that inhibit constitutive, ligand-independent basal activity of a receptor and thus shows a function which is in some way opposite to that of Agonists.

As used herein, the term "Alkyl" denotes branched or unbranched hydrocarbon chains, having between about 1-20 carbons, with "lower Alkyl" denoting branched or unbranched hydrocarbon chains, having between about 1-10 carbons. Non-limiting examples include methyl, ethyl, propyl, n-propyl, isopropyl, butyl, n-butyl, sec-butyl, isobutyl, t-butyl, 1-methylpropyl, pentyl, isopentyl, sec-pentyl, 2-methylpentyl, hexyl, heptyl, octyl, nonyl, decyl, octadecyl and so on. Alkyl includes cycloalkyl, such as cyclopropyl, cyclobutyl, cyclopentyl, and cyclohexyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, carboxamidyl, alkoxycarbonyl, carbamoyl, alkyl, alkenyl, alkynyl, nitro, amino, alkoxy, amido, imino, imido, guanidino, hydrazido, aminoxy, alkoxyamino, and the like to form alkyl groups such as trifluoro methyl, 3-hydroxyhexyl, 2-carboxypropyl, 2-fluoroethyl, carboxymethyl, cyanobutyl and the like.

As used herein, the term "Aryl" denotes a chain of carbon atoms which form at least one aromatic ring having between about 4-20 carbon atoms, such as phenyl, naphthyl, biphenyl, anthracenyl, pyrenyl, tetrahydronaphthyl, and so on, any of which may be optionally substituted. Aryl also includes arylalkyl groups such as benzyl, phenethyl, and phenylpropyl. Aryl includes a ring system containing an optionally substituted 5 or 6-membered carbocyclic aromatic ring, said system may be bicyclic, polycyclic, bridge, and/or fused. The system may include rings that are aromatic, or partially or completely saturated. Examples of ring systems include phenyl, naphtyl, biphenyl, anthracenyl, pyrenyl, imidazolyl, triazolyl, tetrazolyl, oxazolyl, thiophenyl, pyridyl, pyrrolyl, furanyl, quinolyl, quinolinyl, indenyl, pentalenyl, 1,4-dihydronaphthyl, indanyl, benzimidazolyl, benzothiophenyl, indolyl, benzofuranyl, isoquinolinyl, and so on. The group may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, carboxamidyl, alkoxycarbonyl, carbamyl, alkyl, alkenyl, alkynyl, nitro, amino, alkoxy, amido, imino, imido, guanidino, hydrazido, aminoxy, alkoxyamino and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, aminophenyl, amidophenyl, thiazolylphenyl, oxazolylphenyl, imidazolylphenyl, imidazolylmethylphenyl, and the like.

As used herein, the term "Alkenyl" includes optionally substituted straight chain and branched hydrocarbons having between about 1-50 carbons as above with at least one carbon-carbon double bond (sp$^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbons having a mixture of double bonds and triple bonds, such as 2-penten-4-ynyl, are grouped as alkynyls herein. Alkenyl includes cycloalkenyl. Cis and trans or (E) and (Z) forms are included within the invention. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, carboxamidyl, alkoxycarbonyl, carbamoyl, alkyl, alkenyl, alkynyl, nitro, amino, alkoxy, amido, imino, imido, guanidino, hydrazido, aminoxy, alkoxyamino and the like to form alkyl groups such as trifluoro methyl, 3-hydroxyhexyl, 2-carboxypropyl, 2-fluoroethyl, carboxymethyl, cyanobutyl and the like.

As used herein, the term "Alkynyl" includes optionally substituted straight chain and branched hydrocarbons having between about 1-50 carbons as above with at least one carbon-carbon triple bond (sp). Alkynyls include ethynyl, propynyls, butynyls, and pentynyls. Hydrocarbons having a mixture of double bonds and triple bonds, such as 2-penten-4-ynyl, are grouped as alkynyls herein. Alkynyl does not include cycloalkynyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, carboxamidyl, alkoxycarbonyl, carbamoyl, alkyl, alkenyl, alkynyl, nitro, amino, alkoxy, amido, imino, imido, guanidino, hydrazido, aminoxy, alkoxyamino and the like to form alkyl groups such as trifluoro methyl, 3-hydroxyhexyl, 2-carboxypropyl, 2-fluoroethyl, carboxymethyl, cyanobutyl and the like.

As used herein, the term "Alkoxy" includes an optionally substituted straight chain or branched alkyl group having between about 1-50 carbons with a terminal oxygen linking the alkyl group to the rest of the molecule. Alkoxy includes methoxy, ethoxy, propoxy, isopropoxy, butoxy, t-butoxy, pentoxy and so on. Alkyoxy also includes any substituted alkyl group connected by an ether linkage, such as aminobutoxy, carboxyethoxy, hydroxyethoxy and so on. "Aminoalkyl", "thioalkyl", and "sulfonylalkyl" are analogous to alkoxy, replacing the terminal oxygen atom of alkoxy with, respectively, NH (or NR), S, and SO$_2$. Heteroalkyl includes alkoxy, aminoalkyl, thioalkyl, and so on.

As used herein, the term "pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

As used herein, the term "Pharmaceutically Acceptable Salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically Acceptable Salts also include base addition salts, which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

As used herein, the term "Subject" includes humans, non-human mammals (e.g., dogs, cats, rabbits, cattle, horses, sheep, goats, swine, deer, monkeys and the like) and non-mammals (e.g., birds, reptiles and the like).

As used herein, the term "Treatment" or "Treating" means any administration of a compound which at least partially prevents the disease from occurring in a subject who may be predisposed to the disease but does not yet experience or display the pathology or symptomotology of the disease, arrests further development or inhibits the disease in a subject that is experiencing or displaying the pathology or symptomotology of the disease, or ameliorates the disease in a subject that is experiencing or displaying the pathology or symptomotology of the disease. The term "Disease" is used here to describe a condition that is characterized by suboptimal function of physiological (including mental) processes, and is used here in its widest sense including undesirable cosmetic appearance.

The present invention provides a method of modifying glucose metabolism in a diabetic subject by administering an oligo-benzamide peptidomimetic to the subject suspected of being diabetic, or to be at risk of becoming diabetic. The oligo-benzamide peptidomimetic compound includes at least two optionally substituted benzamides, with each of the substituted benzamides having one or more substitutions on a benzene ring. The oligo-benzamide peptidomimetic compound modifies glucose metabolism by reducing one or more of hyperglycemia, insulin resistance, glucose intolerance, obesity, hyperlipidemia, hyperlipoproteinemia, and other medical symptoms related to peptide receptors. Although the oligo-benzamide peptidomimetic compound as illustrated includes 2 or 3 optionally substituted benzamides, the number of optionally substituted benzamides may be 4, 5, 6, 7, 8, 9, 10 or more. In addition, linkages between the optionally substituted benzamides may be varied as necessary including ester, thioester, thioamide, trans-ethylene, ethyl, methyloxy, methylamino, hydroxyethyl, carbamate, urea, imide, hydrozido, aminoxy, or other linkages known to the skilled artisan. And, the oligo-benzamide peptidomimetic compound may be attached to amino acids, oligopeptides, optionally substituted alkyl, or other structures known to the skilled artisan.

The substitutions on the substituted benzamide are generally on a benzene ring and may be on the 2, 3, 4, 5, or 6 position of each of the benzene rings. The substitutions may be at the same position on each of the benzamide rings but may also be at different positions on each of the benzene rings. The one or more substitutions may include any necessary functional groups to achieve the desired effect. For example, the one or more substitutions are connected to the benzamide ring by a chemical linkage including ether, thioether, amine, amide, carbamate, urea, and carbon-carbon (single, double, and triple) bonds, and the one or more substitutions comprise one or more optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, carboxamido groups, carbamoyl groups, carboxyl groups, carbonyl groups, alkoxycarbonyl groups, halogen groups, haloalkyl groups, haloalkoxy groups, heteroaryl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof.

The present invention also provides an oligo-benzamide peptidomimetic compound that includes at least two optionally substituted benzamides, with each of the substituted benzamides having one or more substitutions on a benzene ring. The one or more substitutions are individually attached to the benzene rings of the oligo-benzamide peptidomimetic compound by a chemical linkage including ether, thioether, amine, amide, carbamate, urea, and carbon-carbon (single, double, and triple) bonds. The one or more substitutions generally include one or more optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, carboxamido groups, carbamoyl groups, carboxyl groups, carbonyl groups, alkoxycarbonyl groups, halogen groups, haloalkyl groups, haloalkoxy groups, heteroaryl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof.

The substitutions may be on a single first face of the oligo-benzamide peptidomimetic compound to form an α-helix oligo-benzamide peptidomimetic compound or on two faces of the oligo-benzamide peptidomimetic compound to form an amphiphilic α-helix oligo-benzamide peptidomimetic compound.

A third optionally substituted benzamide with one or more optional substitutions on a benzene ring may be connected to one of the at least two optionally substituted benzamides. The present invention also provides an oligo-benzamide peptidomimetic compound having one or more substitutions on a first face and a second face of the oligo-benzamide peptidomimetic compound, wherein an amphiphilic α-helix oligo-benzamide peptidomimetic is formed. The one or more substitutions are at one or more positions of the oligo-benzamide peptidomimetic selected from an i position, an i+2 position, an i+3 position, an i+4 position, an i+5 position, and an i+7 position of a target peptide hormone. For example, one of the one or more substitutions correspond to an i position, one of the one or more substitutions correspond to an i+3 position or an i+4 position, and one of the one or more substitutions correspond to an i+7 position of a target peptide hormone.

The present invention provides a pharmaceutical peptidomimetic composition for treating one or more of glucose metabolism diseases (e.g., hyperglycemia, insulin resistance, hyperinsulinemia, obesity, hyperlipidemia, hyperlipoproteinemia or a combination thereof) and other medical symptoms based on peptide receptors. The pharmaceutical peptidomimetic composition includes a therapeutically effective amount of an oligo-benzamide peptidomimetic compound or a salt, a solvent, or a derivative thereof based on an oligo-benzamide peptidomimetic compound, and one or more pharmaceutically acceptable carriers. For example, the tris-benzamide peptidomimetic compound includes three optionally substituted benzamides and one or more substituted groups attached to each of the substituted benzamides individually by a chemical linkage including ether, thioether, amine, amide, carbamate, urea, and carbon-carbon (single, double, and triple) bonds. The pharmaceutical peptidomimetic composition may also include one or more additional active ingredients, diluents, excipients, active agents, lubricants, preservatives, stabilizers, wetting agents, emulsifiers, salts for influencing osmotic pressure, buffers, colorings, flavorings, aromatic substances, penetration enhancers, surfactants, fatty acids, bile salts, chelating agents, colloids and combinations thereof. The pharmaceutical peptidomimetic compound may be adapted for oral, dermatological, transdermal or parenteral administration, in the form of a solution, a emulsions, a liposome-containing formulation, a tablet, a capsule, a gel capsule, a liquid syrup, a soft gel, a suppository, an enema, a patch, an ointment, a lotion, a cream, a gel, a drop, a spray, a liquid or a powder.

The present invention provides peptidomimetic compounds having the formulas:

wherein each of the formulas may be substituted as follows. X may independently be a C, a N, a O, a S, a H, —$CH_2CH_2$—, —CH=CH—, —C≡C—, —NH—, —NR—, —NH—NH—, —NH($CH_2$)$_n$NH, —NR($CH_2$)$_n$NR'— —NR—NR'—, —NH—O—, —NR—O—, —NH($CH_2$)$_n$O—, —NR($CH_2$)$_n$O—, —NH($CH_2$)$_n$S—, —NR($CH_2$)$_n$S—, —O($CH_2$)$_n$O—, —O($CH_2$)$_n$S—, —S($CH_2$)$_n$O—, —CO—, —$CO_2$—, —COS—, —CONH—, —CONR—, —OC(O)NH—, —NHCONH—, —CONHCO—, —CO($CH_2$)$_n$CO—, or combination thereof, and Y may be independently a N, a O, a S or 2 H's. And, n is 0, 1, 2, 3, 4, 5, 6, 7 etc.

R1, R2, R3, R4, R'1, R'2, R'3, R'4, R"1, R"2, R"3, and R"4, comprise independently a H, optionally substituted alkyl, lower alkyl, alkoxy, alkoxyalkyl, hydroxy, hydroxyalkyl, alkenyl, amino, imino, nitrate, alkylamino, dialkylamino, nitro, nitroso, aryl, biaryl, polycyclic aromatic, alkylaryl, arylalkyl, arylalkoxy, arylalkylamino, cycloalkyl, bridged cycloalkyl, cycloalkoxy, cycloalkyl-alkyl, arylthio, alkylthio, alkylsulfinyl, alkylsulfonyl, arylsulfonyl, arylsulfinyl, carboxamido, carbamoyl, carboxyl, carbonyl, alkoxycarbonyl, halogen, haloalkyl, haloalkoxy, heteroaryl, heterocyclic ring, arylheterocyclic ring, heterocyclic compounds, amido, imido, guanidino, hydrazido, aminoxy, alkoxyamino, alkylamido, urea, carboxylic ester, thioether, carboxylic acid, phosphoryl groups, polycyclic aromatic substituted with a OH, $NH_2$, SH, F, Cl, Br, I, NHR, NRR', $CN_3H_4$, a N, a O, a S, a H, or combination thereof.

Alternatively, R1, R2, R3, R4, R'1, R'2, R'3, R'4, R"1, R"2, R"3, and R"4 may be one or more of the following:

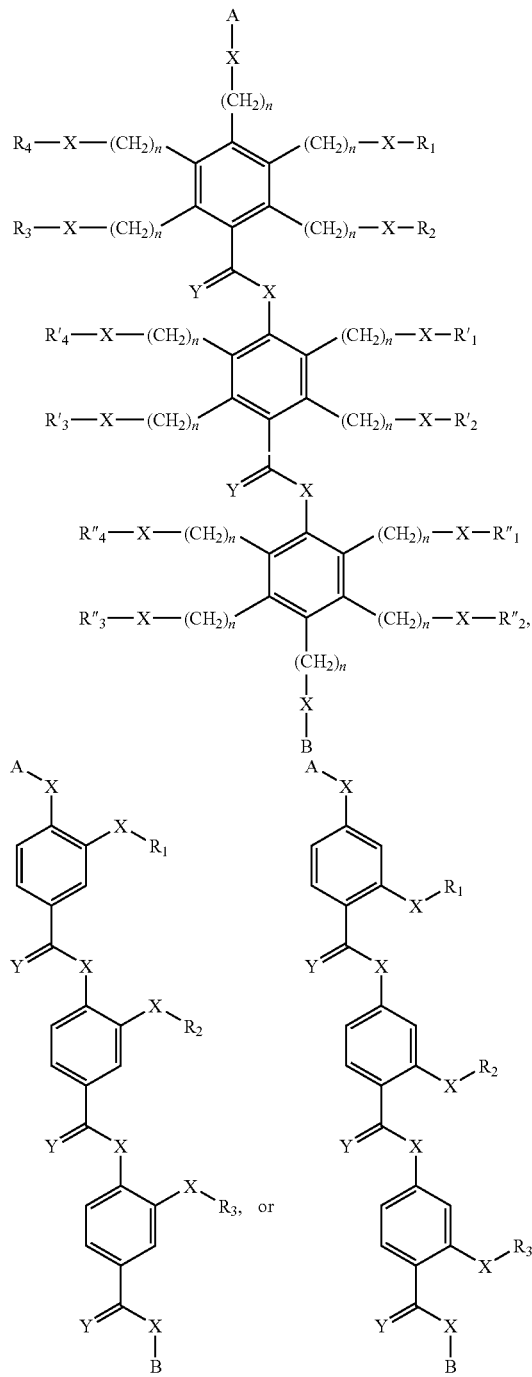

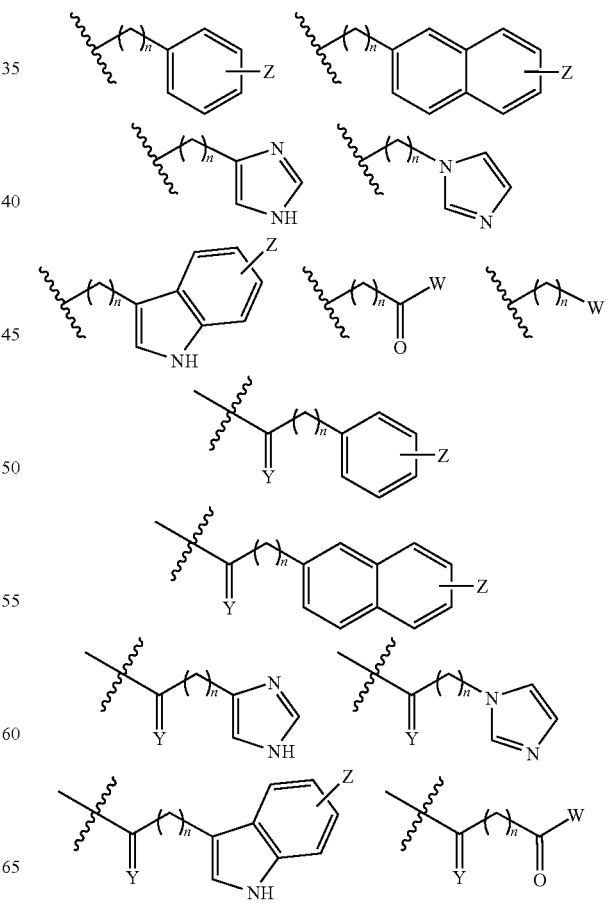

-continued

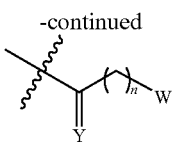

where Z is an OH, NH$_2$, SH, F, Cl, Br, I. W is an OH, an OR, a NH$_2$, a NHR, a NRR'(R, R" are alkyl groups), and an imine (C(NH)R$_1$R$_2$. For example, when R$_1$ is a NH$_2$ and R$_2$ is a NH the imine is actually a guanidine group), and n is 0, 1, 2, 3, 4, 5, 6, 7 etc.

"A" may be a substituent (R1, R2, R3, R4, R'1, R'2, R'3, R'4, R"1, R"2, R"3, or R"4), an acetyl, a Boc (t-butoxycarbonyl), a Fmoc (9-fluorenylmethoxycarbonyl), a Cbz (benzyloxycarbonyl), an Aloc (allyloxycarbonyl), an alkyl group, an alanine, an arginine, an asparagine, an aspartic acid, a cysteine, a glutamic acid, a glutamine, a glycine, a histidine, an isoleucine, a leucine, a lysine, a methionine, a phenylalanine, a proline, a serine, a threonine, a tryptophan, a tyrosine, a valine, dipeptide, tripeptide, tetrapeptide, pentapeptide, oligopeptide, dipeptide which has greater than 50% sequence homology to a portion of the GLP-1 sequence SEQ. ID. NO.: 1, tripeptide which has greater than 50% sequence homology to a portion of the GLP-1 sequence SEQ. ID. NO.: 1, tetrapeptide which has greater than 50% sequence homology to a portion of the GLP-1 sequence SEQ. ID. NO.: 1, pentapeptide which has greater than 50% sequence homology to a portion of the GLP-1 sequence SEQ. ID. NO.: 1, oligopeptide which consists of no greater than 30 amino acids and has greater than 50% sequence homology to a portion of the GLP-1 sequence SEQ. ID. NO.: 1, as seen in FIG. 14.

In addition "A" may be a linker as seen below

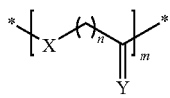

connected to a substituent (R1, R2, R3, R4, R'1, R'2, R'3, R'4, R"1, R"2, R"3, or R"4), an alanine, an arginine, an asparagine, an aspartic acid, a cysteine, a glutamic acid, a glutamine, a glycine, a histidine, an isoleucine, a leucine, a lysine, a methionine, a phenylalanine, a proline, a serine, a threonine, a tryptophan, a tyrosine, a valine, dipeptide, tripeptide, tetrapeptide, pentapeptide, oligopeptide, dipeptide which has greater than 50% sequence homology to a portion of the GLP-1 sequence SEQ. ID. NO.: 1, tripeptide which has greater than 50% sequence homology to a portion of the GLP-1 sequence SEQ. ID. NO.: 1, tetrapeptide which has greater than 50% sequence homology to a portion of the GLP-1 sequence SEQ. ID. NO.: 1, pentapeptide which has greater than 50% sequence homology to a portion of the GLP-1 sequence SEQ. ID. NO.: 1, oligopeptide which consists of no greater than 30 amino acids and has greater than 50% sequence homology to a portion of the GLP-1 sequence SEQ. ID. NO.: 1.

"B" may be a substituent (R1, R2, R3, R4, R'1, R'2, R'3, R'4, R"1, R"2, R"3, or R"4), an alanine, an arginine, an asparagine, an aspartic acid, a cysteine, a glutamic acid, a glutamine, a glycine, a histidine, an isoleucine, a leucine, a lysine, a methionine, a phenylalanine, a proline, a serine, a threonine, a tryptophan, a tyrosine, a valine, an alkyl group, dipeptide, tripeptide, tetrapeptide, pentapeptide, oligopeptide, a dipeptide which has greater than 50% sequence homology to a portion of the GLP-1 sequence SEQ. ID. NO.: 1, a tripeptide which has greater than 50% sequence homology to a portion of the GLP-1 sequence SEQ. ID. NO.: 1, a tetrapeptide which has greater than 50% sequence homology to a portion of the GLP-1 sequence SEQ. ID. NO.: 1, a pentapeptide which has greater than 50% sequence homology to a portion of the GLP-1 sequence SEQ. ID. NO.: 1, an oligopeptide which consists of no greater than 30 amino acids and has greater than 50% sequence homology to a portion of the GLP-1 sequence SEQ. ID. NO.: 1.

In addition "B" may be a dipeptide which has greater than 50% sequence homology to a portion of the GLP-1 sequence SEQ. ID. NO.: 1, a tripeptide which has greater than 50% sequence homology to a portion of the GLP-1 sequence SEQ. ID. NO.: 1, a tetrapeptide which has greater than 50% sequence homology to a portion of the GLP-1 sequence SEQ. ID. NO.: 1, a pentapeptide which has greater than 50% sequence homology to a portion of the GLP-1 sequence SEQ. ID. NO.: 1, an oligopeptide which consists of no greater than 30 amino acids and has greater than 50% sequence homology to a portion of the GLP-1 sequence SEQ. ID. NO.: 1, connected to compounds M1 to M12 of FIG. 15, or 19A of FIG. 19.

In addition "B" may be a linker as seen below

Figure 15:
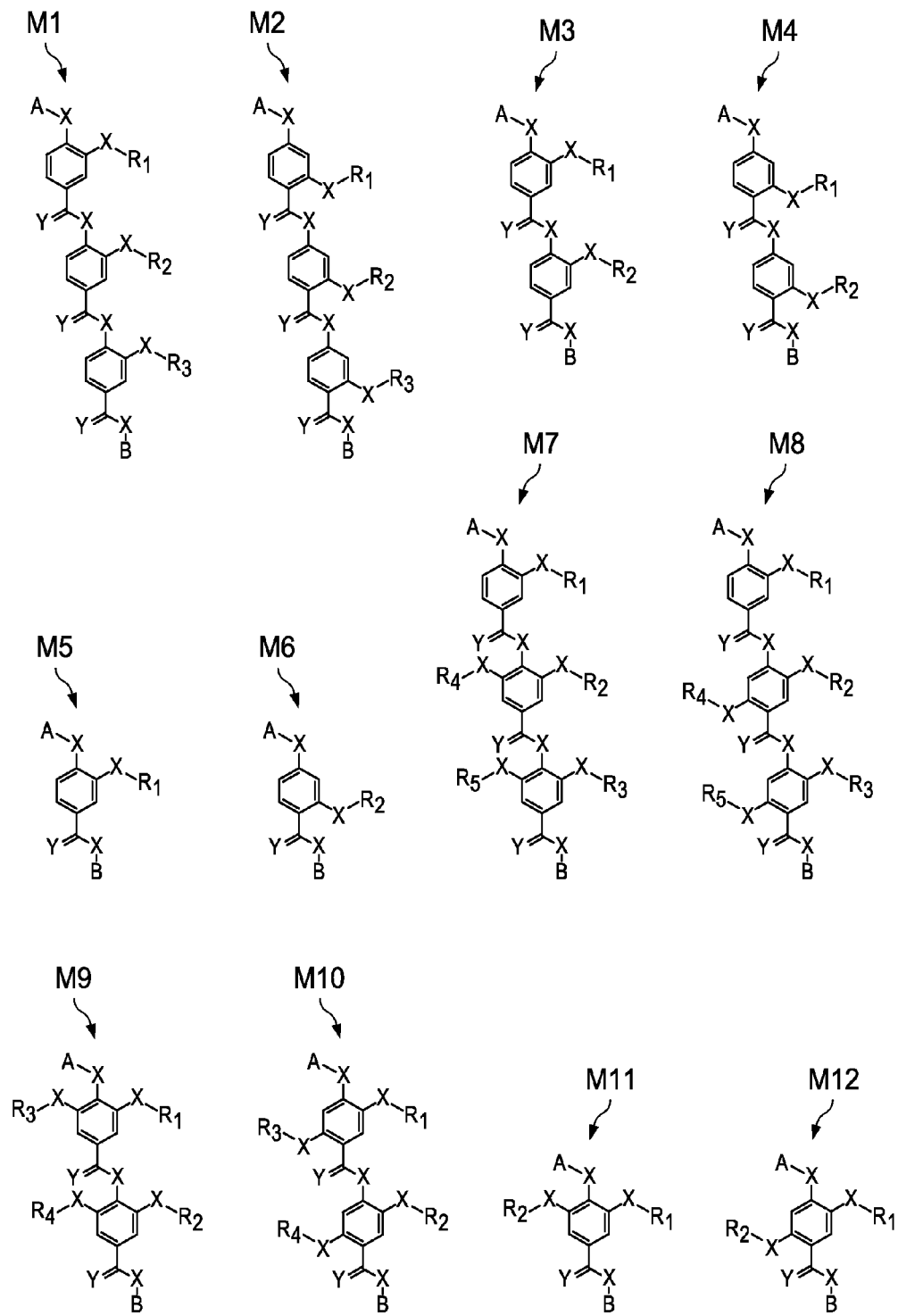
FIG. 15 is an image of various optionally substituted oligo-benzamide α-helix peptidomimetic compounds.
Figure 19C:
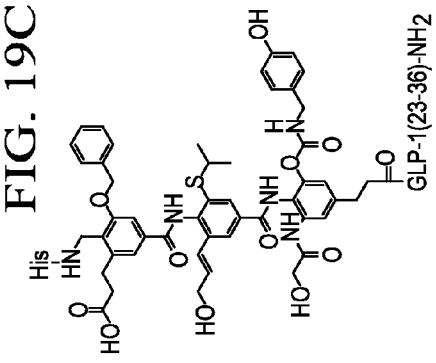
FIGS. 19A-19E are structures of another subset of the α-helix mimetics compounds described in the current invention.
Figure 19F:
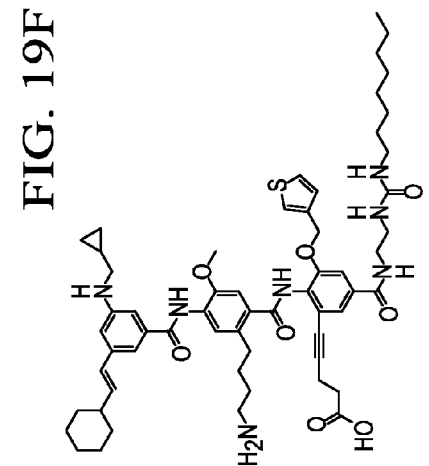
Figure 19B:
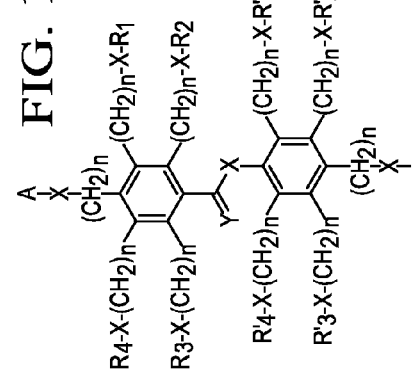
Figure 19E:
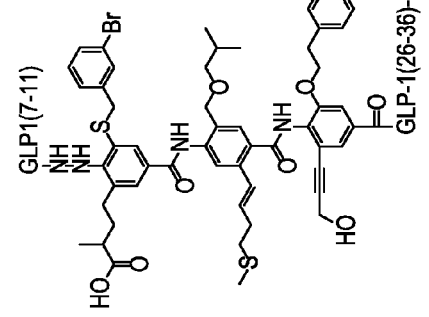
Figure 19A:
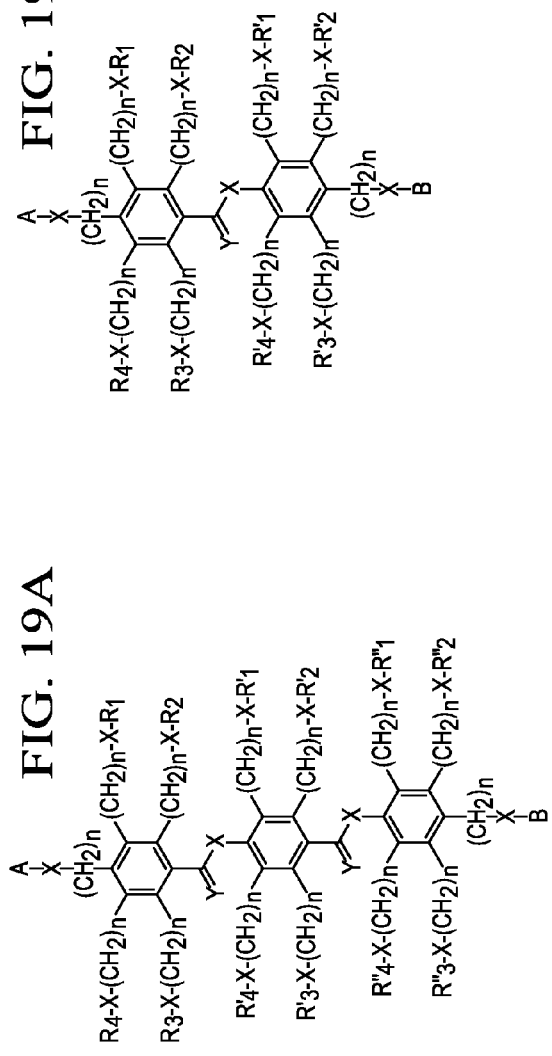
Figure 19D:
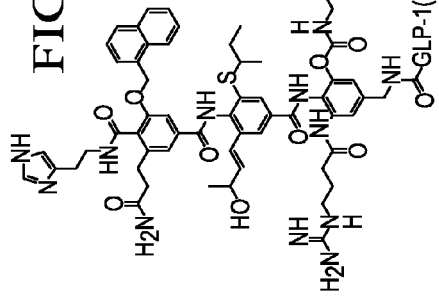

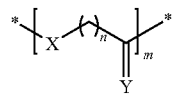

connected to a substituent (R1, R2, R3, R4, R'1, R'2, R'3, R'4, R"1, R"2, R"3, or R"4), an alkyl group, or one or more compounds M1 to M12 of FIG. 15, or 19A of FIG. 19.

The present invention provides an oligo-benzamide peptidomimetic compound having the formula:

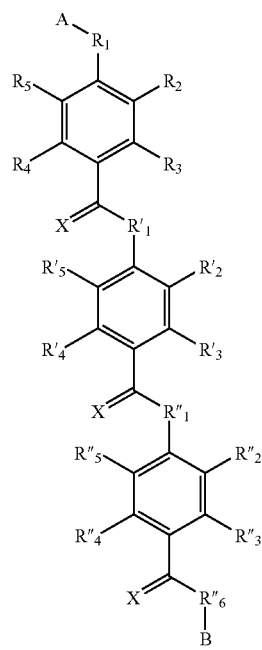

wherein R2, R3, R4, R5, R'2, R'3, R'4, R'5, R"2, R"3, R"4, and R"5 independently comprise a H, one or more optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, carboxamido groups, carbamoyl groups, urea groups, carboxyl groups, carbonyl groups, alkoxycarbonyl groups, halogen groups, haloalkyl groups, haloalkoxy groups, heteroaryl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof, R1, R'1, R"1 independently comprise a C, a N, a O, a S, a H, —CH$_2$CH$_2$—, —CH=CH—, —C≡C—, —NH—, —NR—, —NH—NH—, —NH(CH$_2$)$_n$NH, —NR(CH$_2$)$_n$NR' 'NR—NR'—, —NH—O—, —NR—O—, —NH(CH$_2$)$_n$O—, —NR(CH$_2$)$_n$O—, —NH(CH$_2$)$_n$S—, —NR(CH$_2$)$_n$S—, —O(CH$_2$)$_n$O—, —O(CH$_2$)$_n$S—, —S(CH$_2$)$_n$S—, —CO—, —CO$_2$—, —COS—, —CONH—, —CONR—, —OC(O)NH—, —NHCONH—, —CONHCO—, —CO(CH$_2$)$_n$CO—, or combination thereof, X comprises a N, a O, a S or 2 Hs; R"6 comprises a C, a N, a O, a S, a H, —CH$_2$CH$_2$—, —CH=CH—, —C≡C—, —NH—, —NR—, —NH—NH—, —NH(CH$_2$)$_n$NH, —NR(CH$_2$)$_n$NR'— —NR—NR'—, —NH—O—, —NR—O—, —NH(CH$_2$)$_n$O—, —NR(CH$_2$)$_n$O—, —NH(CH$_2$)$_n$S—, —NR(CH$_2$)$_n$S—, —O(CH$_2$)$_n$O—, —O(CH$_2$)$_n$S—, —S(CH$_2$)$_n$S—, —CO—, —CO$_2$—, —COS—, —CONH—, —CONR—, —OC(O)NH—, —NHCONH—, —CONHCO—, —CO(CH$_2$)$_n$CO—, or combination thereof, "A" comprises an acetyl, Boc, 9-fluorenylmethyl carbamate, Cbz, Aloc, an amino acid, an amino acid analogue, an artificial amino acid, a dipeptide, a tripeptide, a tetrapeptide, a pentapeptide, a peptide sequence of between 2 and 30 amino acids that have greater than 50% homology to a portion of the GLP-1 sequence SEQ. ID.:1, a linker of 1-20 amino acids, a linker of an optionally substituted lower alkyl, a linker of an optionally substituted C1-C7 alkyl or a combination thereof, and "B" comprises an optionally substituted lower alkyl, an optionally substituted C1-C7 alkyl, an amino acid, an amino acid analogue, an artificial amino acid, a dipeptide, a tripeptide, a tetrapeptide, or a pentapeptide; a peptide sequence of between 2 and 30 amino acids that have greater than 50% homology to a portion of the GLP-1 sequence SEQ. ID.:1; a linker of 1-20 amino acids, C1-C7 alkyl or combination thereof, which may also be connected to one or more compounds M1 to M12 of FIG. 15, or 19A of FIG. 19.

One example includes a peptidomimetic compound having the formula:

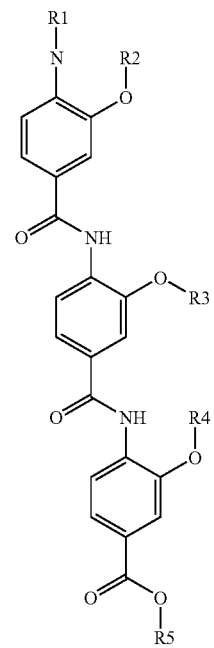

wherein R1, R2, R3, R4 and R5 individually comprise a C, a N, a O, a S, a H, one or more optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, carboxamido groups, carbamoyl groups, carboxyl groups, carbonyl groups, alkoxycarbonyl groups, halogen groups, haloalkyl groups, haloalkoxy groups, heteroaryl, heterocyclic ring, arylheterocyclic ring, heterocyclic compounds, amido, imido, guanidino, hydrazido, aminoxy, alkoxyamino, alkylamido, urea groups, carboxylic ester groups, thioethers groups, carboxylic acids, phosphoryl groups or combination thereof, an acetyl, a Boc (t-butoxycarbonyl), a Fmoc (9-fluorenylmethoxycarbonyl), a Cbz (benzyloxycarbonyl), an Aloc (allyloxycarbonyl), an amino acid, an amino acid analogue, an artificial amino acid, a dipeptide, a tripeptide, a tetrapeptide, a pentapeptide, a linker of 1-20 amino acids, a linker of an optionally substituted lower alkyl, a linker of an optionally substituted C1-C7 alkyl, a polycyclic aromatic substituted with a OH, a NH$_2$, a SH, a F, a Cl, a Br, a I, a NHR, a NRR', a guanidine (CN$_3$H$_4$), a N, a O, a S, a H, a peptide sequence of between 2 and 30 amino acids that has greater than 50% homology to a portion of the GLP-1 sequence SEQ. ID.: 1, a linker of 1-20 amino acids, an optionally substituted C1-C7 alkyl or a combination thereof, which may also be connected to one or more compounds M1 to M12 of FIG. 15 or 19A of FIG. 19. One specific example includes an R1 that is an acetyl group, R2 that is a benzyl group, R3 and R4 that are 4-fluorobenzyl groups, and R5 that is a methyl group; or where R1 is a t-butoxycarbonyl group, R2 is a methyl group, R3 is a benzyl group, R4 is a 2-naphthylmethyl group, and R5 is a methyl group.

GLP-1 has been found to be effective in lowering blood glucose in a broad range of diabetes states,[25] and remarkably, it does not induce hypoglycemia as insulin does.[26] It works through a membrane-bound GLP-1R on many organs, particularly on the pancreatic β-cells, and restores growth and function of β-cells. A GLP-1R agonist discovered from the saliva of the Gila Monster (i.e., exenatide; developed by Lilly and Amylin)[27-30] was approved by the FDA for the treatment of Type II diabetes[31]. Furthermore, a GLP-1 analogue containing a long fatty acid chain (i.e., liraglutide; developed by Novo Nordisk[32]) is currently in phase 3 clinical trials.

Despite the promising results shown by the GLP-1 agonists, these peptide therapeutics have two main limitations. GLP-1 has a very short half-life and is degraded by many enzymes in the serum, especially an ubiquitous enzyme dipeptidyl peptidase-IV (DPP-IV).[33-35] DPP-IV cleaves the N-terminal two residues of GLP-1 including $His^7$ which is critical for the biological action of this peptide. By this modification GLP-1 is converted into an inactive form which may even act as a receptor antagonist[36]. To prolong the half-life of GLP-1, a number of DPP-IV inhibitors have been developed and showed similar effects as exenatide with regard to blood glucose regulation. However, DPP-IV inhibitors do not appear to provide the same effect on gastric emptying and weight loss as are induced by GLP-1R agonists, and blocking this widely distributed enzyme may cause side effects during long-term use.[37,38]

Another problem of using GLP-1 and its peptide analogues as therapeutics is introduced by the peptidic structure and relatively high molecular weight of such compounds. Because of these issues, intravenous or subcutaneous injections are required since peptides are difficult to be formulated for oral delivery. Although intense research has been undertaken to deliver peptides via oral, transdermal or nasal routes, only limited success has been achieved.[24,39,40] In addition, the large peptidic structure of GLP-1 and its analogues sometimes causes an antibody formation against these molecules, which may prevent long-term clinical use.[41]

In contrast to successful precedents that have been reported for small peptides like somatostatin and enkephalins,[52,59] developing small molecule agonists to mimic larger peptide hormone interactions with cognate GPCRs has proven extremely difficult.[49,60,61] This issue applies particularly to class B GPCRs including the GLP-1R, a prototypical member of this receptor subgroup. As common features, class B GPCRs have large N-terminal chains and long extracellular loops which are believed to constitute multiple and well-separated binding pockets in the receptors to accommodate cognate large peptide ligands.[49,62,63] The present invention provides synthetic molecules which present the essential functionalities of corresponding peptide ligands in the proper three dimensional orientation that enables specific receptor interactions, leading to either stimulation or inhibition of receptor-mediated functions.

Peptidomimetics (also known as peptide mimetics) are small organic compounds which lack the peptide backbone of native peptides. Despite this modification, they still retain an ability to interact with corresponding receptors or enzymes by presenting essential chemical functionalities (i.e., pharmacophores) in characteristic three-dimensional patterns which are complimentary to the target proteins.[52,53] Thereby, peptidomimetics potentially combine the advantages of peptides (e.g., high efficacy and selectivity, low side effects) and small organic molecules (e.g., high enzymatic stability and oral bioavailability).

Small molecule agonists have been developed for class A and C GPCRs, however, small molecule agonists for class B GPCRs to which the GLP-1R belongs have not been identified prior to the present invention. Although many small molecules were discovered by screening chemical libraries, most of the reported compounds were found to be antagonists which block, rather than induce, signaling.[2,24,42-49] Although, two small molecule agonists for GLP-1R were reported recently,[50,51] these molecules appear to have a different pharmacological profile than GLP-1 due to their weak agonist activity. One of these compounds, a substituted quinoxaline does not compete with GLP-1 for receptor binding,[50] suggesting that it may induce receptor activation by a different mechanism compared to the endogenous peptide agonist. On the other hand, the other compound that has been reported, a substituted cyclobutane, appears be an orthosteric agonist and has been shown to be orally active.[51] However, latter type of molecules does not bear any structural similarity to GLP-1, and it will therefore be difficult to predict possible modifications for optimizing agonist activity.

Generally, despite their high efficacy, all these peptides have difficulty to be used in vivo since they are susceptible to rapid enzymatic degradation and not orally available. Whereas ligand screening approaches have led to the identification of synthetic small molecule agonists for many class A GPCRs, this strategy has proven much less successful when applied to class B receptors. In fact, non-peptide ligands identified by high-throughput screening for class B GPCRs show no functional activity and are thus classified as antagonists. They are even allosteric antagonists, not competing with endogenous peptides. Over the years, it was increasingly felt that the complex mechanism of action of endogenous peptide agonists at these class B GPCRs is difficult to be mimicked by such molecules that are typically found in screening libraries.

Structures of peptide ligands for class B GPCRs have been investigated by X-ray crystallography and NMR spectroscopy, and found to adopt α-helical structures. In addition, physiological significance of the α-helices in the peptides is also demonstrated by biophysical studies undertaken in the presence of receptors. To mimic α-helices, the present invention provides a new scaffold, oligo-benzamide, that is rigid in structure and place and orient substituents as an α-helix does. Substitution on the rigid tris-benzamide, for instance, allowed easy placement of three functional groups ($R_{1-3}$) corresponding to the side chains of amino acids found at the i, i+4, and i+7 positions of an ideal α-helix, representing one helical face as shown in FIG. 1. Furthermore, the present inventors have developed a facile synthetic route to prepare a number of tris-benzamides to represent α-helical segments of target proteins.

GLP-1 contains 30 amino acid residues and includes two helical segments that are connected by a linker region, in addition to a flexible N-terminal segment. The cognate receptor for this peptide has a long N-terminal chain and large extracellular loops, which together form multiple GLP-1 binding sites. The complexity of the receptor-ligand interactions is considered a likely reason why it has been difficult, if not impossible, to identify potent peptidomimetics for class B GPCRs by earlier screening campaigns using conventional small molecule libraries.

The present invention provides small molecule GLP-1 agonists that activate the GLP-1R selectively. Generally speaking, these compounds consist of one or two non-peptide modules which mimic α-helical segments of the template peptide in addition to organic linkers and extensions that are attached to the helical core modules. It is evident to individuals who are familiar with this field that compounds with the same general architecture can be similarly designed to mimic the function of other peptide receptor ligands that, like GLP-1, include one or two helical domains as essential structural features. In particular, this applies to peptides, which interact with other GPCRs within the class B family since it is well known that very similar principles of receptor-peptide ligand interactions apply as have been established for the GLP-1R. Like GLP-1, each of the corresponding peptide ligands includes a C-terminal and an N-terminal helical domain, wherein the ligand's C-terminus is primarily involved in receptor recognition and the N-terminus primarily triggers second messenger signaling. Class B GPCRs to which these general principles apply include, in addition to the GLP-1R, receptors for glucagon-like peptide-2 (GLP-2), calcitonin and calcitonin receptor-like peptide, corticotropin releasing factor (CRF), gastric inhibitory peptide (GIP), glucagon, growth-hormone releasing hormone (GHRH), parathyroid hormone (PTH), secretin, pituitary adenylate cyclase-activating peptide (PACAP), and vasoactive intestinal polypeptide (VIP). Cognate non-peptide agonists based on the structures disclosed in the current application may be therapeutically useful for the treatment of a broad range of diseases, including but not limited to osteoporosis (PTH receptors), diabetes (GIP receptors), inflammatory bowel disease and short bowel syndrome (GLP-2 receptors), and obesity (calcitonin and calcitonin receptor-like peptide, pituitary adenylate cyclase-activating peptide, and vasoactive intestinal polypeptide receptors).

Also, it is well known in the field that N-terminal truncations or minor sequence modifications of class B GPCR peptide ligands can convert respective ligands from agonists (stimulate receptor activity) to either antagonists (block ligand-induced function) or inverse agonists (attenuate basal, ligand-independent receptor activity). By inference, slight modifications in corresponding non-peptide mimetics (as disclosed here) will also lead to a corresponding functional conversion of bioactivity. For example, resulting antagonist generated by this approach would provide useful therapeutics for the treatment of obesity (GIP receptors), diabetes (glucagon receptors) and neuropsychiatric as well as inflammatory diseases (CRF receptors). Furthermore, resulting inverse agonists would be useful for the treatment of diseases that are triggered by naturally occurring constitutively active class B GPCR variants (e.g. dwarfism as a result of previously described PTH mutants that show ligand-independent signaling).

The present invention provides small molecule GLP-1 agonists that activate GLP-1R selectively. Additionally, present invention provides small molecules for other peptide hormones for class B GPCRs, e.g., GIP, PTH, secretin, glucagon, VIP, GLP-2, PACAP, GHRH, CRF, and calcitonin.

Although the structure of the GLP-1R (or of any class B GPCR) is not yet available, the conformation of GLP-1 (the corresponding agonist peptide) has been studied by 2D-NMR spectroscopy in a solution containing dodecylphosphocholine micelles to provide a membrane-like environment.[65,66] The 2D-NMR studies showed that GLP-1 has a highly helical structure containing two helical segments between residues 13-20 and 24-35, covering more than half of the peptide, and a linker region between residues 21-23. Although structures of peptides determined in solution are useful to speculate about receptor-bound conformations, the presence of receptor proteins can greatly influence peptide conformations upon binding. The highly sophisticated network of interactions between receptors and peptides cannot be mimicked properly by the simple structure of micelles.

To determine a receptor-bound conformation of a large peptide hormone, a positional cyclization scanning method is applied to obtain structural information when a peptide binds to its receptor.[64] The positional cyclization scanning method employs a series of conformationally restricted peptides and can uncover secondary structures in a receptor-bound conformation. Cyclization of the peptide fixes a defined secondary structure, and a sequential cyclization scan over the entire peptide sequence followed by receptor-binding analysis can survey the presence and location of secondary structure in this molecule. Only a cyclic peptide containing a correct secondary structure at the correct position will be recognized by a receptor with high binding affinity.

The conformational restrictions used in the method are a lactam bridge between $Lys^i$ and $Glu^{i+4}$ to form an α-helix, or a disulfide bridge between $Cys^i$ and $Cys^{i+5}$ to stabilize a β-turn.[67,70] Although the structural information obtained does not provide a picture in atomic resolution, it reflects a receptor-bound conformation which is quite difficult to obtain otherwise. A series of cyclic GLP-1 analogues containing lactam bridges between $Lys^i$ and $Glu^{i+4}$ were synthesized to validate the location of α-helices in a receptor-bound conformation of GLP-1. Alpha-helices stabilized between residues 16-21 and 24-34 are well recognized by the GLP-1R, whereas induction of α-helices near the N-terminus of GLP-1 (residues 11-15) and the putative linker region (residues 21-24) which connects the two helical segments caused poor binding affinity.

The results from the positional cyclization scanning study and a conformational analysis by NMR consistently indicate the presence of two separate α-helices in both the N-terminal regions and C-terminal regions of GLP-1, and these helices were therefore targeted to design GLP-1 peptidomimetics.

Figure 1B:
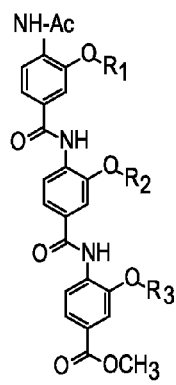
Figure 1C:
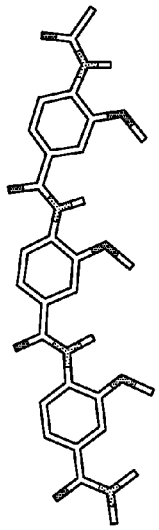
Figure 1D:
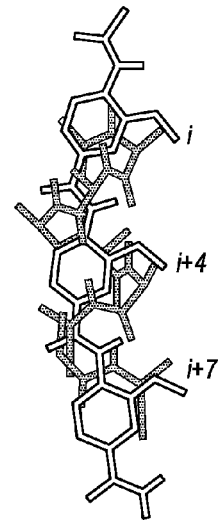
Figure 1E:
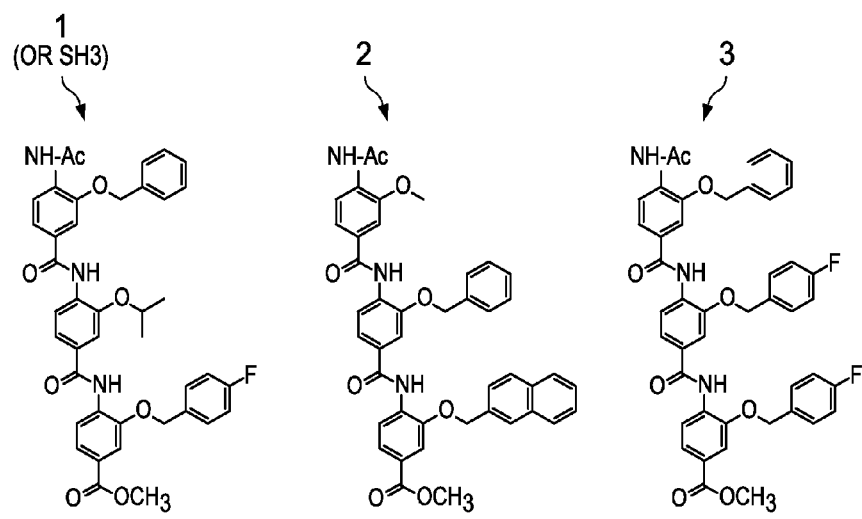

FIGS. 1A-1E are images of the structure of α-helix peptidomimetic compounds. FIG. 1A is an image of the structure of the α-helix peptidomimetic compounds, FIG. 1B is an image of the general structure of the α-helix peptidomimetic compounds, FIG. 1C is an image of the energy-minimized structure of an α-helix peptidomimetic compound, FIG. 1D is an image of the superimposition of the structure of an α-helix peptidomimetic (orange) with an α-helix (green), and FIG. 1E is an image of the structures of the α-helix peptidomimetic compounds 1, 2 and 3.

The present invention provides peptidomimetics representing the α-helices found in GLP-1 using an oligo-benzamide scaffold. As seen in FIG. 1B the substitution on the oligo-benzamide structure allows the placement of three functional groups corresponding to the amino acids at the i, i+4, and i+7 positions, representing one face of a helix as can be seen in FIG. 1A. The structure of the designed α-helix mimetic compounds was analyzed by molecular modeling using MacroModel[80] (version 9, Schrödinger, New York, N.Y.). A Monte Carlo conformational search was carried out (5,000 steps) using a MM3 force field[81] implemented into the software. The energy-minimized structure is seen in FIG. 1C and demonstrates that the three functional groups in the mimetic overlap well with the corresponding side chains of a helix seen in FIG. 1D.

Based on the positional cyclization scanning and NMR studies of GLP-1, two α-helix mimetic compounds of the present invention (e.g., the α-helix mimetic having structures 1 and 2) were designed to represent two hydrophobic helical faces located in the N-terminal and C-terminal regions of GLP-1. The N-terminal α-helix mimetic compound having structure 1 contains functional groups corresponding to the side chains of Phe[12], Val[16], and Tyr[19], while the C-terminal α-helix mimetic compound having structure 2 carries side chain groups corresponding to Ala[24], Phe[28] and Trp[31] (FIG. 1E).

The α-helix mimetic compounds were prepared in high yields and their ability to interact with the GLP-1R was evaluated. The α-helix mimetic compounds were dissolved in DMSO to prepare stock solutions with high concentrations (about 10 mM) with the goal of keeping the final DMSO concentration in the cell-based assays at 1% or lower. The effect of the DMSO solvent (1%) was evaluated separately and did not show any appreciable non-specific effects in biological assays.

HEK293 cells stably expressing human GLP-1 receptors were constructed and competitive receptor binding assays of the mimetics were carried out using $^{125}$I-exendin(9-39) as a radioligand.[47] Parallel studies using transiently transfected COS-7 cells expressing the human GLP-1R gave essentially identical results. In addition, cAMP production by the mimetics was determined by radioimmunoassay using the transfected HEK293 cells to examine agonistic activity. We have also engineered HEK293 cells to contain a multimerized cAMP responsive promoter linked to luciferase and beta galactosidase as well as the GLP-1 receptor.

Figure 2A:
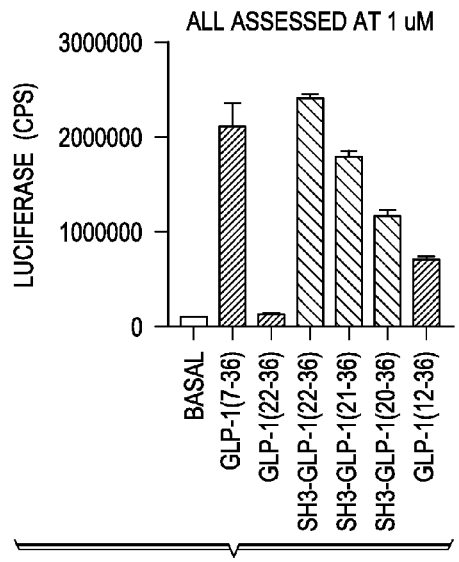
FIGS. 2A and 2B are graphs of the biological activity of the α-helix peptidomimetic compounds.
Figure 2B:
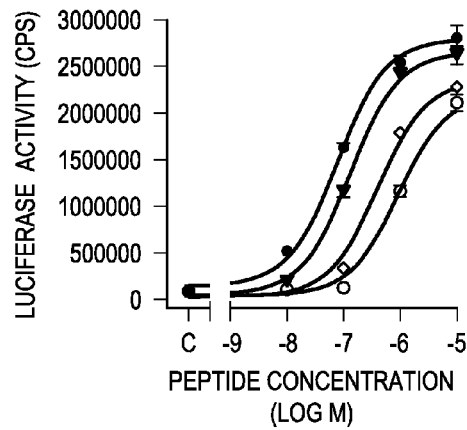
Figures 2, 18B:
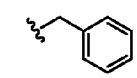
Figures 4, 18D:
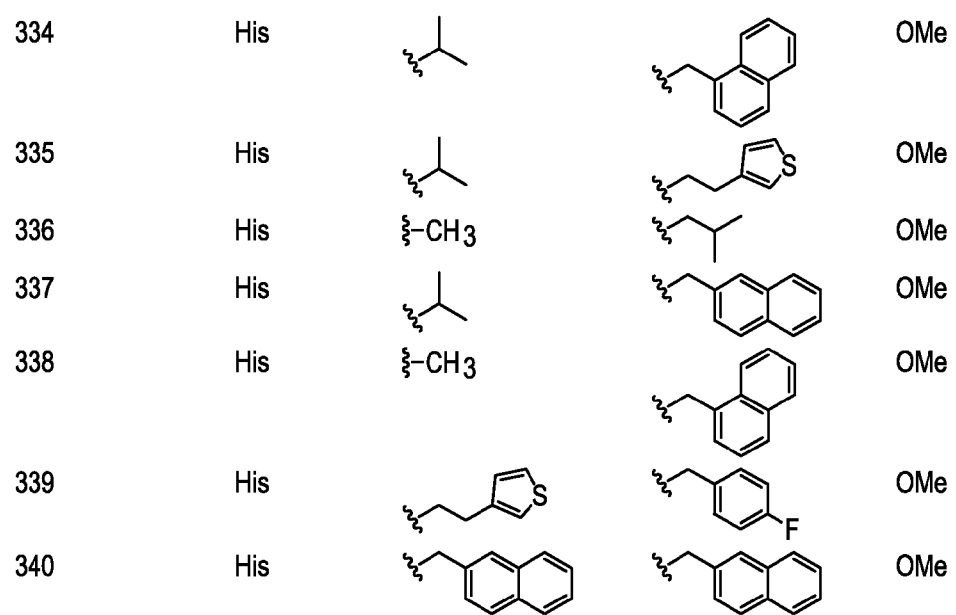
Figures 1, 18E:
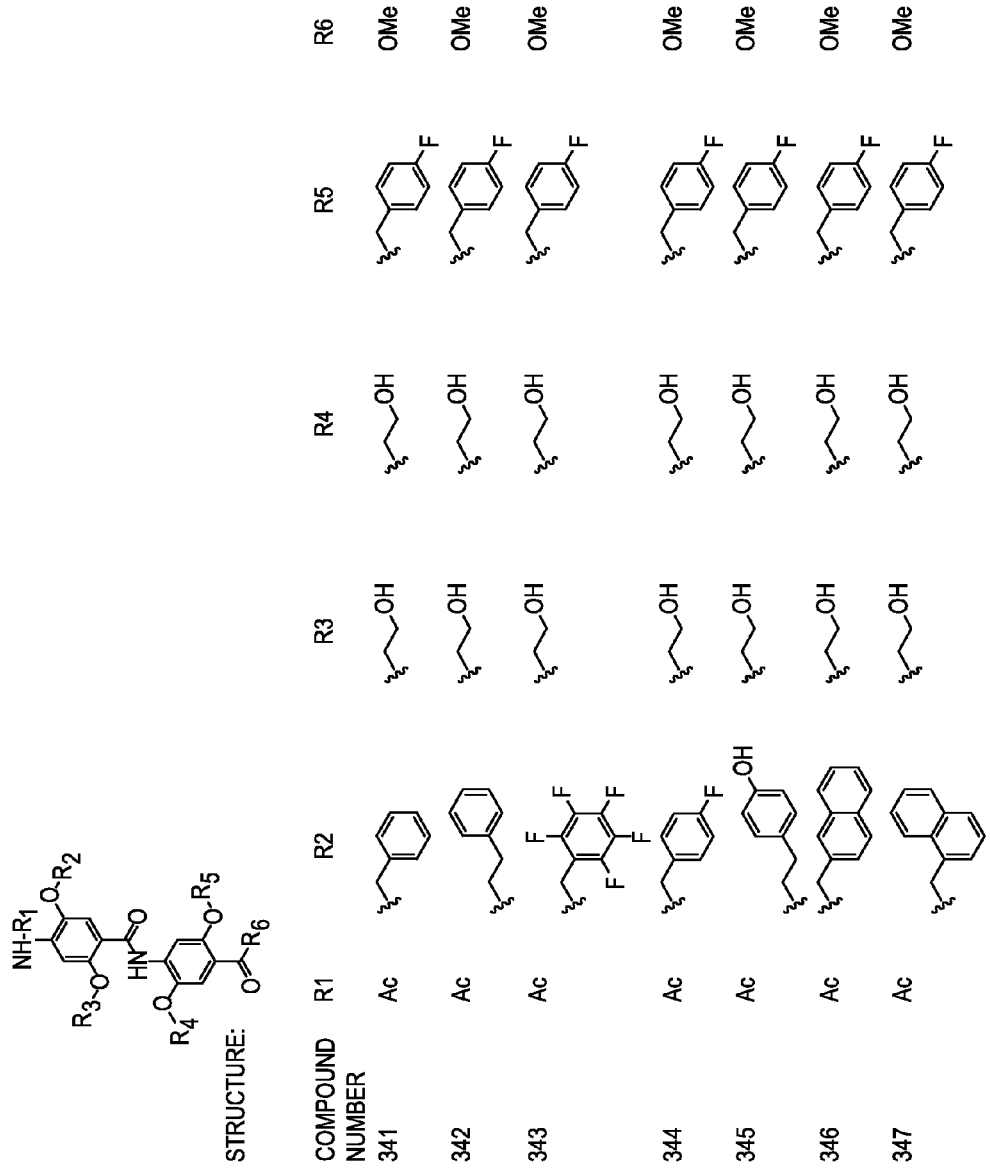
Figures 2, 18E:
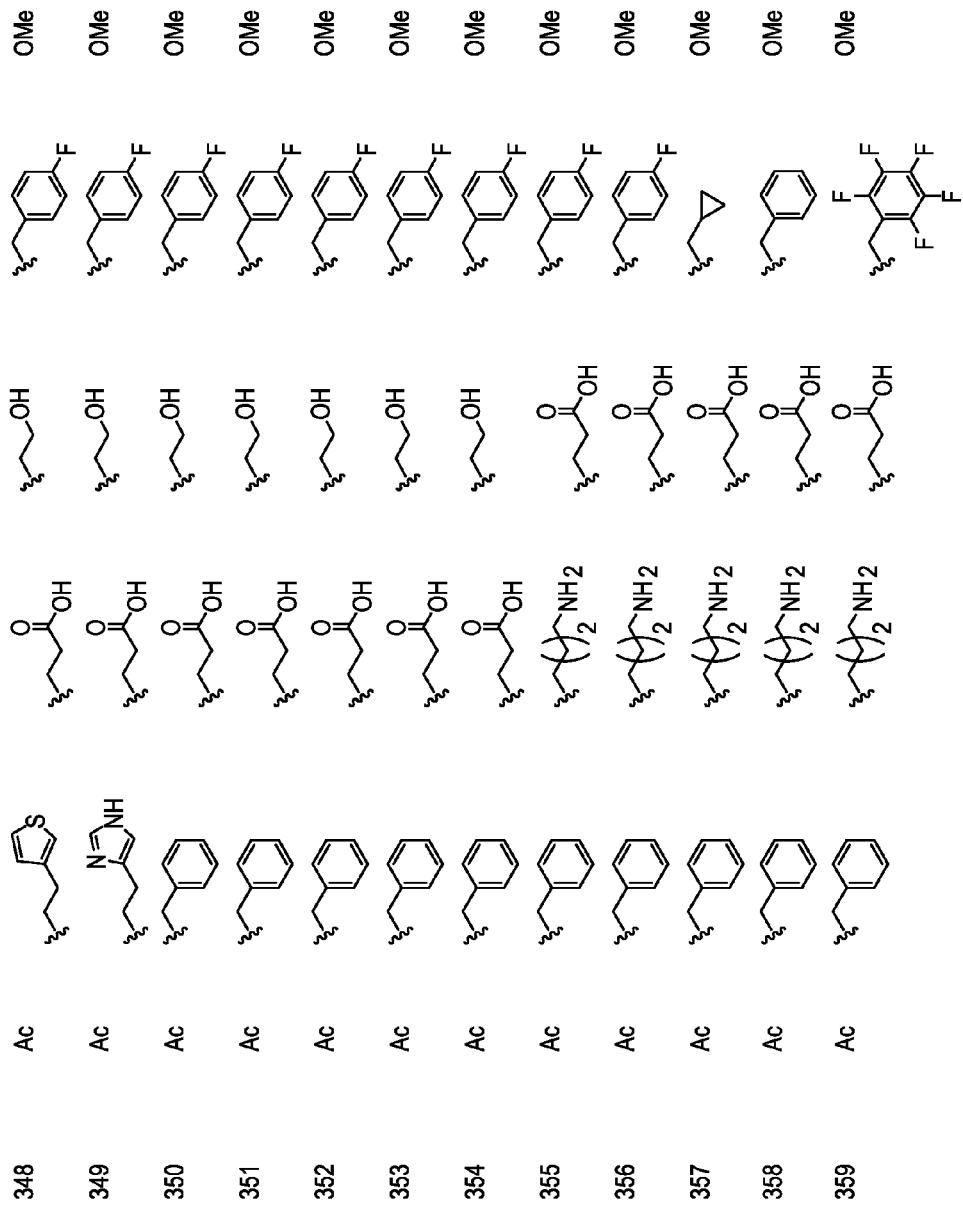

The present invention includes α-helix mimetics compounds and GLP-1 analogues containing them seen in FIG. 2, which stimulated receptor-mediated cAMP production and consequential luciferase activity, and are classified as agonists. FIGS. 2A and 2B are graphs of the biological activity of α-helix mimetic compound-containing GLP-1 analogues. FIG. 2A is a graph of several α-helix mimetic compound-containing GLP-1 analogues as well as control peptides (endogenous GLP-1 and fragments of GLP-1) at their concentration of 1 µM. FIG. 2B is a graph of the concentration-response curves of α-helix mimetic compound-containing GLP-1 analogues. It is notable that α-helix mimetic compounds (e.g., SH3) showed high potency especially when they are conjugated to GLP-1 fragments. It appears that different GLP-1 fragments used to connect the α-helix mimetic compound provided a range of potency ($EC_{50}$=134-965 nM). Furthermore, the activity of such mimetic-peptide conjugates were improved by incorporating a critical amino acid residue for GLP-1 function, His[7] ($EC_{50}$=78 nM).

This function appears to be specific since it could be blocked by a GLP-1R antagonist, exendin(9-39). Furthermore, no compound activity was detectable when assessed with untransfected HEK cells (i.e., lacking receptor expression). This observation further supports the conclusion that the mimetic compounds act as true GLP-1R agonists. The α-helix mimetic compounds were evaluated for selectivity using COS-7 cells expressing GLP-2 receptors, and did not show any cAMP production despite considerable sequence homology of the GLP-1 and GLP-2 receptors. This indicated that the mimetics are selective to the GLP-1R and that the α-helix mimetic compounds.

FIGS. 2A and 2B evaluates the α-helix mimicry of GLP-1 by examining the α-helix mimetic compound with structure 1. Several mimetic-peptide conjugates (SH3-GLP-1(22-36), SH3-GLP-1(21-36), and SH3-GLP-1(20-36) in FIG. 2) were created by substitution of a helical segment (residues 12-19) in GLP-1(12-36)-NH$_2$ with the α-helix mimetic having structure 1 (or SH3). In addition, two peptides, Ac-GLP-1(22-36)-NH$_2$ and Ac-GLP-1(12-36)-NH$_2$ were also prepared to serve as controls. The binding affinities of the α-helix mimetic-containing GLP-1 analogues are higher than that of the short control peptide, Ac-GLP-1(22-36)-NH$_2$. This is explained by the fact that the mimetic-peptide conjugates include additional functional groups found in the helical segment corresponding to GLP-1 residues 12-19, where attachment of the α-helix mimetic compound having structure 1 mimics the corresponding helical segment. In luciferase reporter assay, the $EC_{50}$ of the mimetic-peptide conjugate (SH3-GLP-1(22-36)) was determined to be 134 nM. These findings indicate that the α-helix mimetics using the oligo-benzamide scaffold can successfully mimic the helical segment of a template peptide. Furthermore, addition of the critical amino acid for GLP-1 function, His[7], improved the potency ($EC_{50}$=78 nM).

Figure 3A:
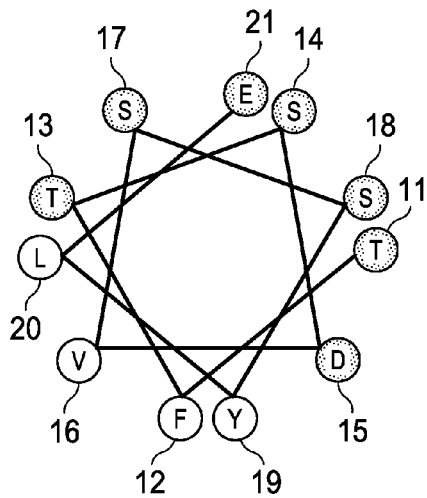
FIGS. 3A and 3B are helix wheel plots of the residues in GLP-1.
Figure 3B:
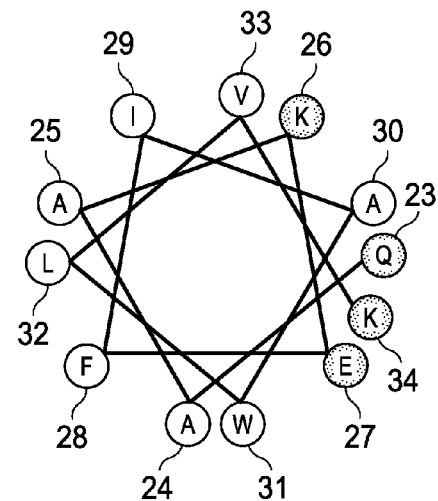

FIGS. 3A and 3B are helix wheel plots of the residues in GLP-1. FIG. 3A is a helix wheel plot of the N-terminal and FIG. 3B is a helix wheel plot of the C-terminal helices in GLP-1, with the hydrophobic residues shown in white whereas hydrophilic ones are shown in grey.

The present invention provides a non-peptide α-helix mimetic compound with GLP-1 agonist activity.[82] The α-helix has a large surface area with multiple faces created by different sets of residues, whereas the mimetic compounds 1 and 2 discussed above represent only two of these helical faces. A helical wheel plot was used to visualize the amphiphilic helical faces in GLP-1 thereby guiding the design of the α-helical mimetic compounds. Based on the results from the positional cyclization scanning and the NMR studies, the two helical sections, one in the N-terminal and the other in the C-terminal region of GLP-1 (corresponding to residues 11-20 and 23-34, respectively; see FIG. 3) were selected for mimicry by non-peptide molecules.

As reflected by the helix wheel plots in FIGS. 3A and 3B, an ideal α-helix consists of 3.6 residues per complete turn and the angle between two residues in the drawing is therefore chosen to be 100°. Although the helices in GLP-1 may slightly deviate from the ideal α-helical structure, these plots can readily show amino acids on the same helical face and should thus be targeted to design appropriate α-helix mimetic compound for GLP-1. The plots demonstrate the amphiphilicity of the helices in GLP-1 and the hydrophobic and hydrophilic faces that are to be reiterated in the mimetic compounds.

Figure 4:
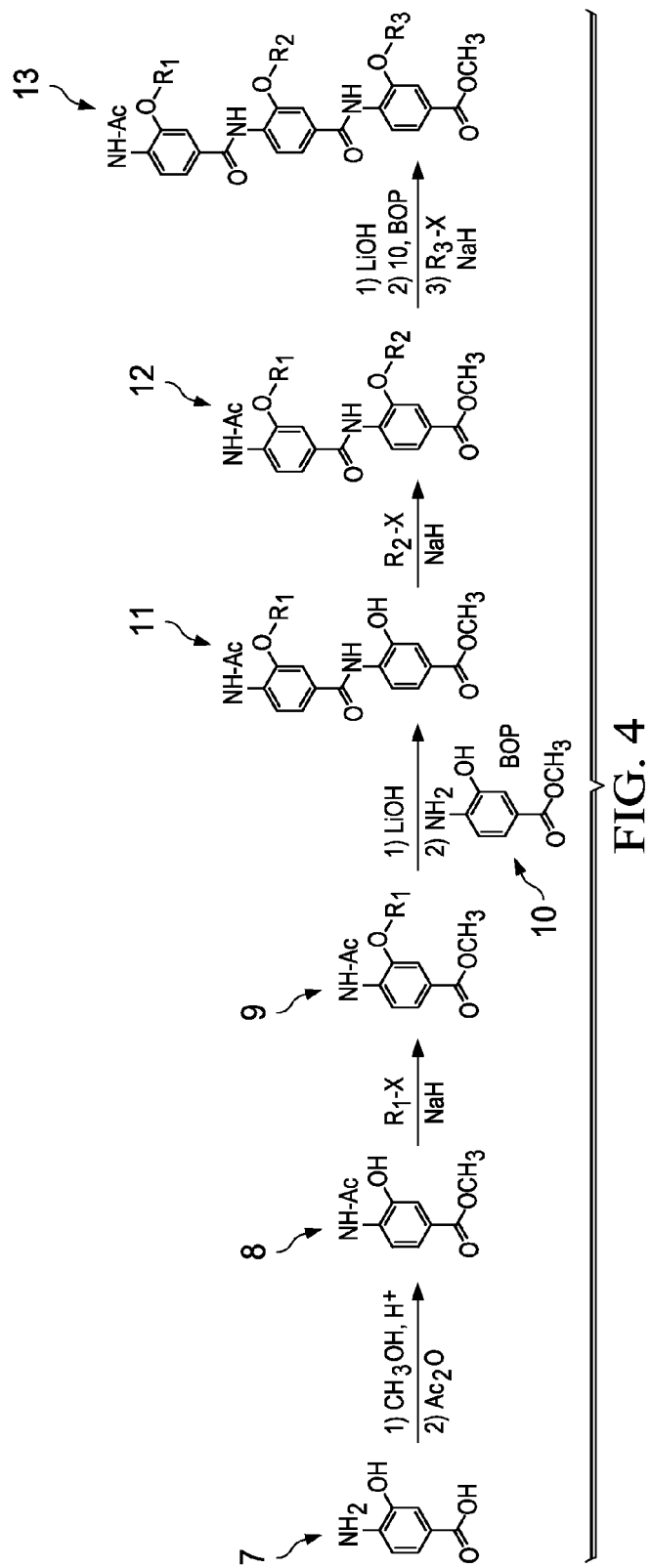
FIG. 4 is a synthesis scheme for the preparation of peptidomimetic compounds of the present invention that represent one α-helical face of a peptide.

FIG. 4 is a synthesis scheme to prepare α-helix mimetic compounds of the present invention. For example, fifteen α-helix mimetic compounds were made starting with a 4-amino-3-hydroxybenzoic acid compound 7, which was converted to an N—Ac protected methyl ester compound 8. Various alkyl groups were introduced to the hydroxyl group using a variety of alkyl halides and a base (like NaH) known to the skilled artisan. After the alkylation reaction, the methyl ester compound 9 was hydrolyzed using LiOH, and methyl 4-amino-3-hydroxybenzoate compound 10 was coupled to the free benzoic acid using a coupling reagent (like BOP), resulting in a benzamide compound II containing one alkyl group corresponding to the i position of a helix. These steps were repeated to synthesize oligo-benzamide compounds.

Figures 5A, 5B:
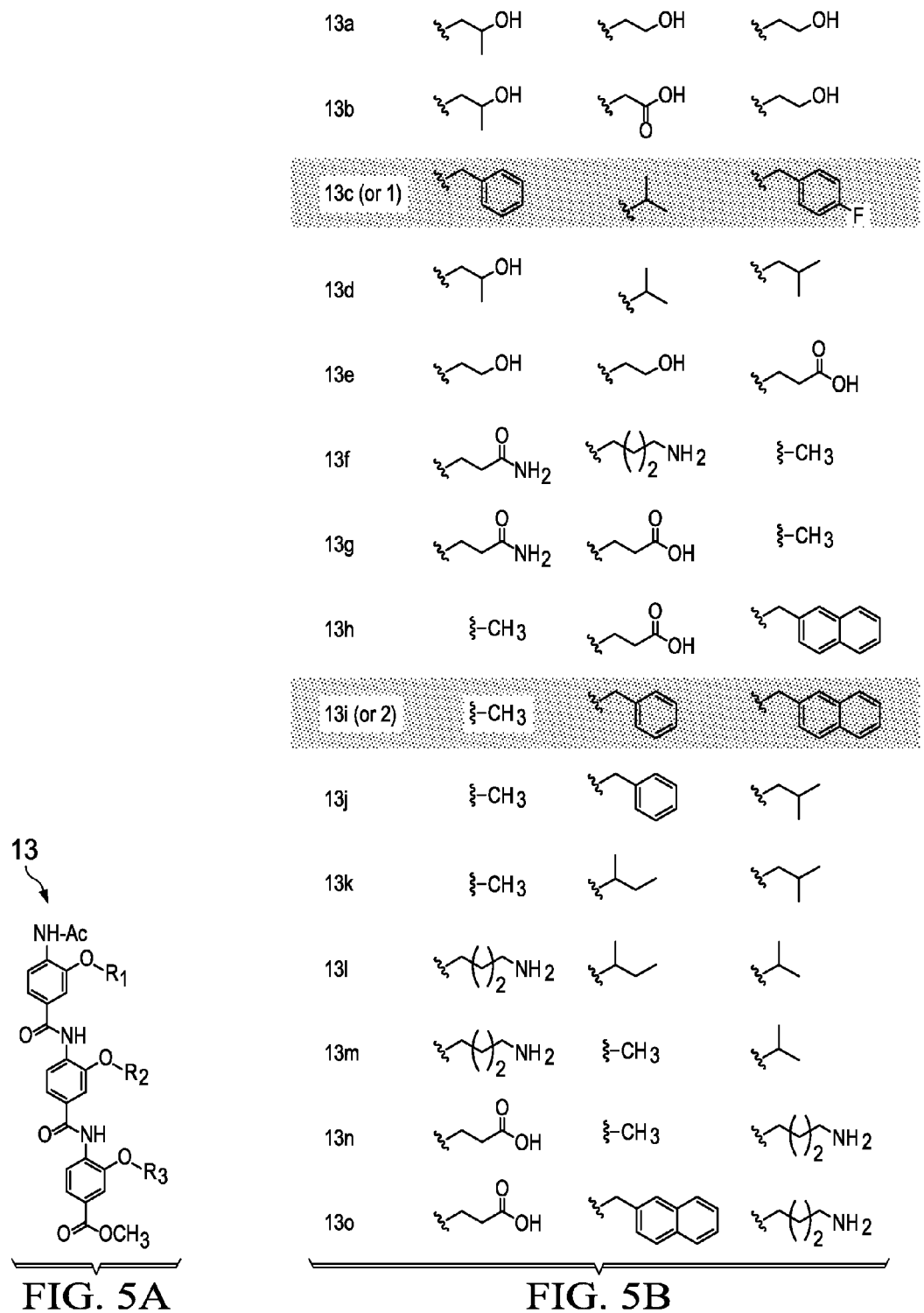
FIGS. 5A and 5B are images that illustrate various additional peptidomimetic compounds of the present invention that represent one α-helical face of a peptide.

FIGS. 5A and 5B are images that illustrate various α-helix mimetic compounds of the present invention. FIG. 5A provides the basic structure indicating the modification locations R1, R2 and R3, which may be substituted with various groups to provide different characteristics. For example, FIG. 5B is a table of the substitutions at R1, R2 and R3 and provides the structures of the α-helix mimetic compounds 13A-13O. The alkylation and coupling reactions were repeated to place two other functional groups corresponding to the i+3 (or i+4) and i+7 positions, to prepare the α-helix mimetic compounds 13A-13O.

Given an α-helix has 3.6 residues per turn, the amino acids on the same helical face are at the i, i+3 (or i+4) and i+7 positions. By considering this spatial arrangement given by the α-helix mimetic compound 13, five α-helix mimetic compounds can be designed from the N-terminal helical segment and ten α-helix mimetic compounds can be designed from the C-terminal helical segment as seen in FIG. 5B.

The synthesized α-helix mimetic compounds were evaluated by receptor-binding, cAMP production, and luciferase reporter assays. The α-helix mimetic compounds were dissolved in DMSO to prepare stock solutions. Stably transfected HEK cells (or transiently transfected COS cells) expressing human GLP-1 receptors were used for competitive receptor-binding assays using $^{125}$I-exendin(9-39) as a radioligand.[47] cAMP production by the α-helix mimetic compounds was determined by radioimmunoassay using the transfected HEK cells (or COS cells) to identify agonists. And, luciferase activity was measured to examine receptor activation function by agonists. To evaluate selectivity for the GLP-1R, the α-helix mimetic compounds were tested with GLP-2 and glucagon receptors expressed on transfected cells. The capability of the α-helix mimetic compounds to properly mimic corresponding helical segments were examined by preparing mimetic-peptide conjugates in which one or both helical segments are replaced by α-helix mimetics.

Figures 3, 18E:
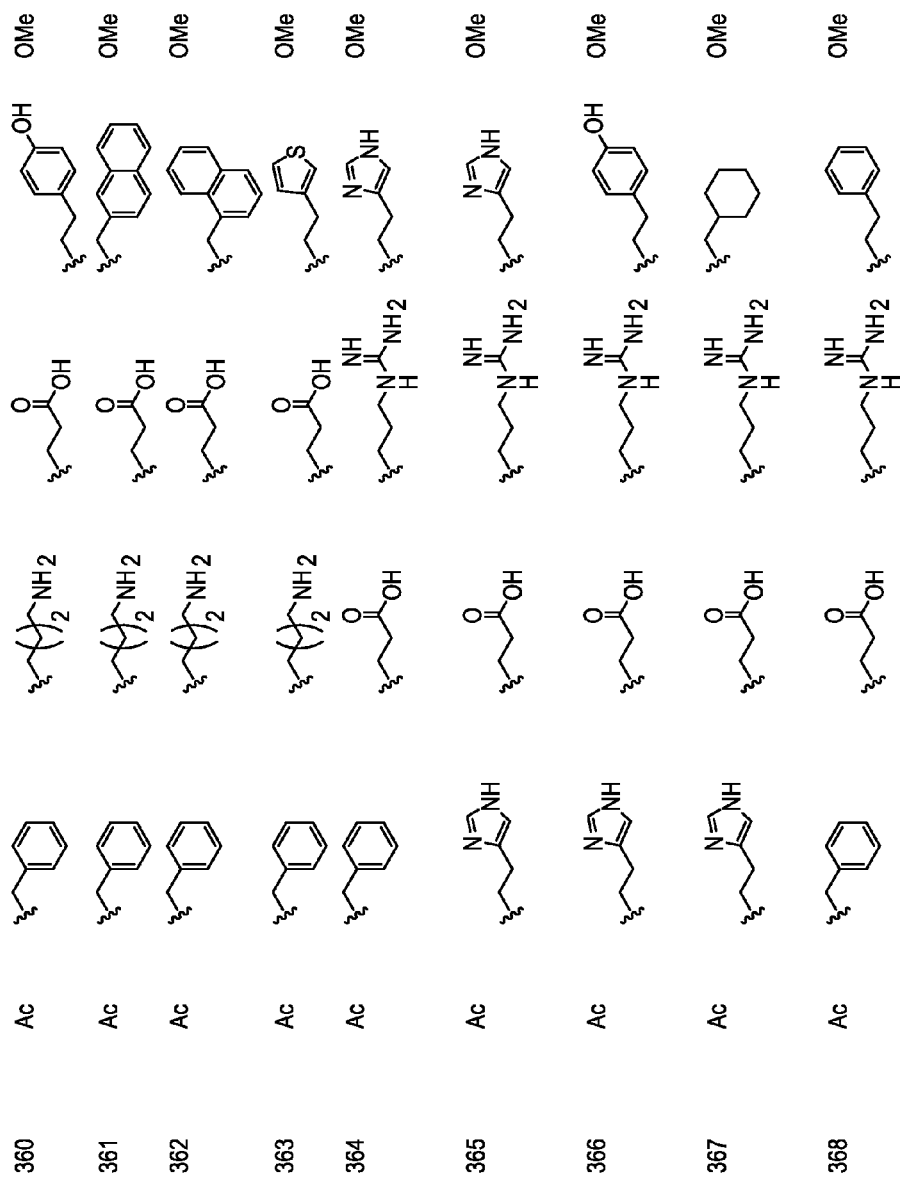
Figures 4, 18E:
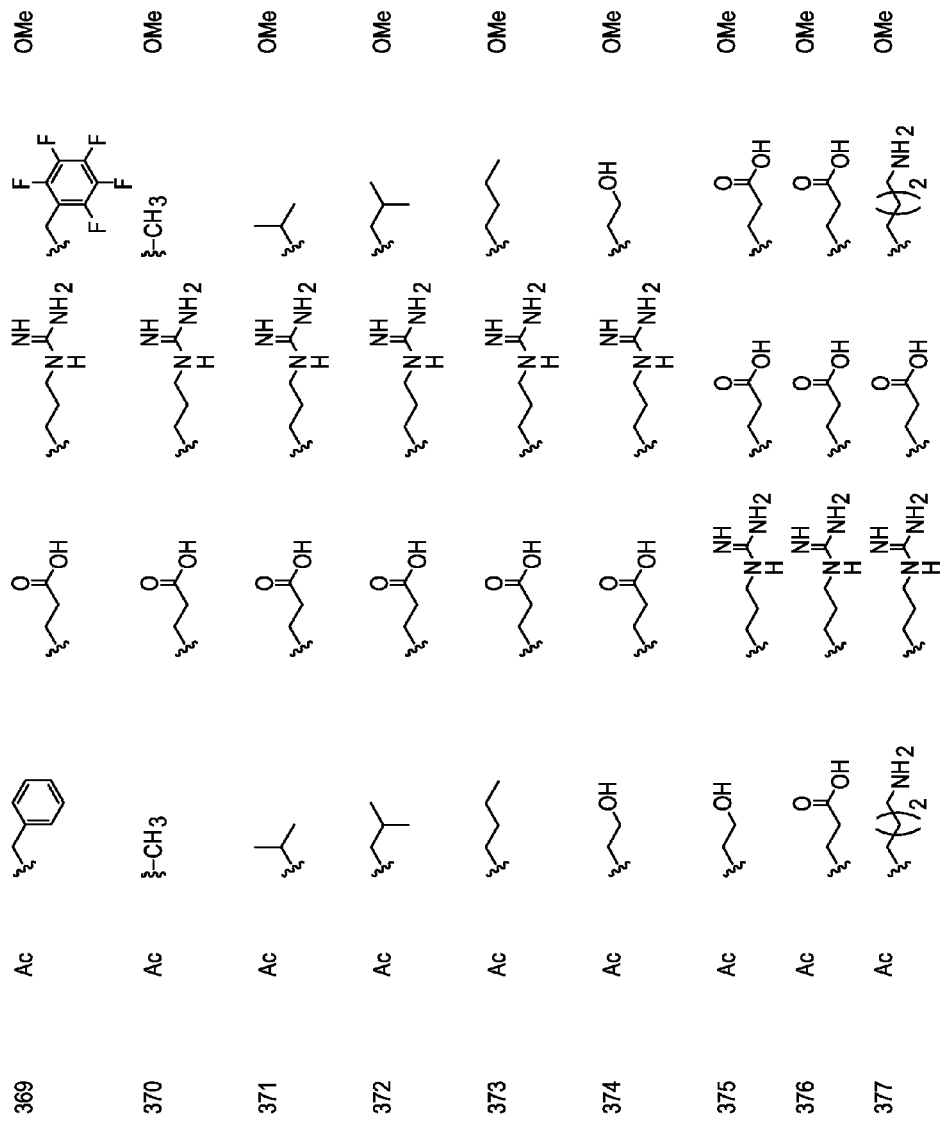
Figures 5, 18E:
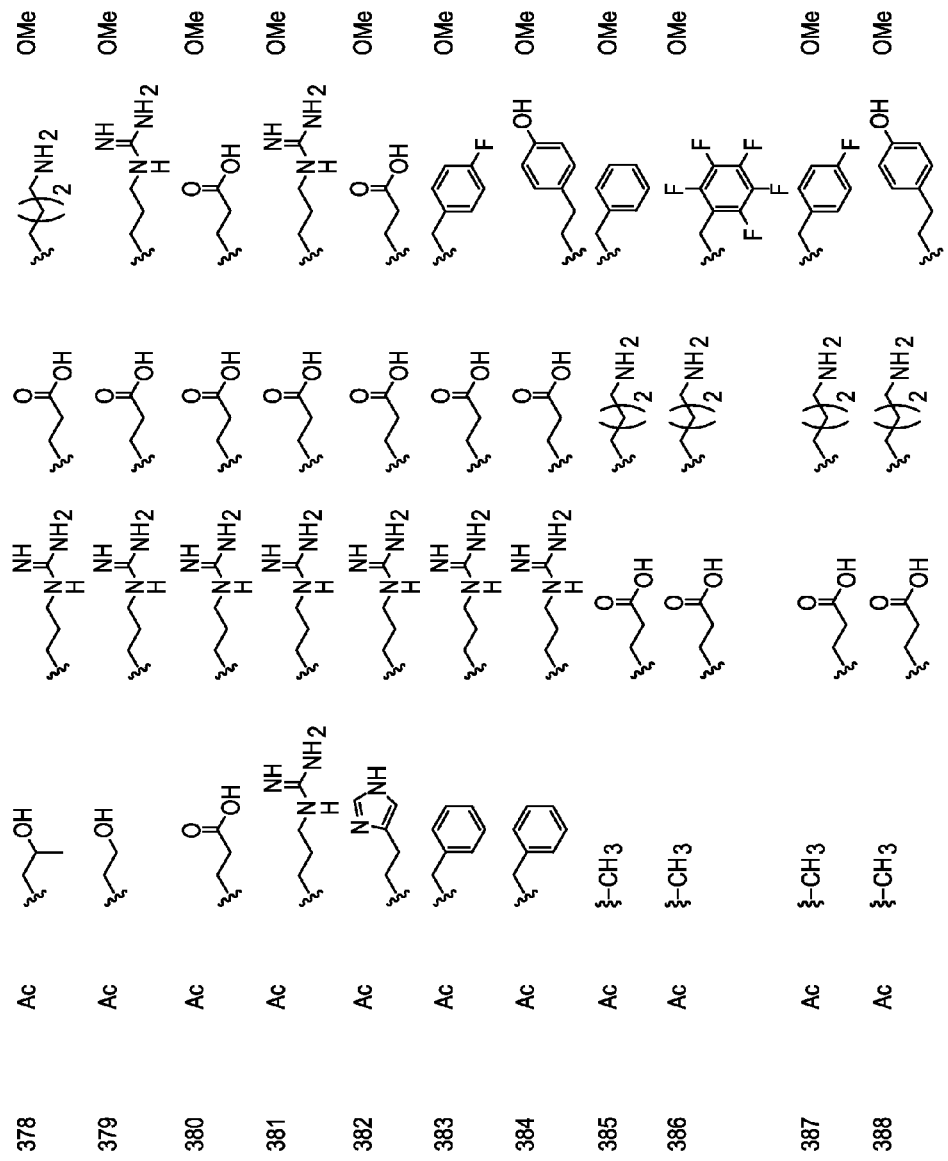
Figures 6, 18E:
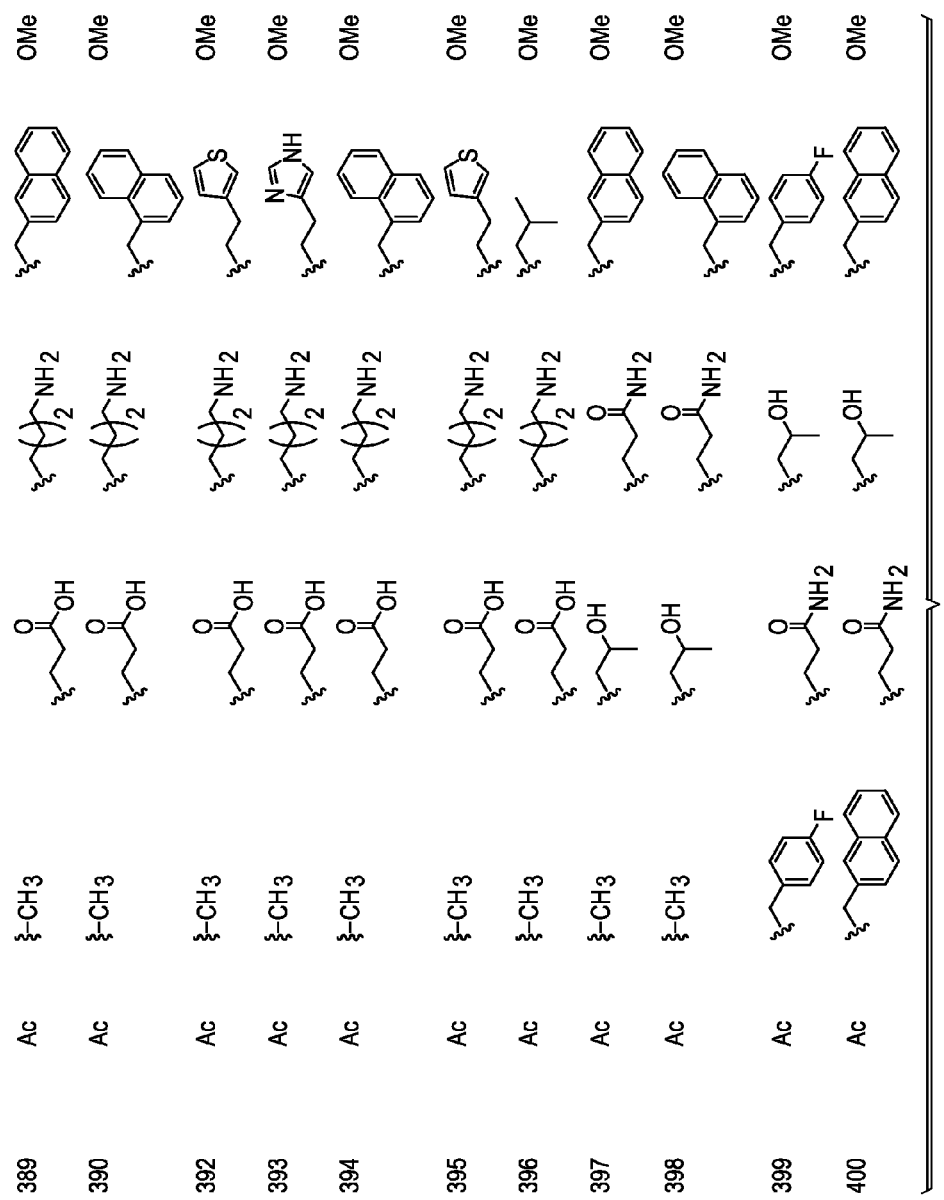
Figures 1, 18F:
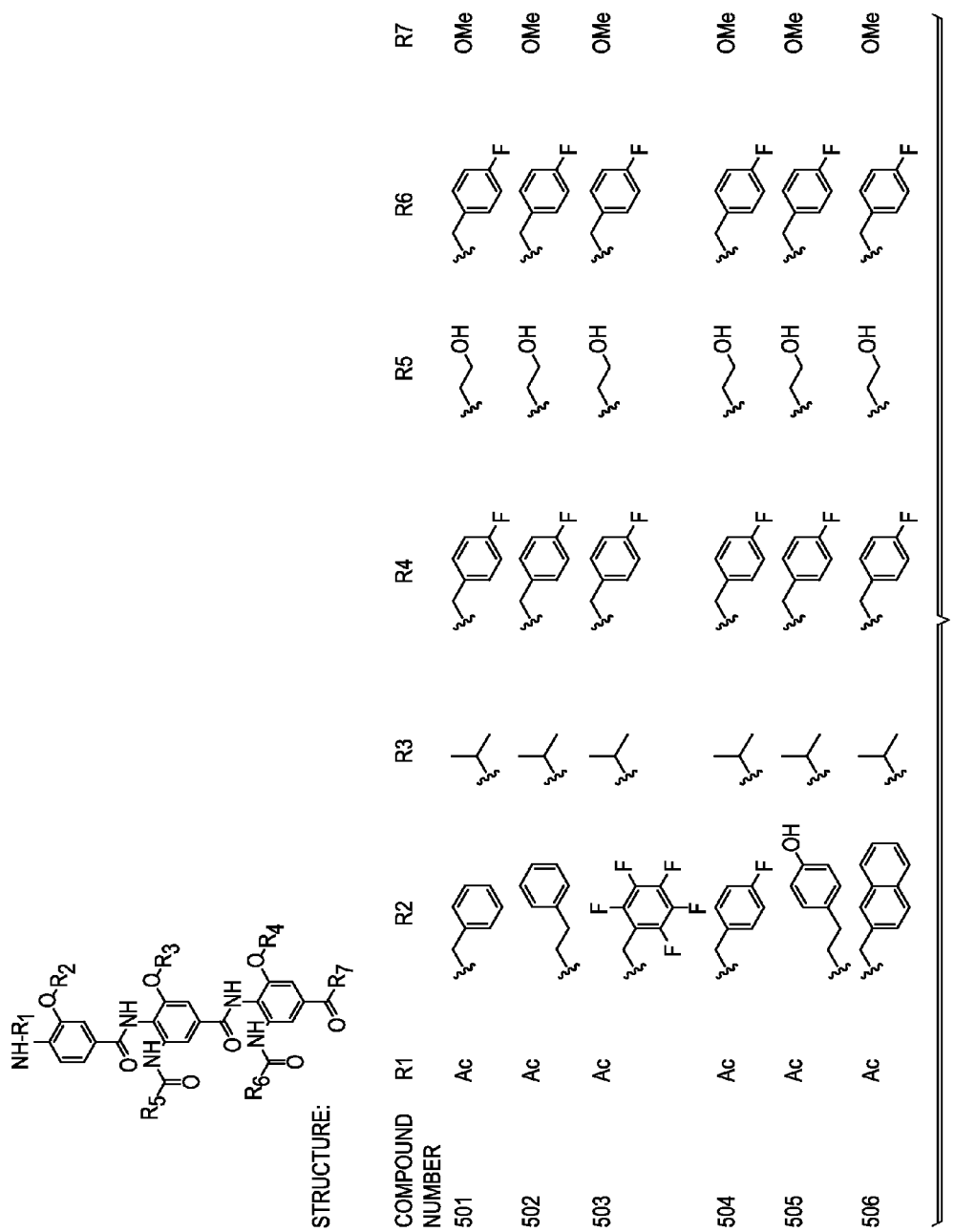
Figures 2, 18F:
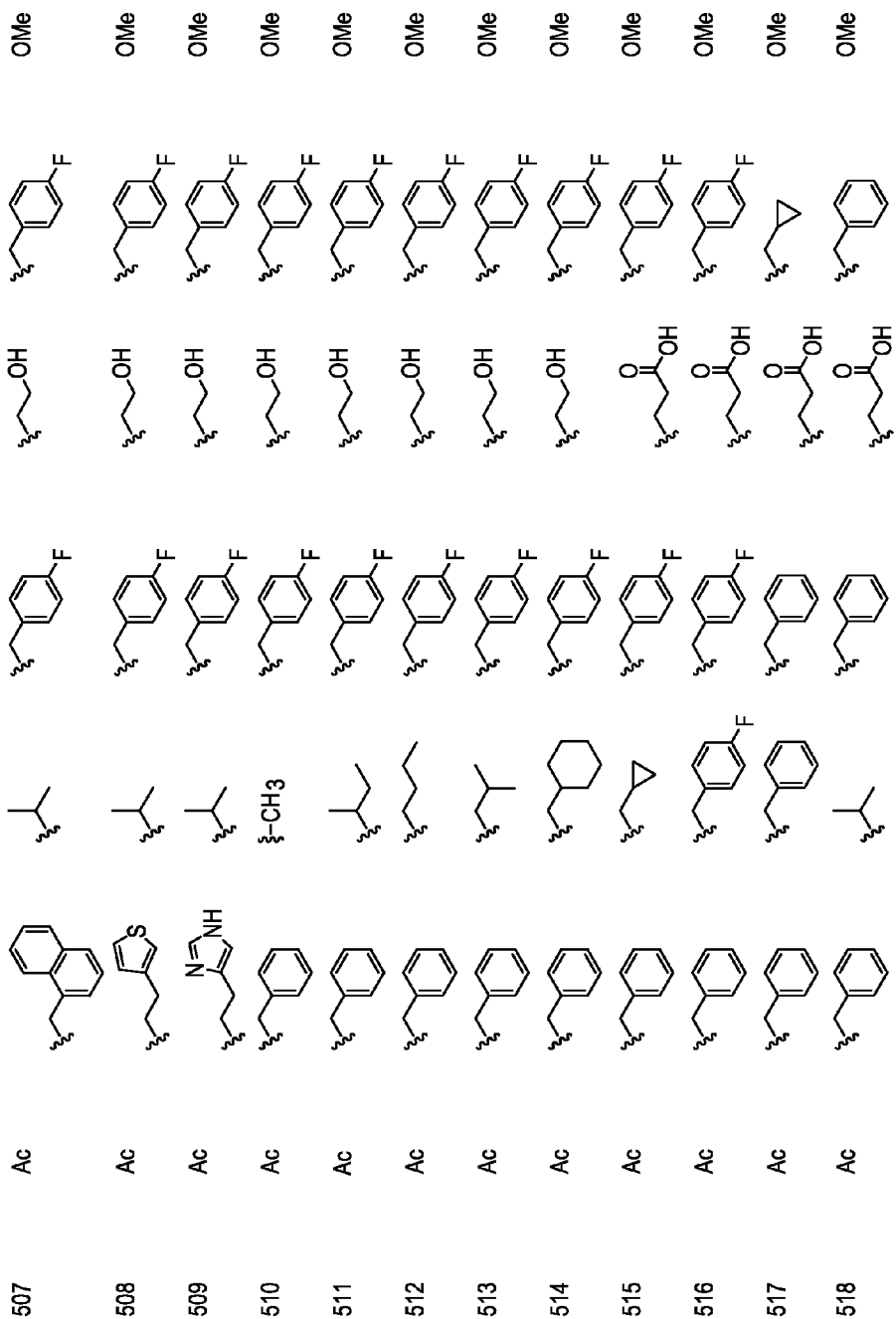
Figures 3, 18F:
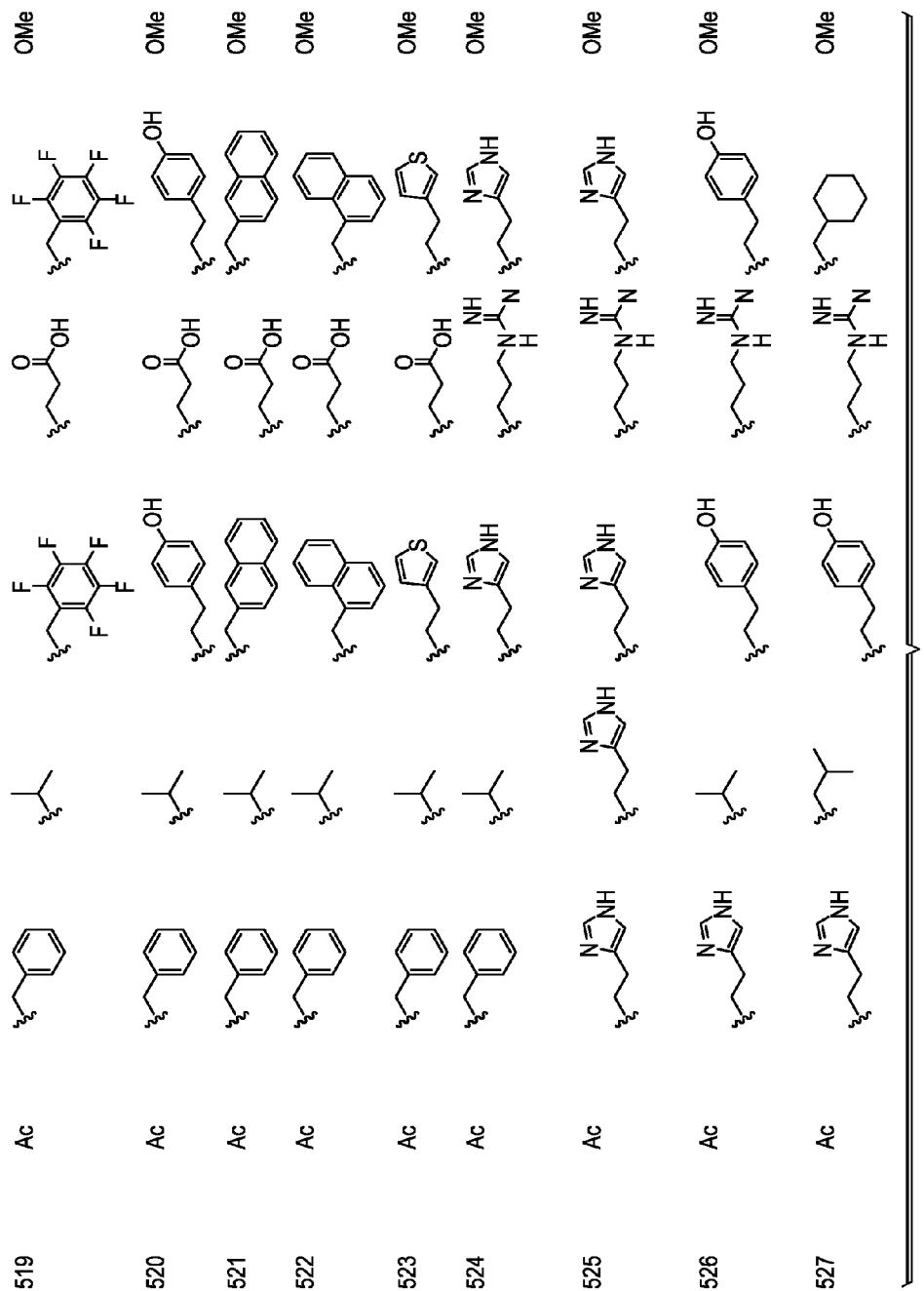
Figures 4, 18F:
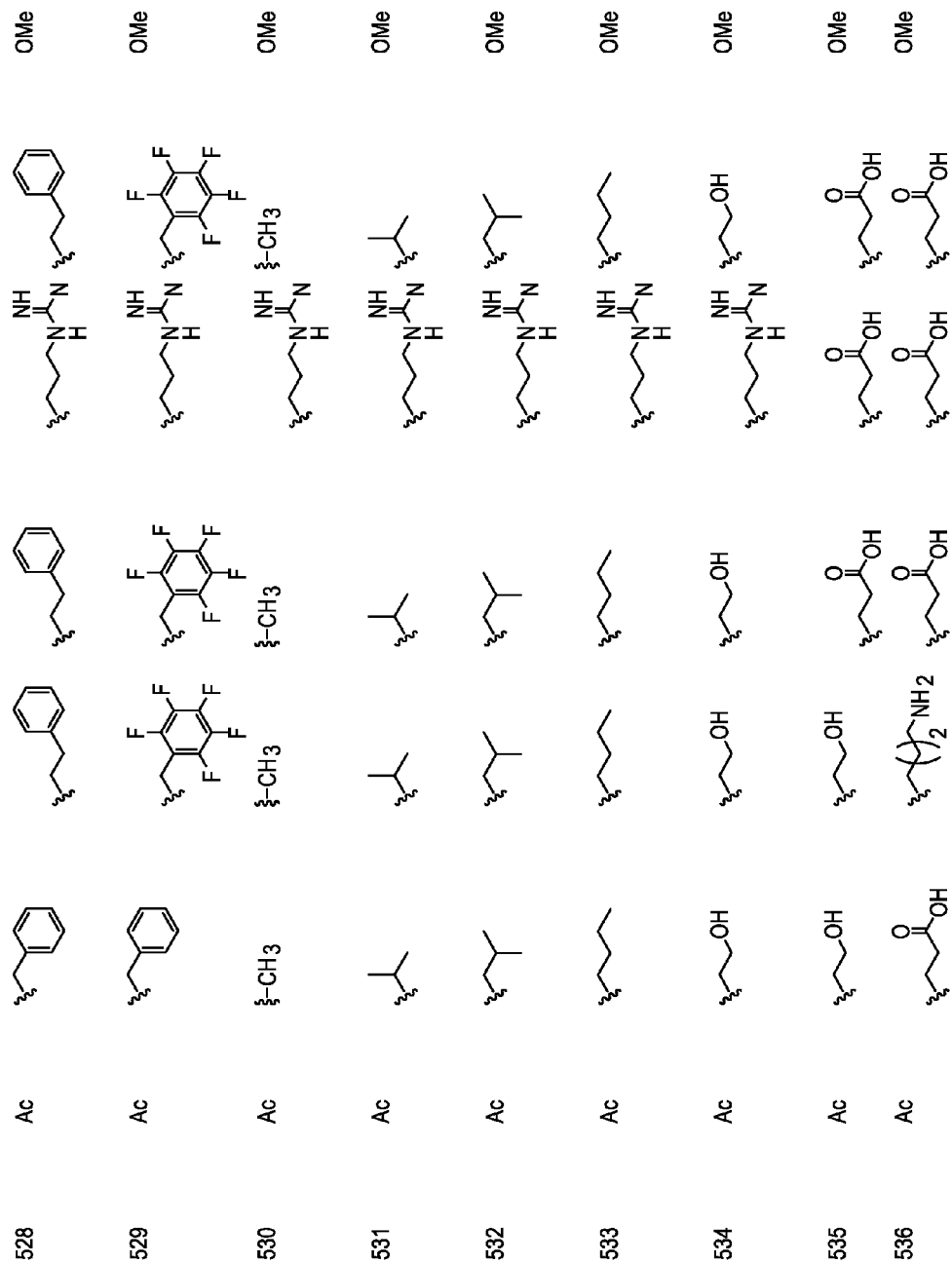
Figures 5, 18F:
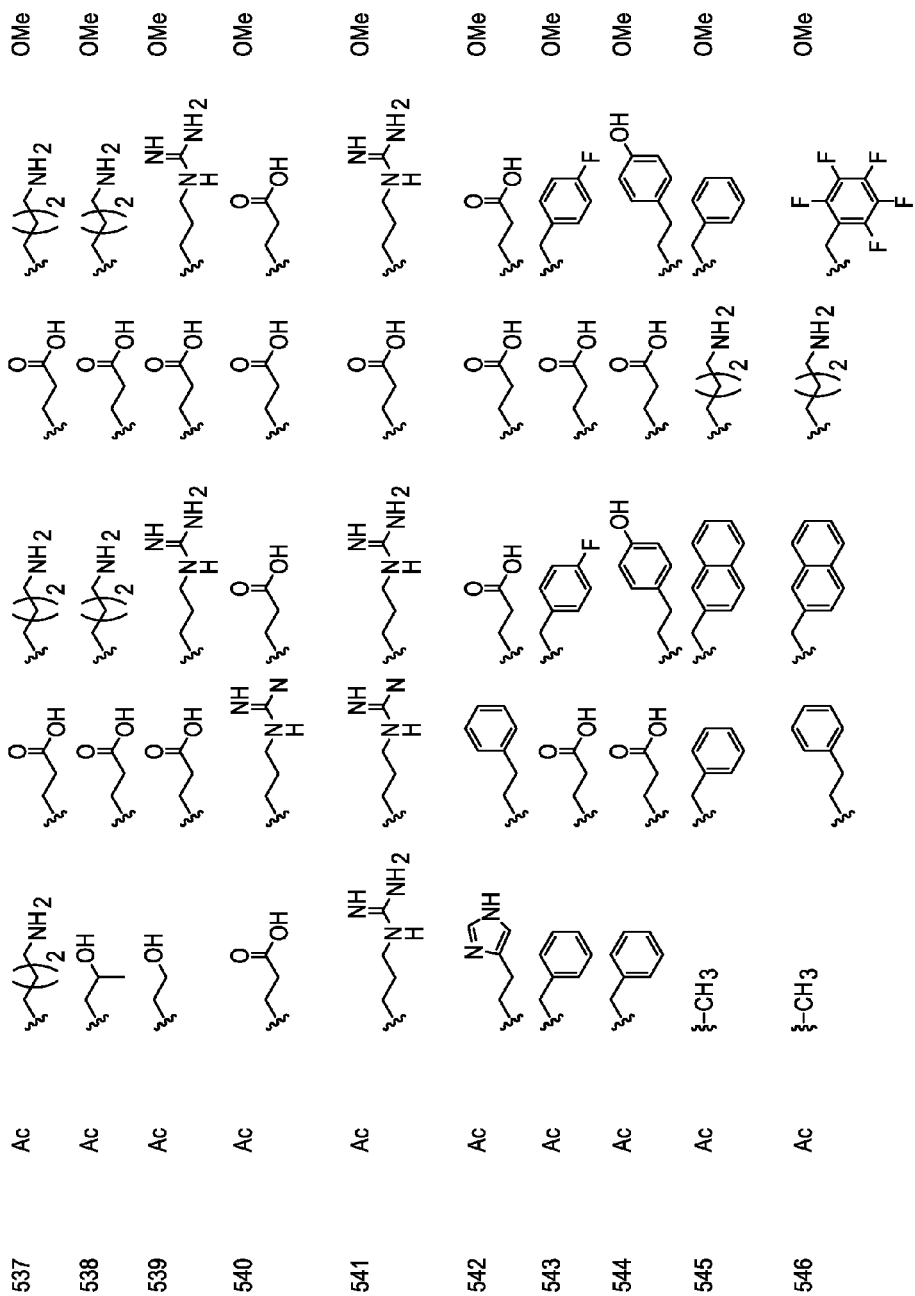
Figures 6, 18F:
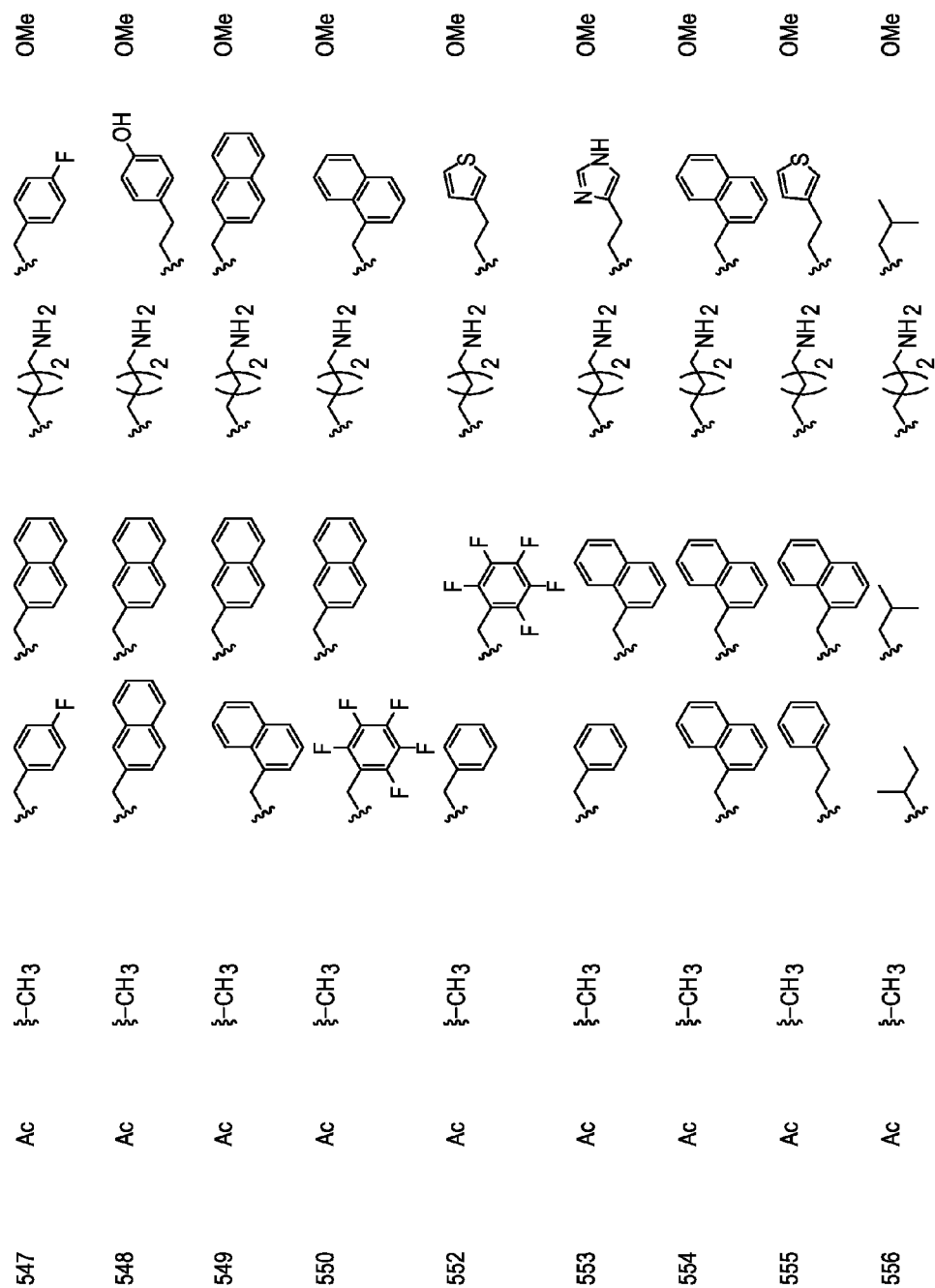
Figures 7, 18F:
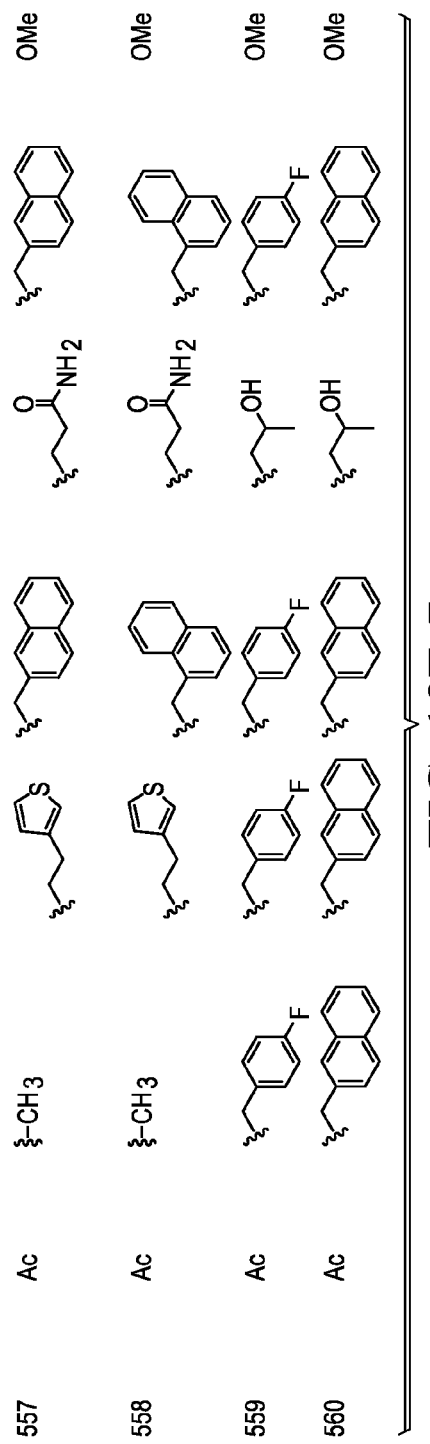
Figures 1, 18G:
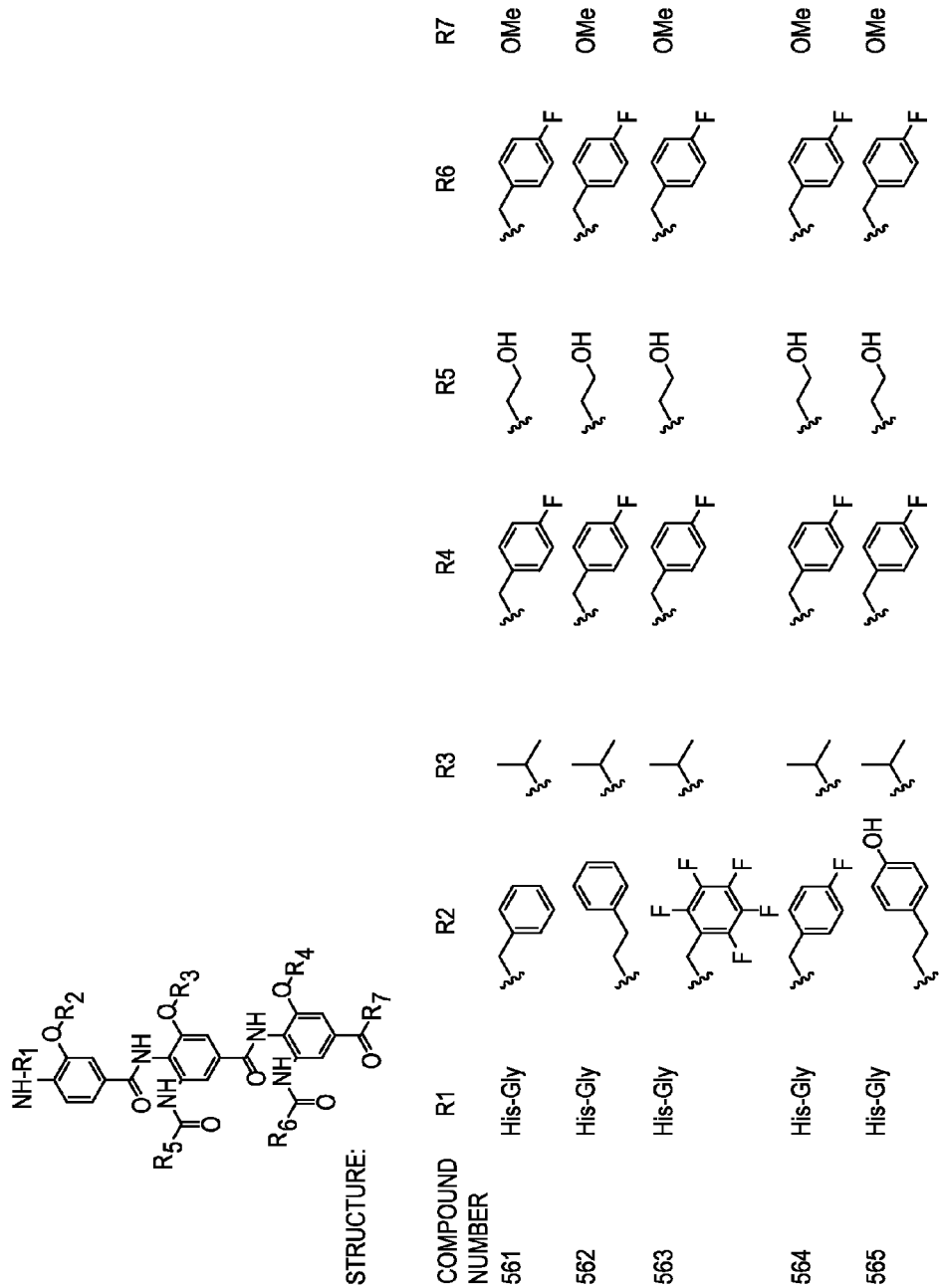
Figures 2, 18G:
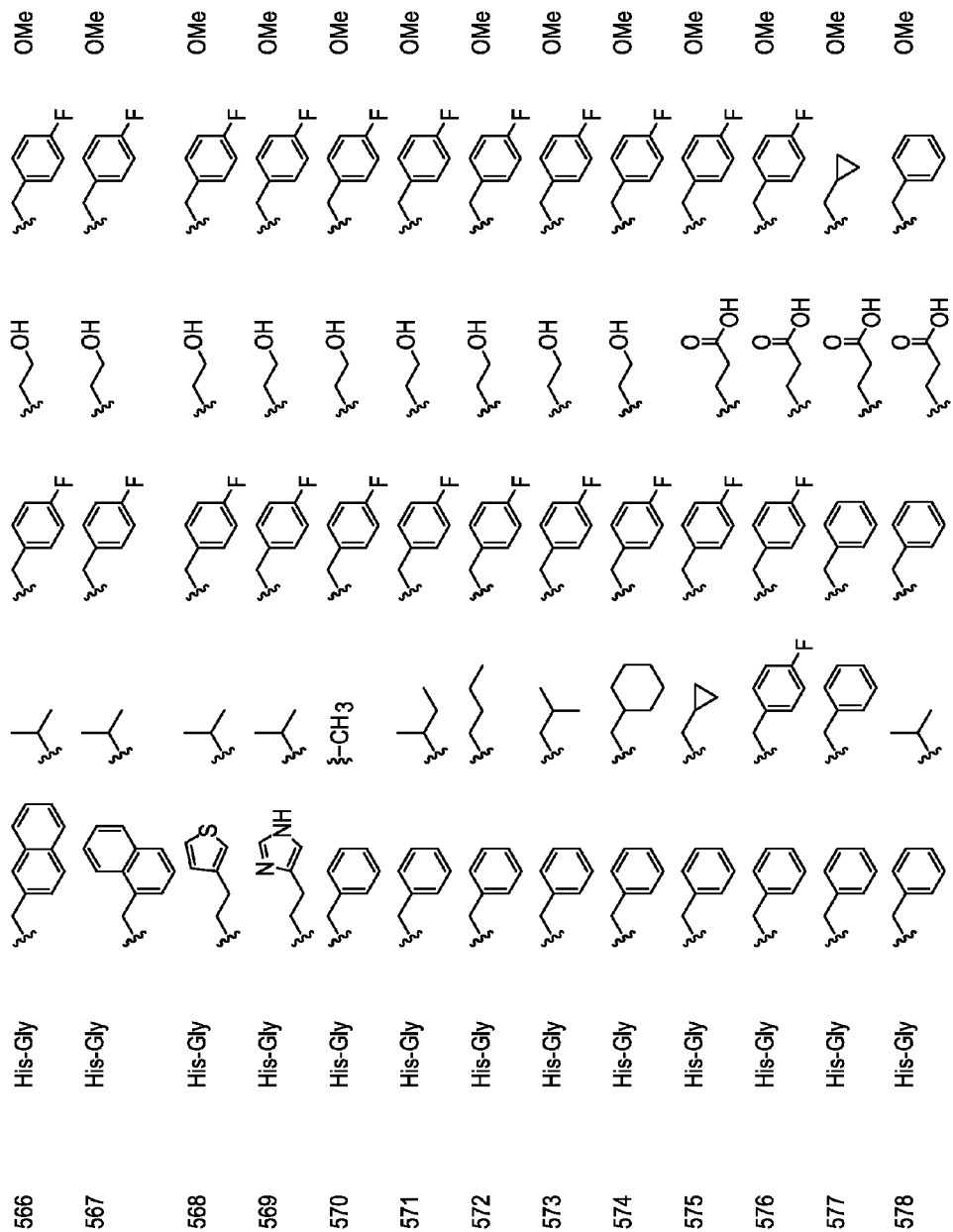
Figures 3, 18G:
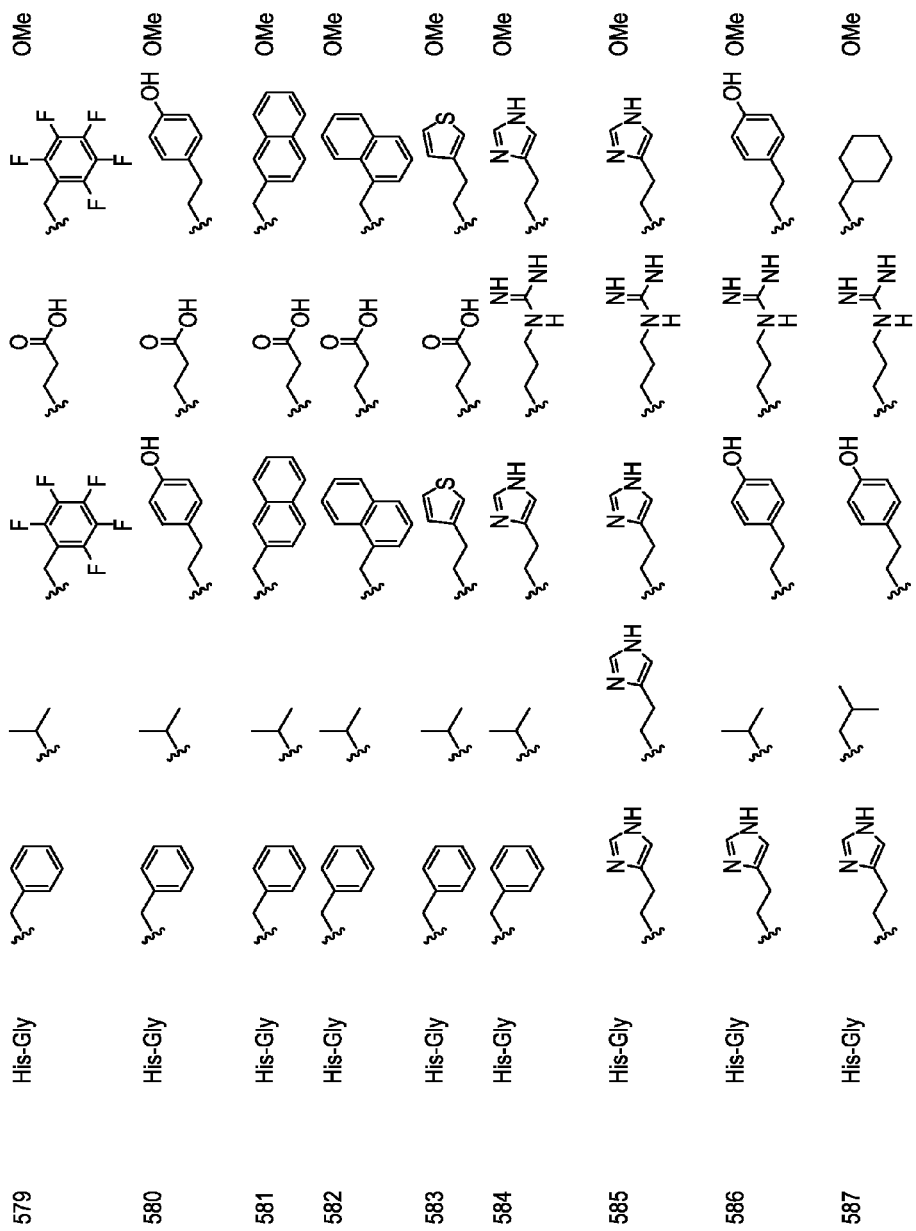
Figures 4, 18G:
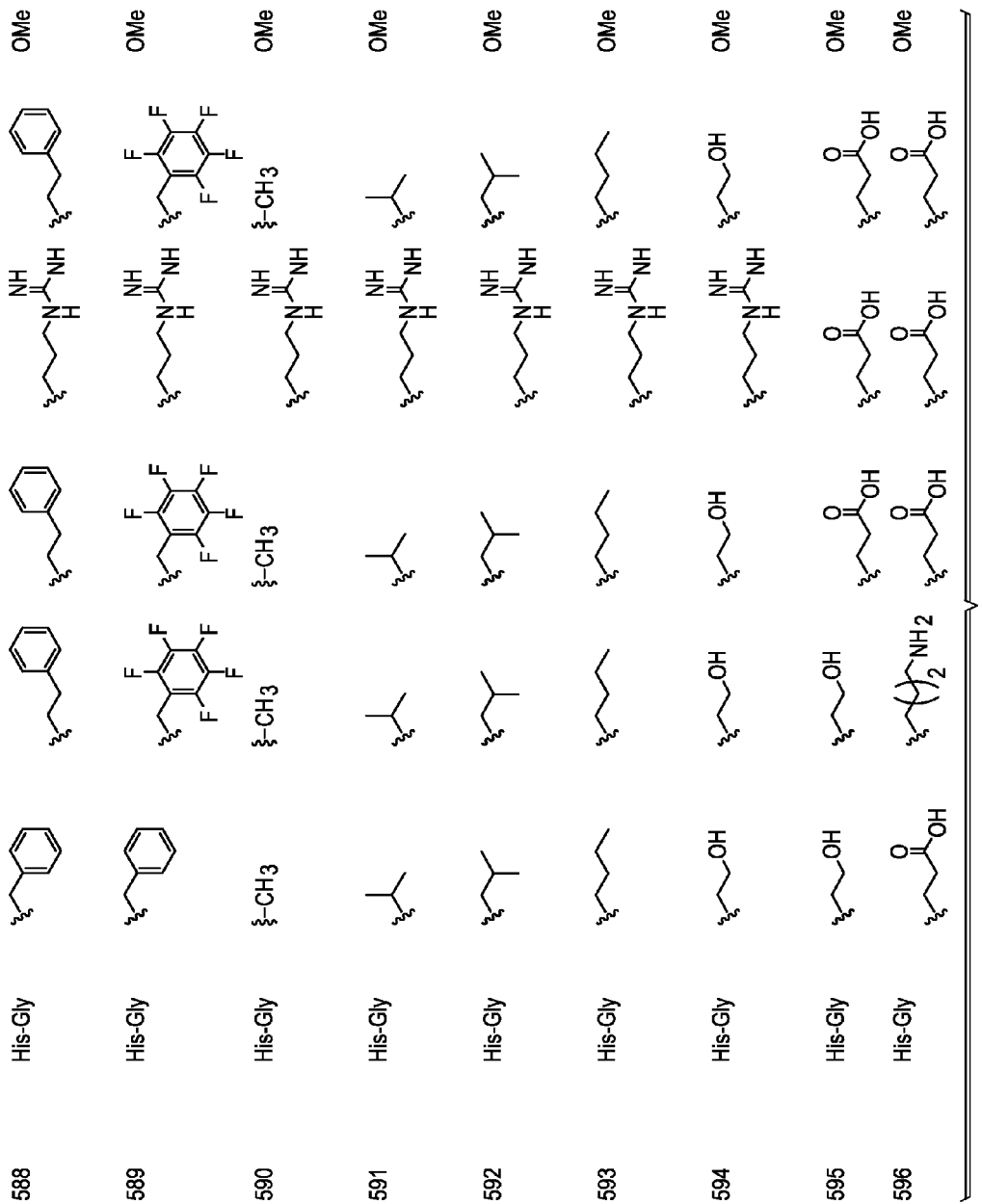
Figures 5, 18G:
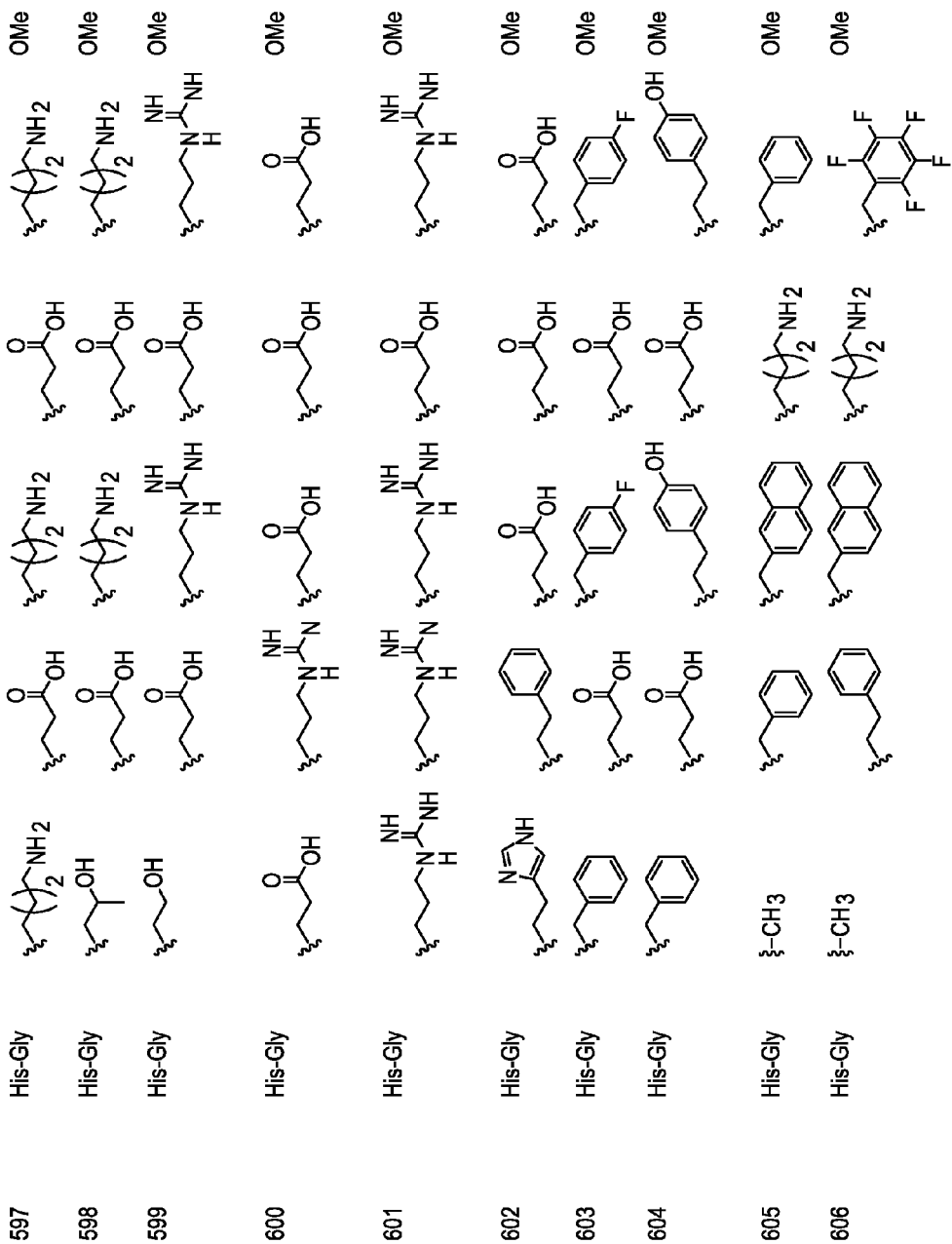
Figures 6, 18G:
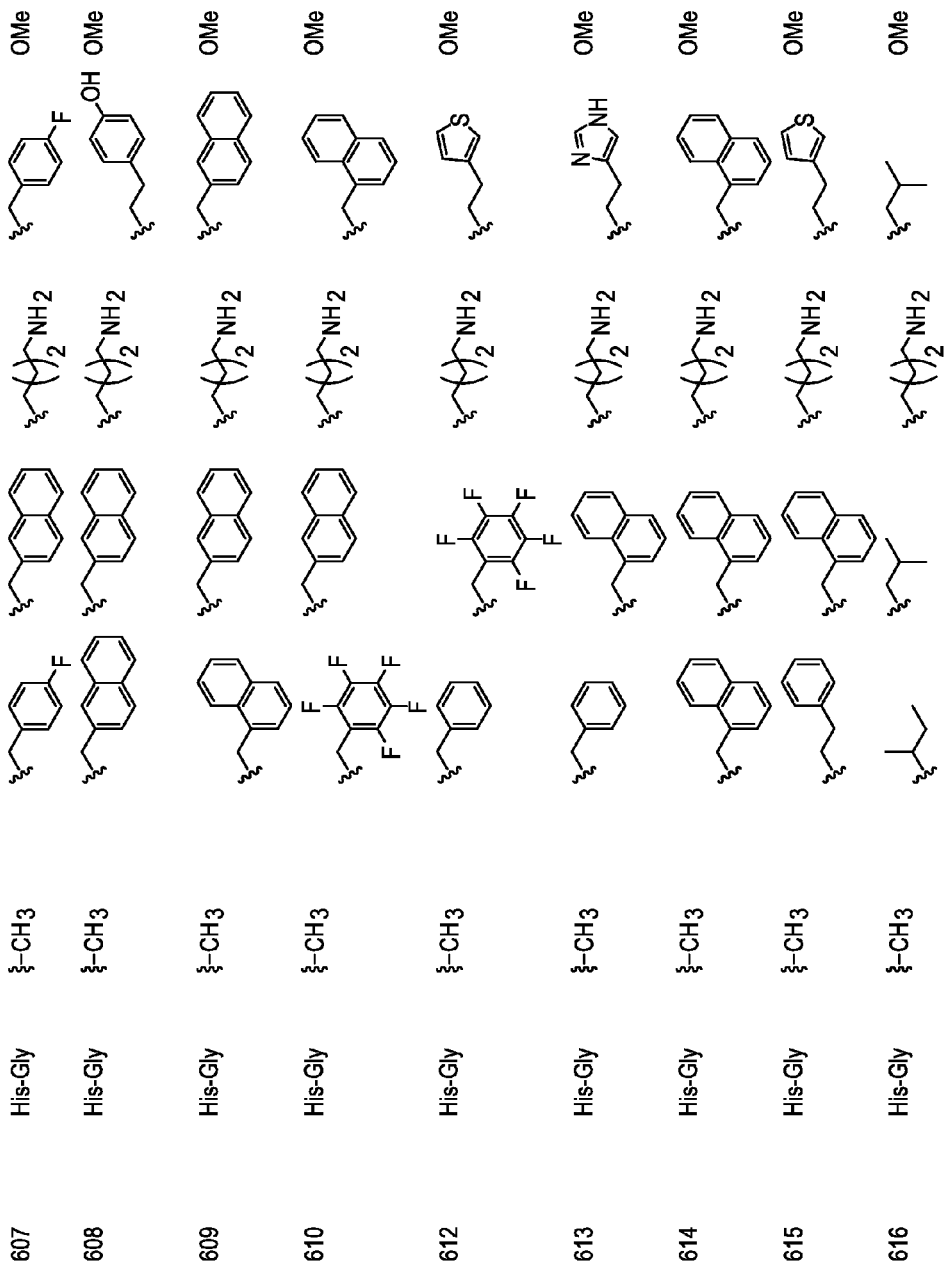
Figures 7, 18G:
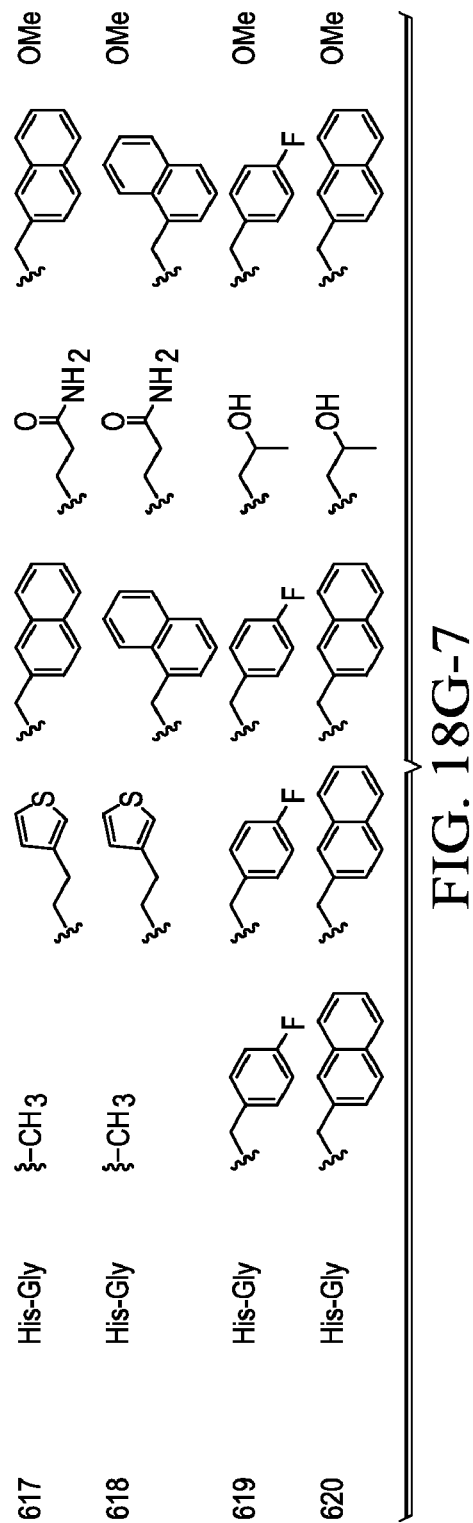
Figures 2, 18H:
Figures 3, 18H:
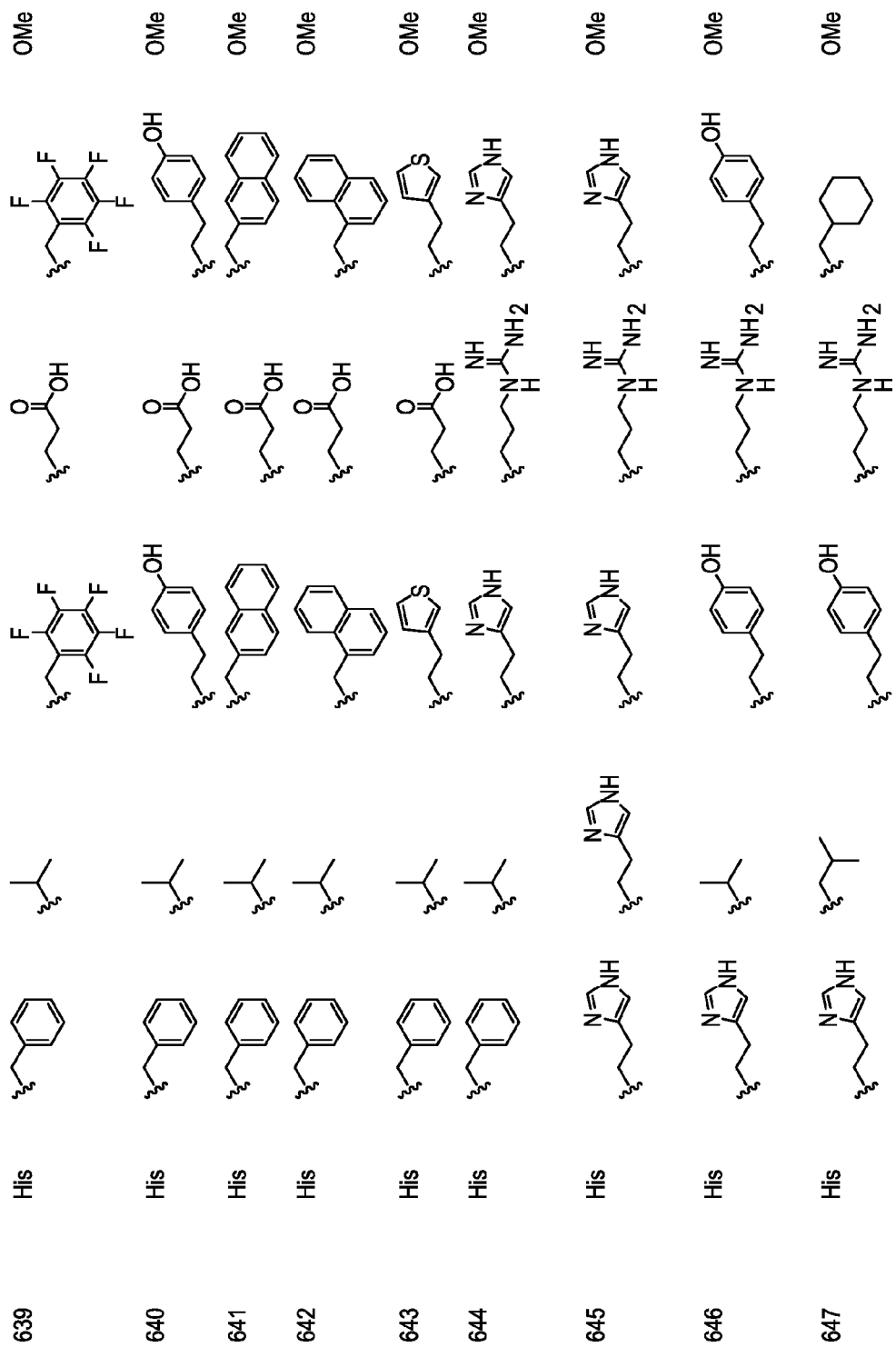
Figures 4, 18H:
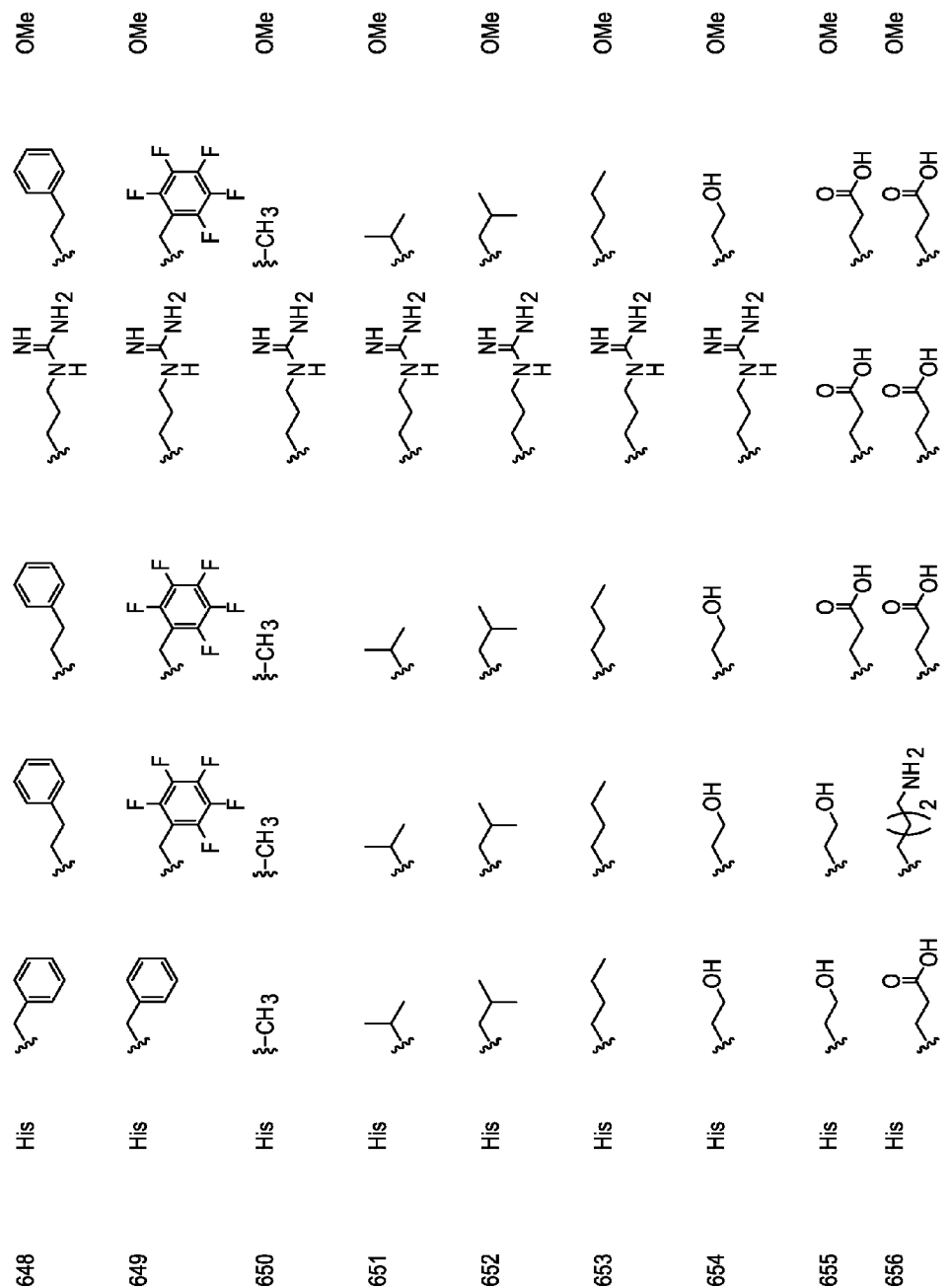
Figures 5, 18H:
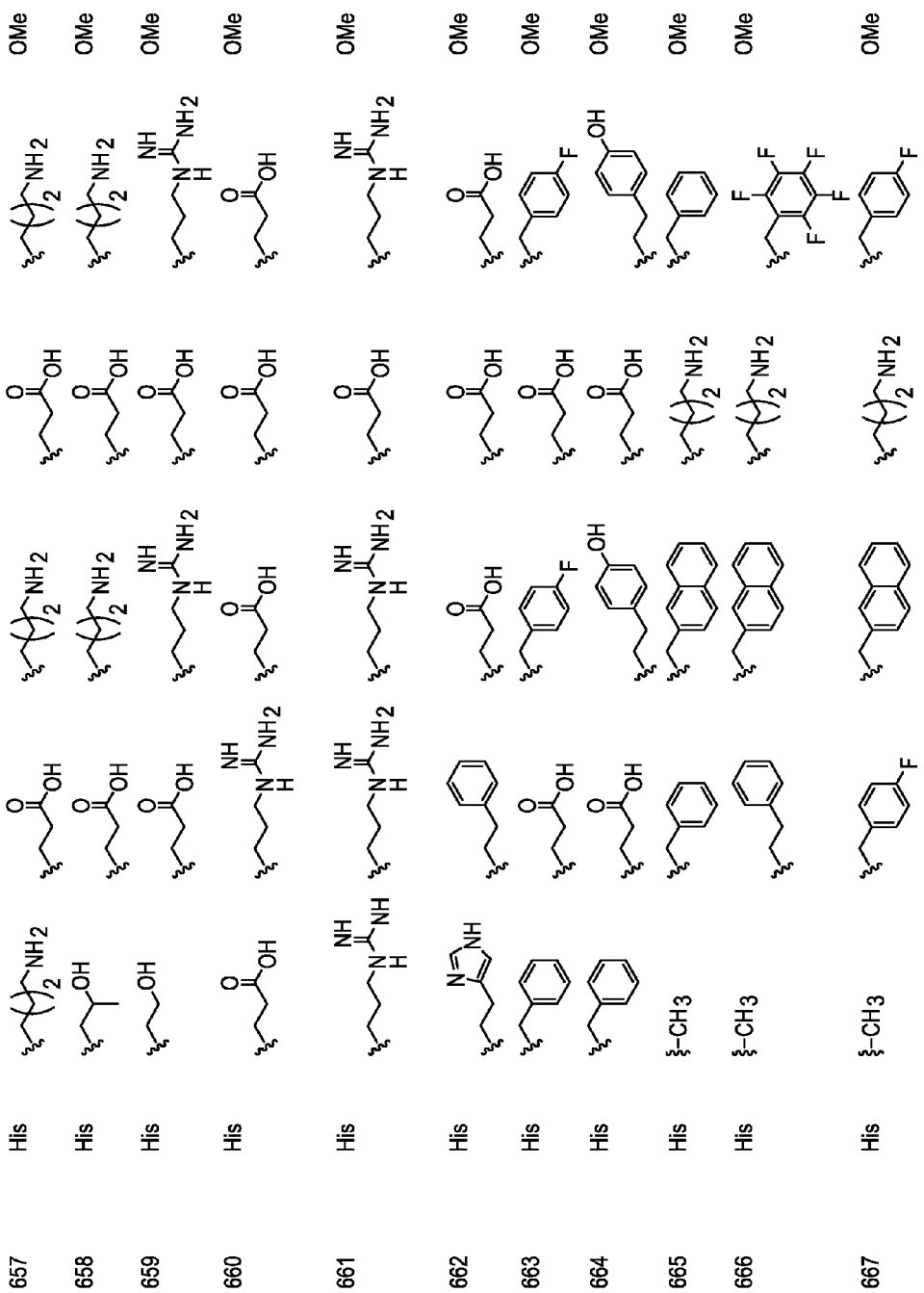
Figures 6, 18H:
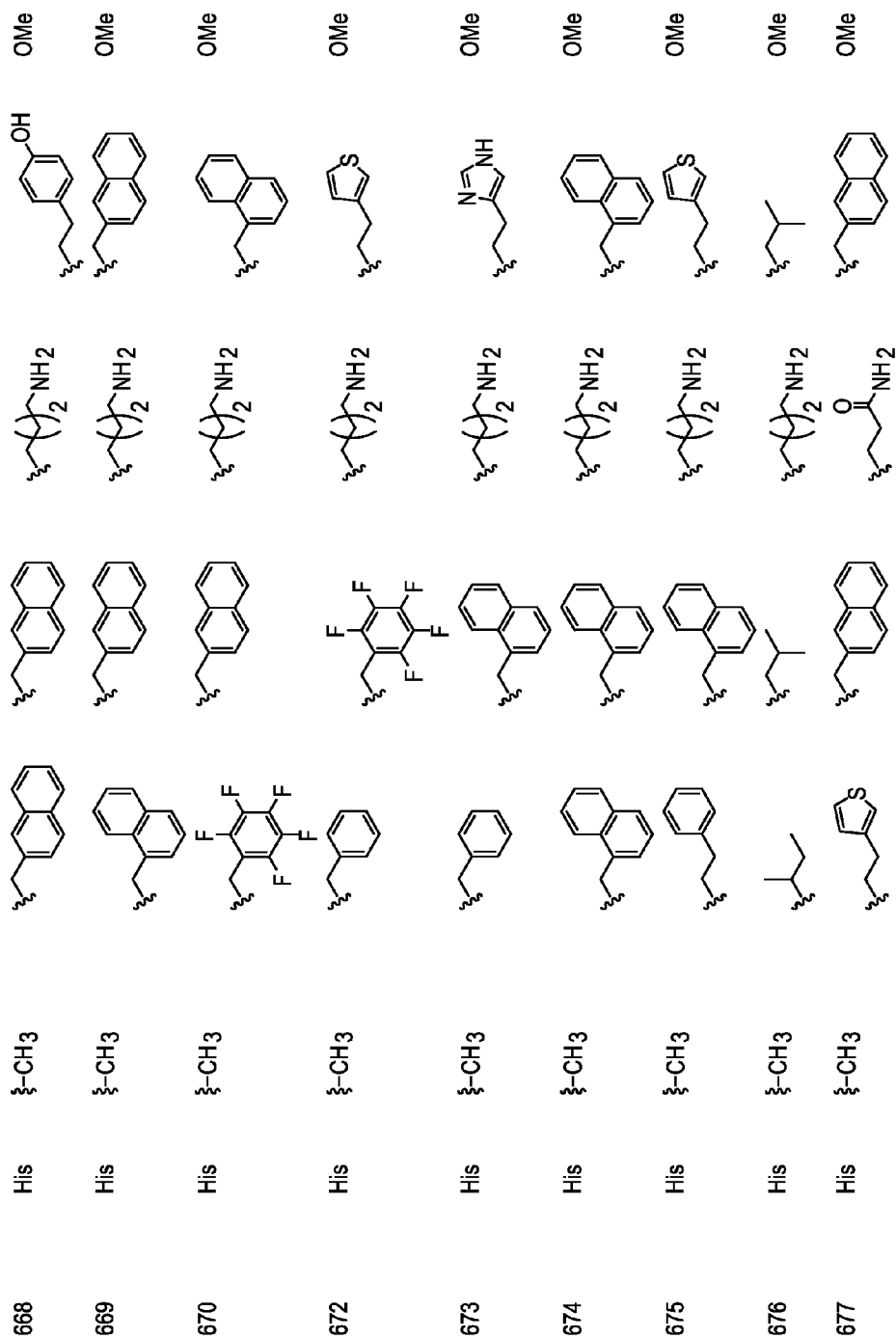
Figures 7, 18H:
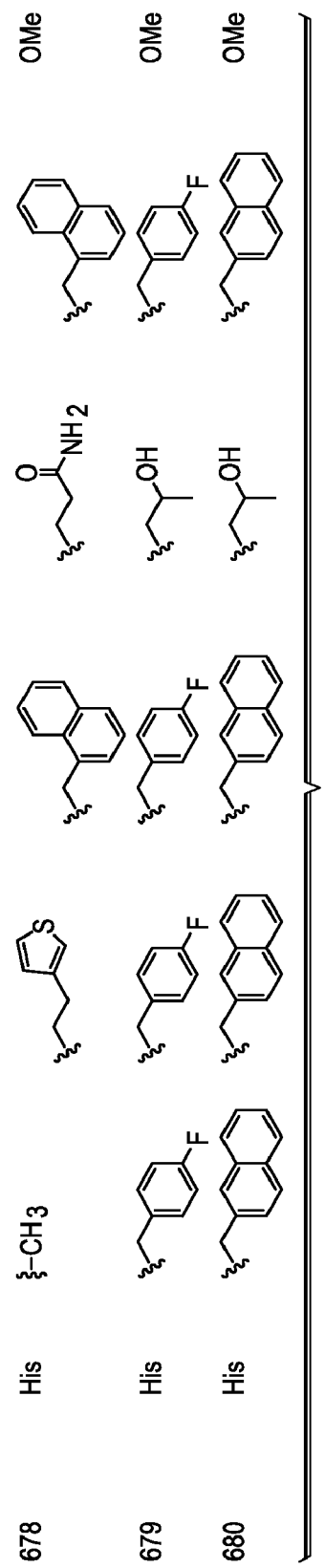
Figures 1, 18I:
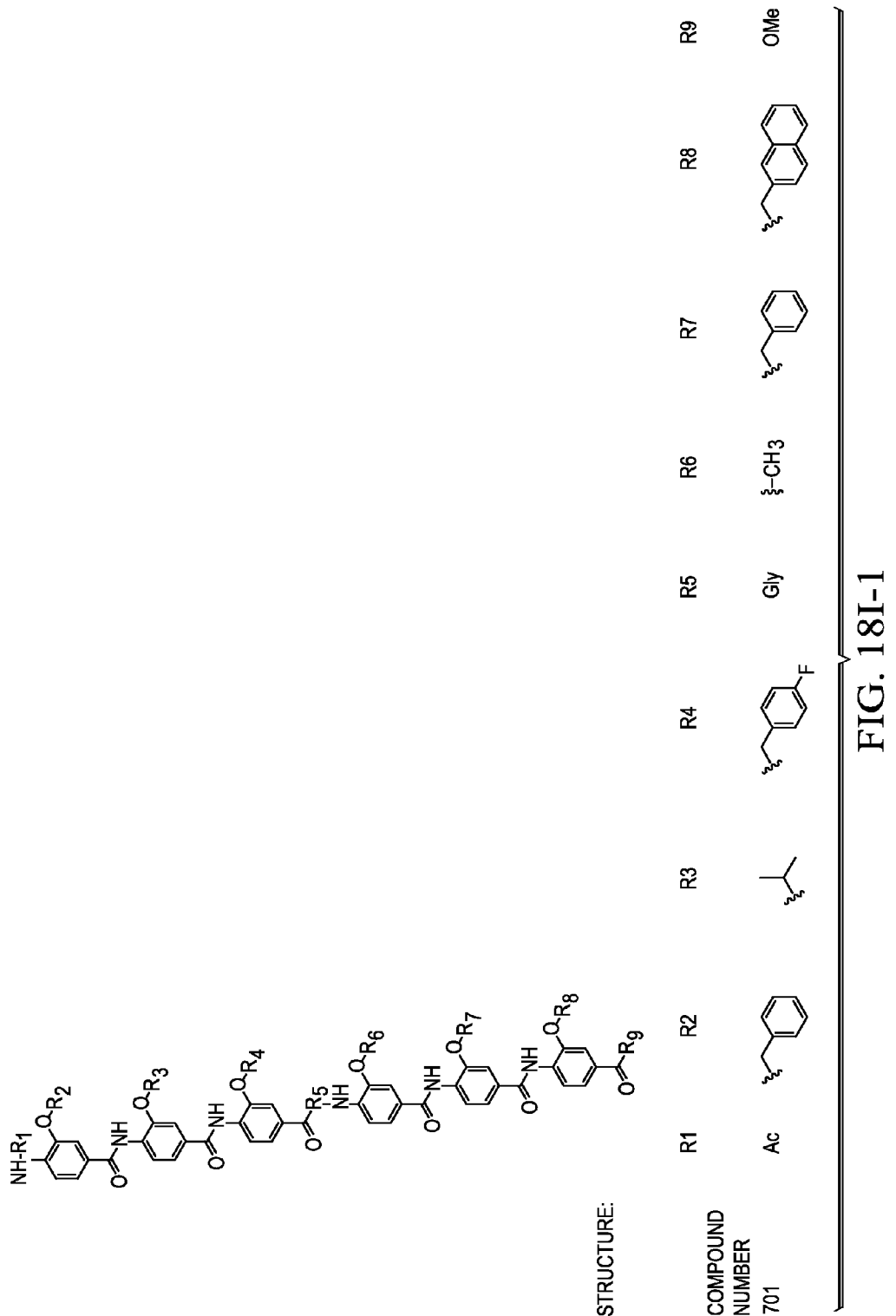
Figures 2, 18I:
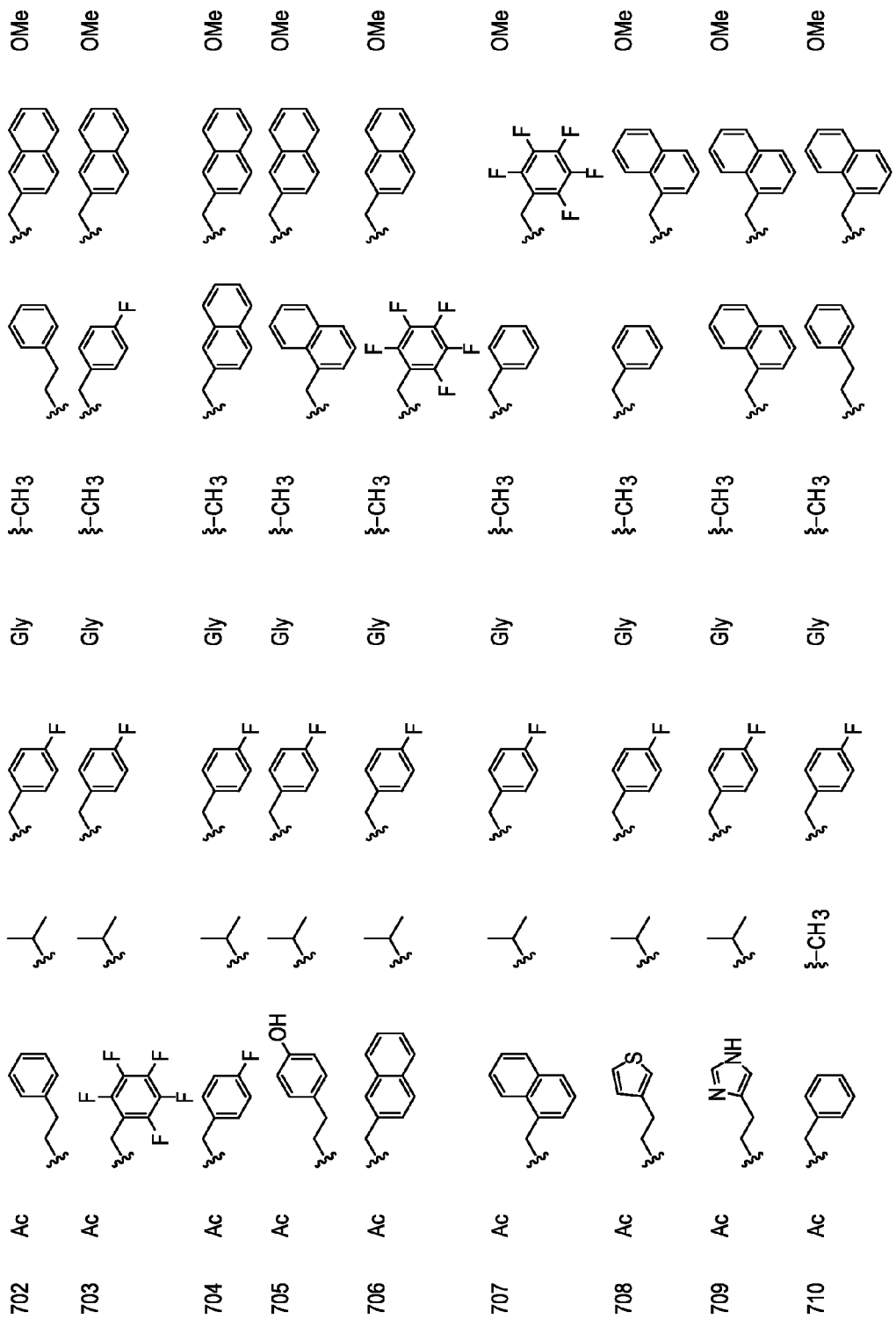
Figures 3, 18I:
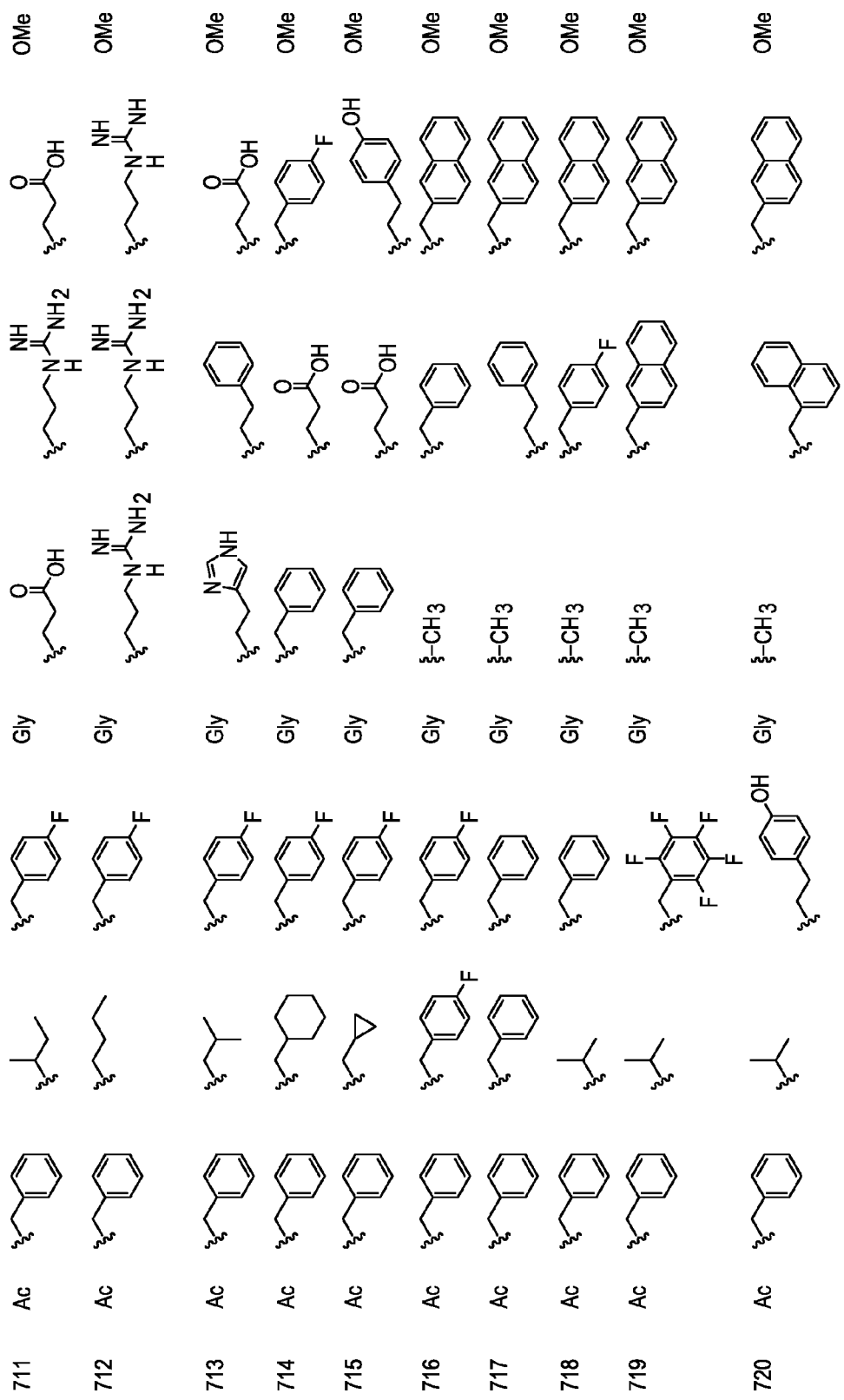
Figures 4, 18I:
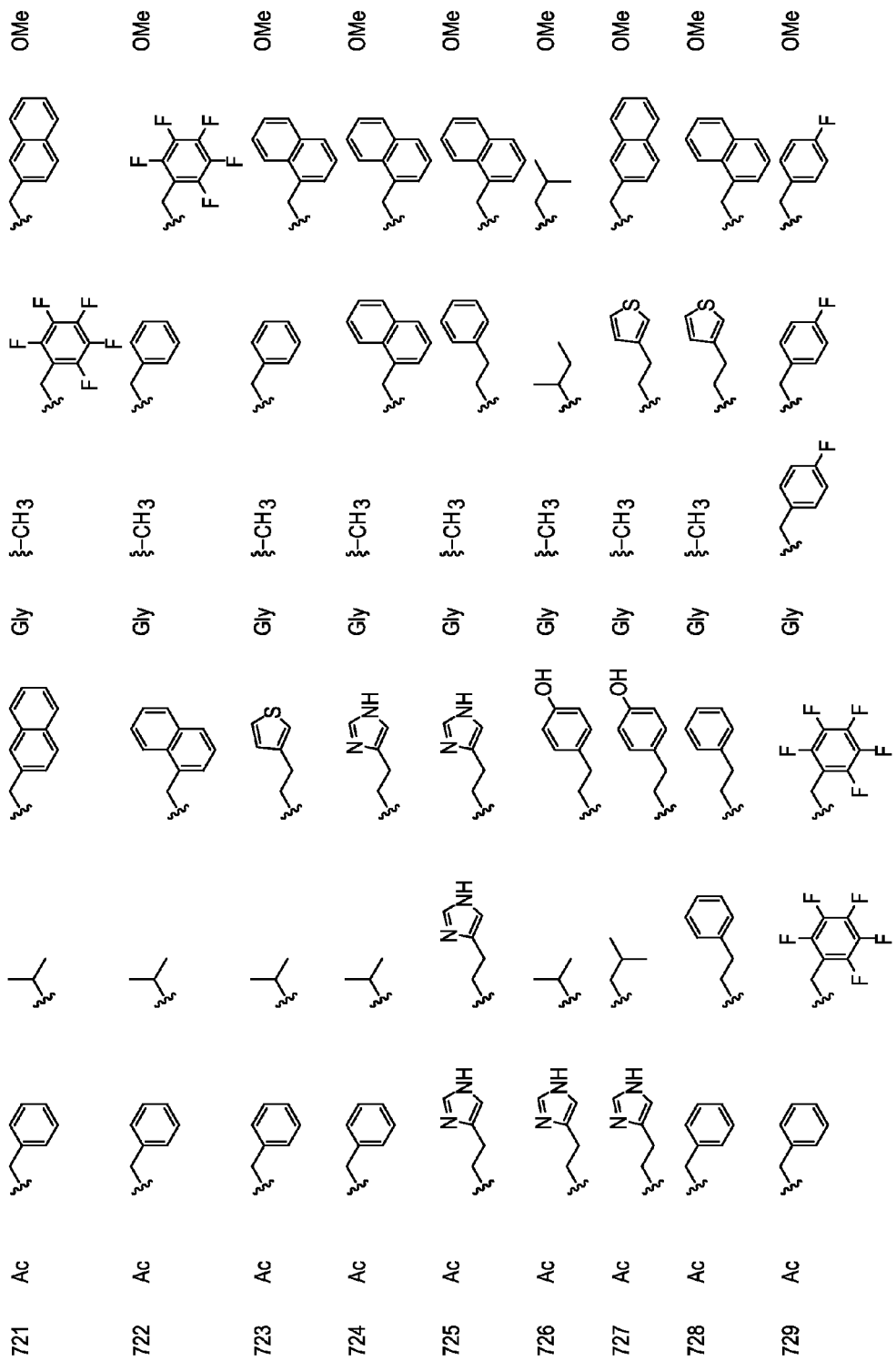
Figures 5, 18I:
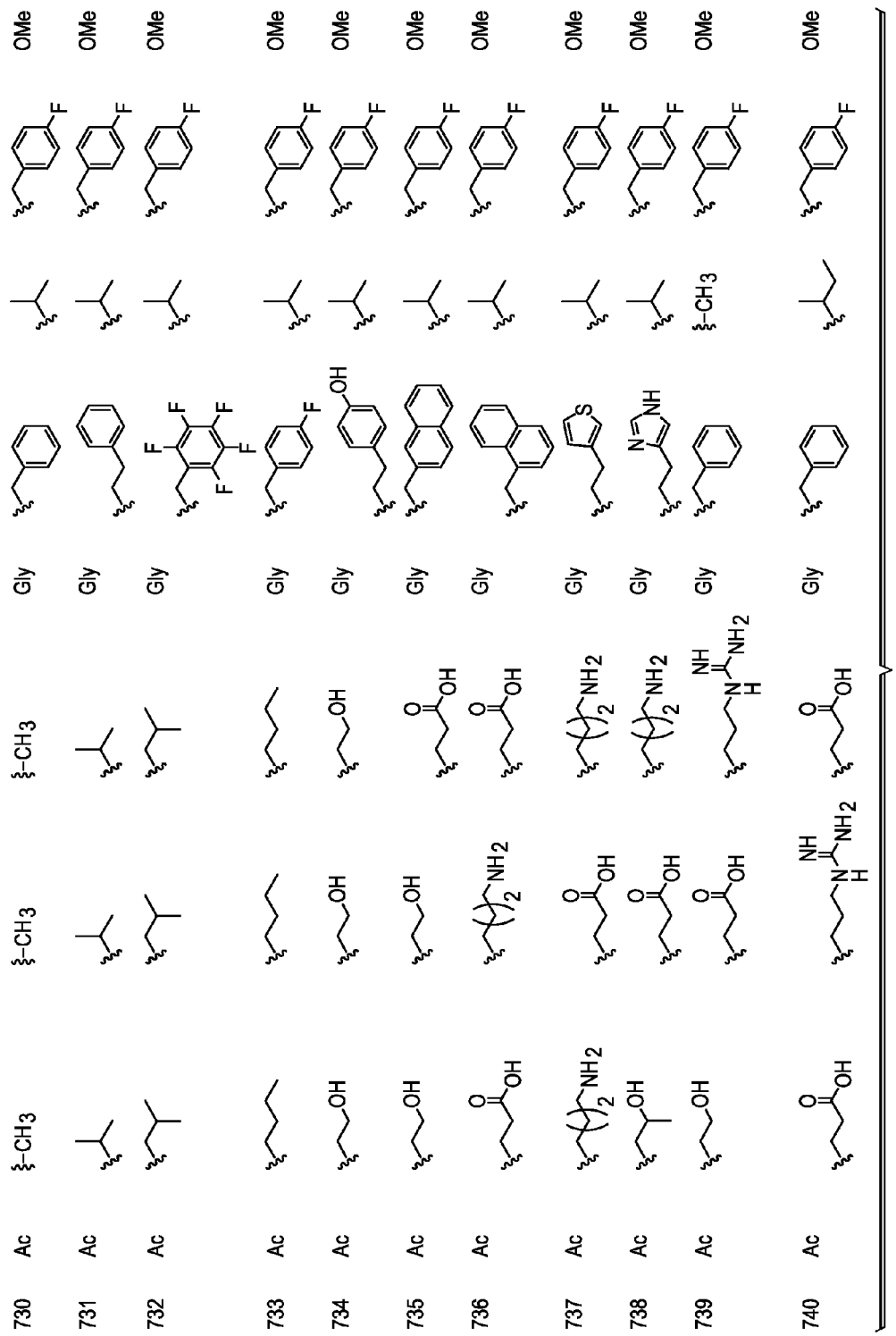
Figures 6, 18I:
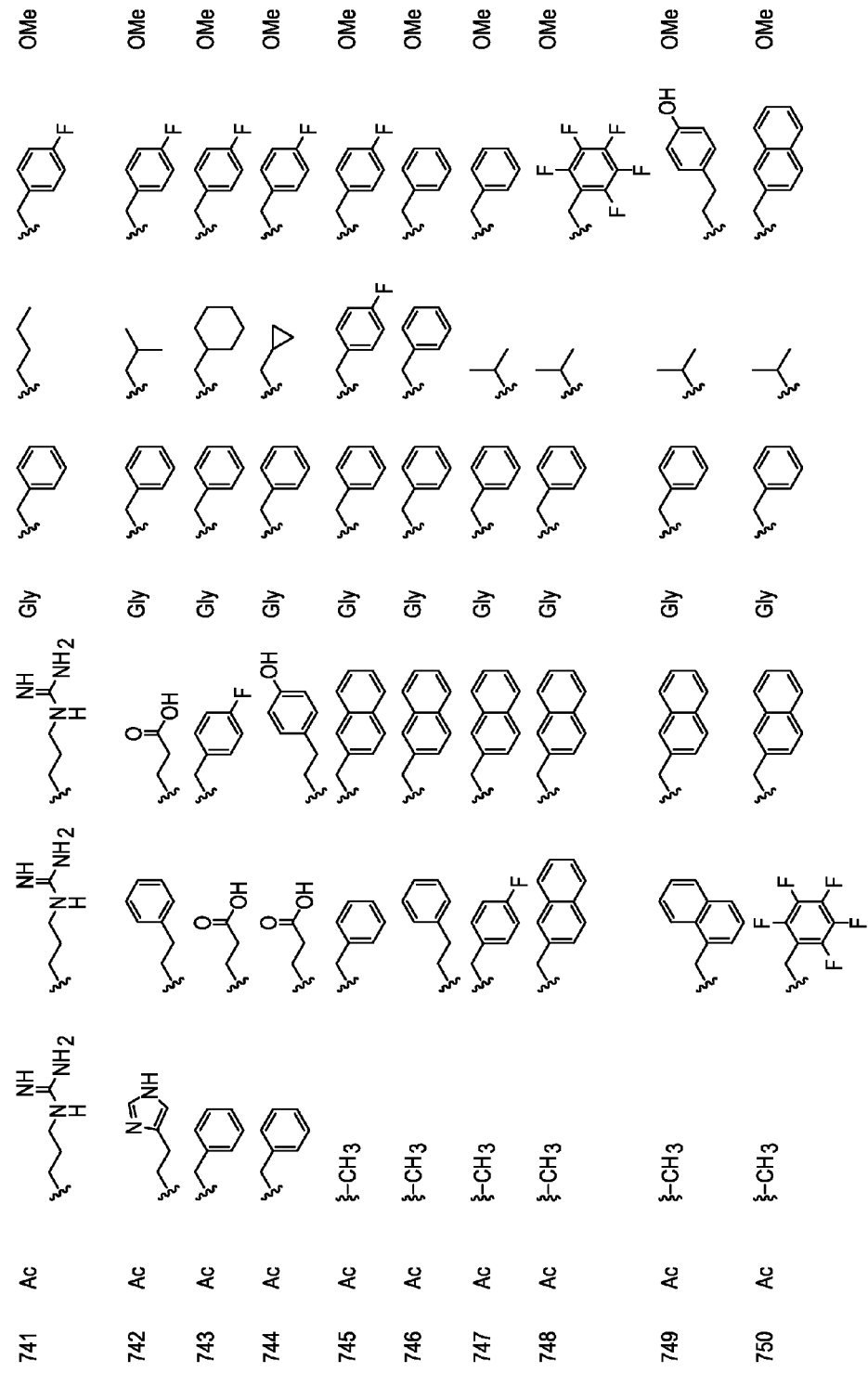
Figures 7, 18I:
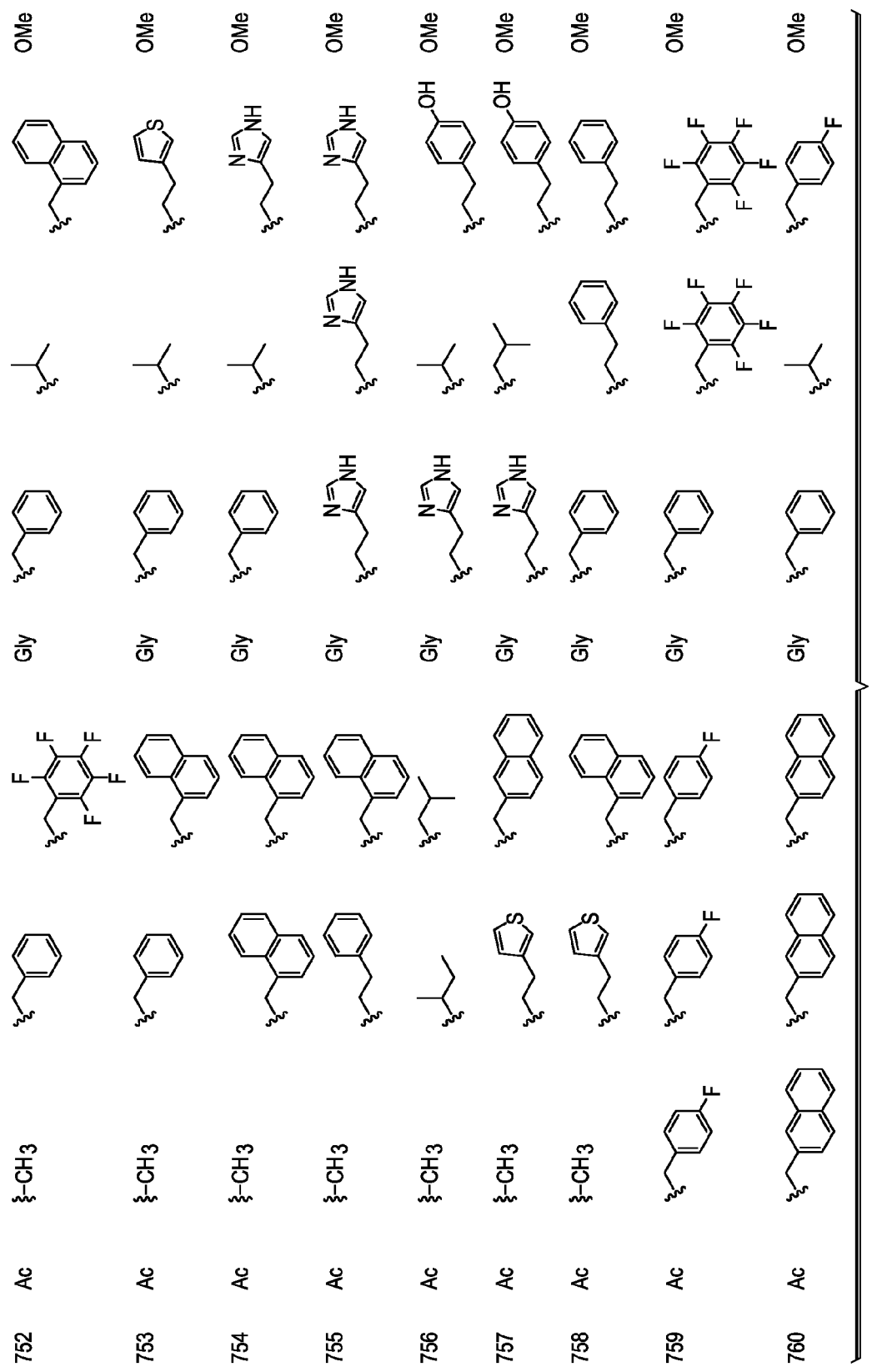
Figures 1, 18J:
Figures 2, 18J:
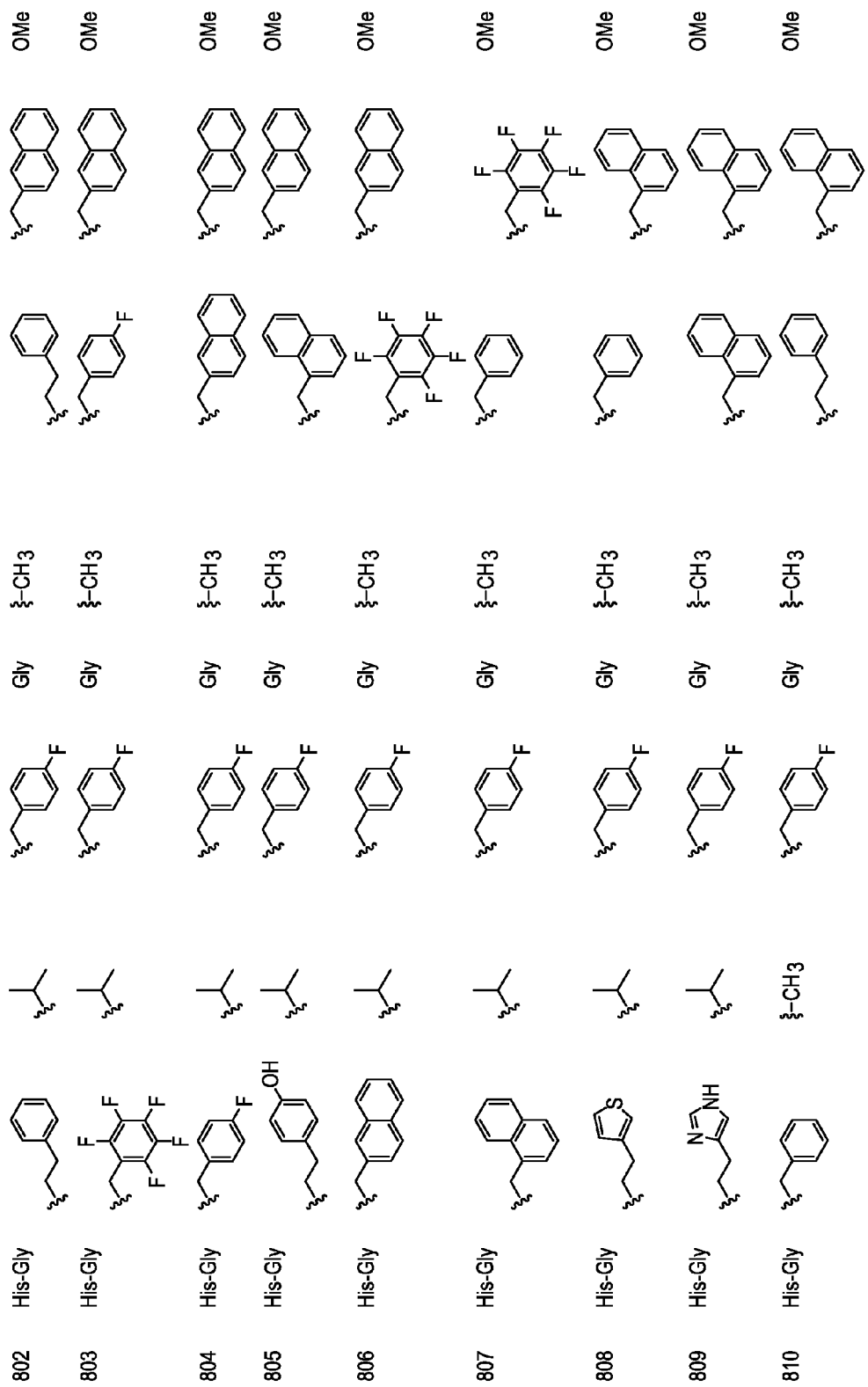
Figures 3, 18J:
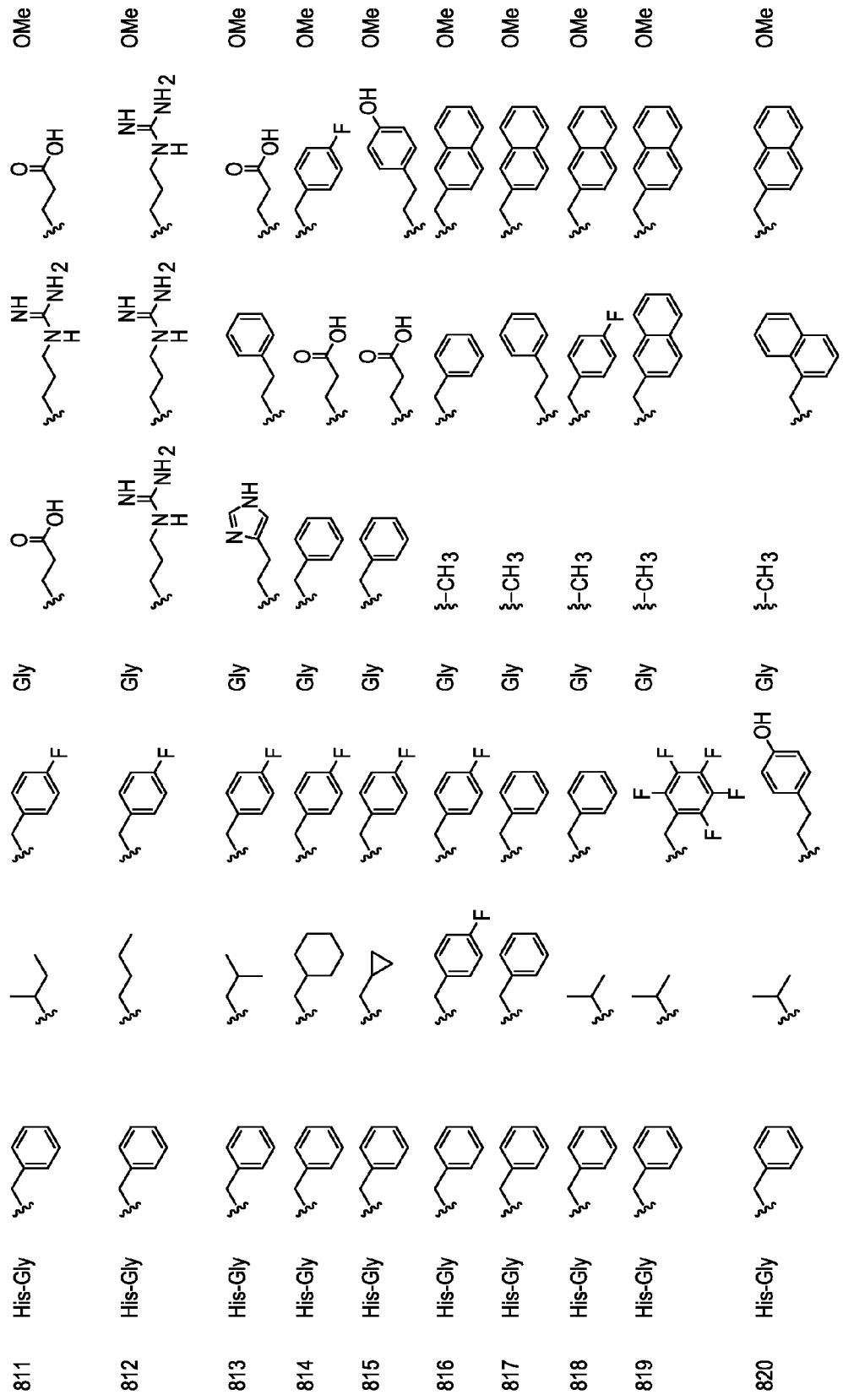
Figures 4, 18J:
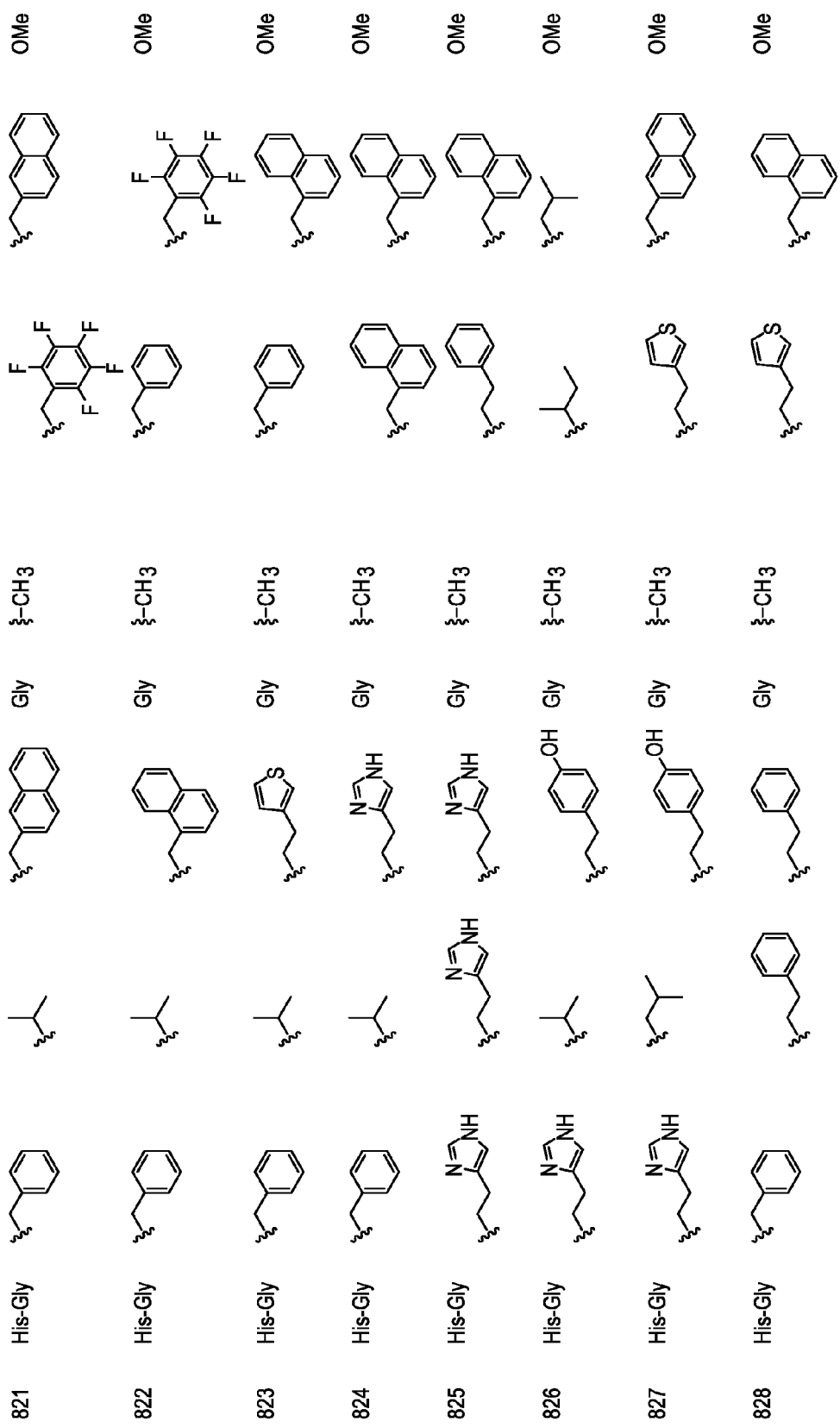
Figures 5, 18J:
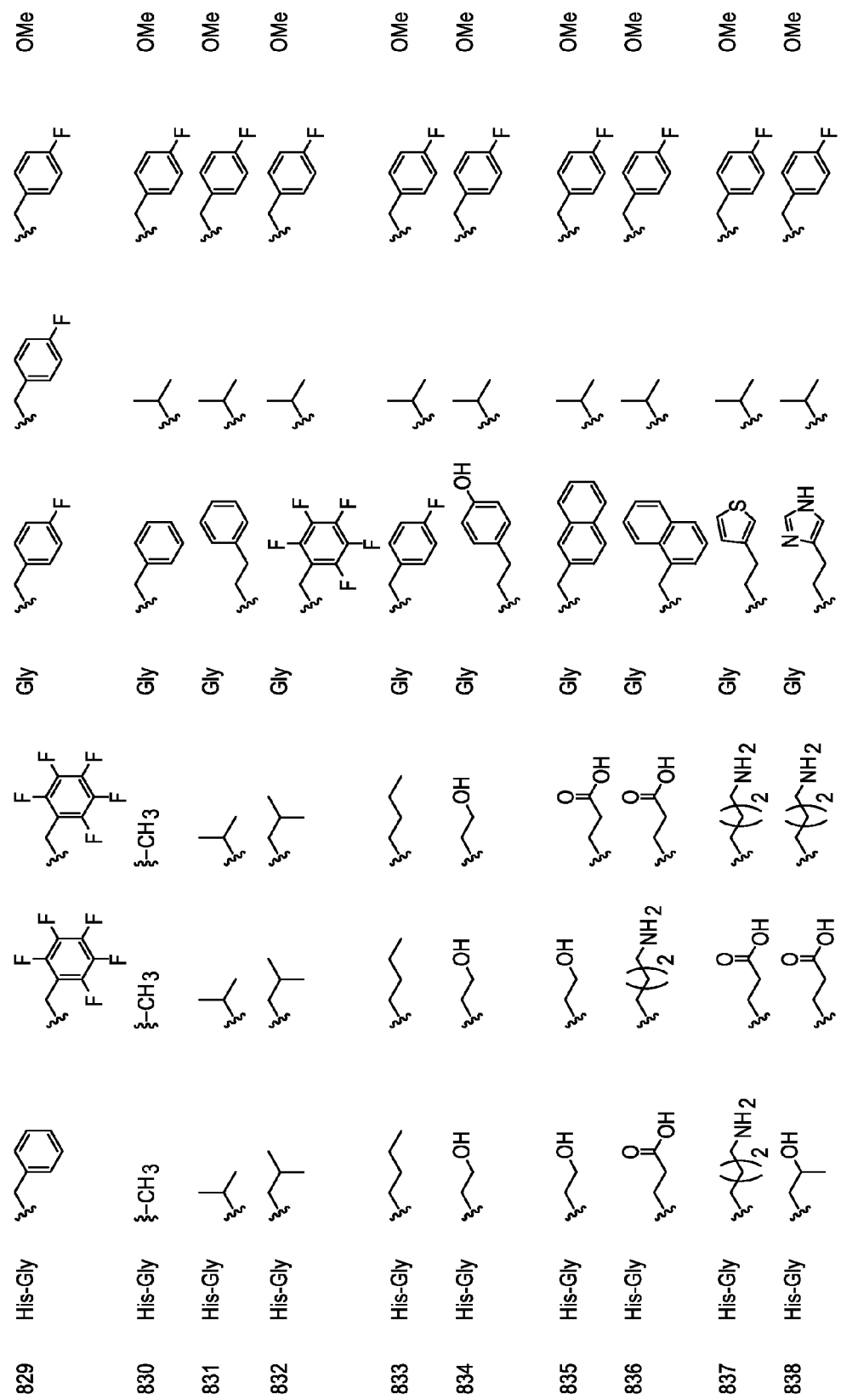
Figures 6, 18J:
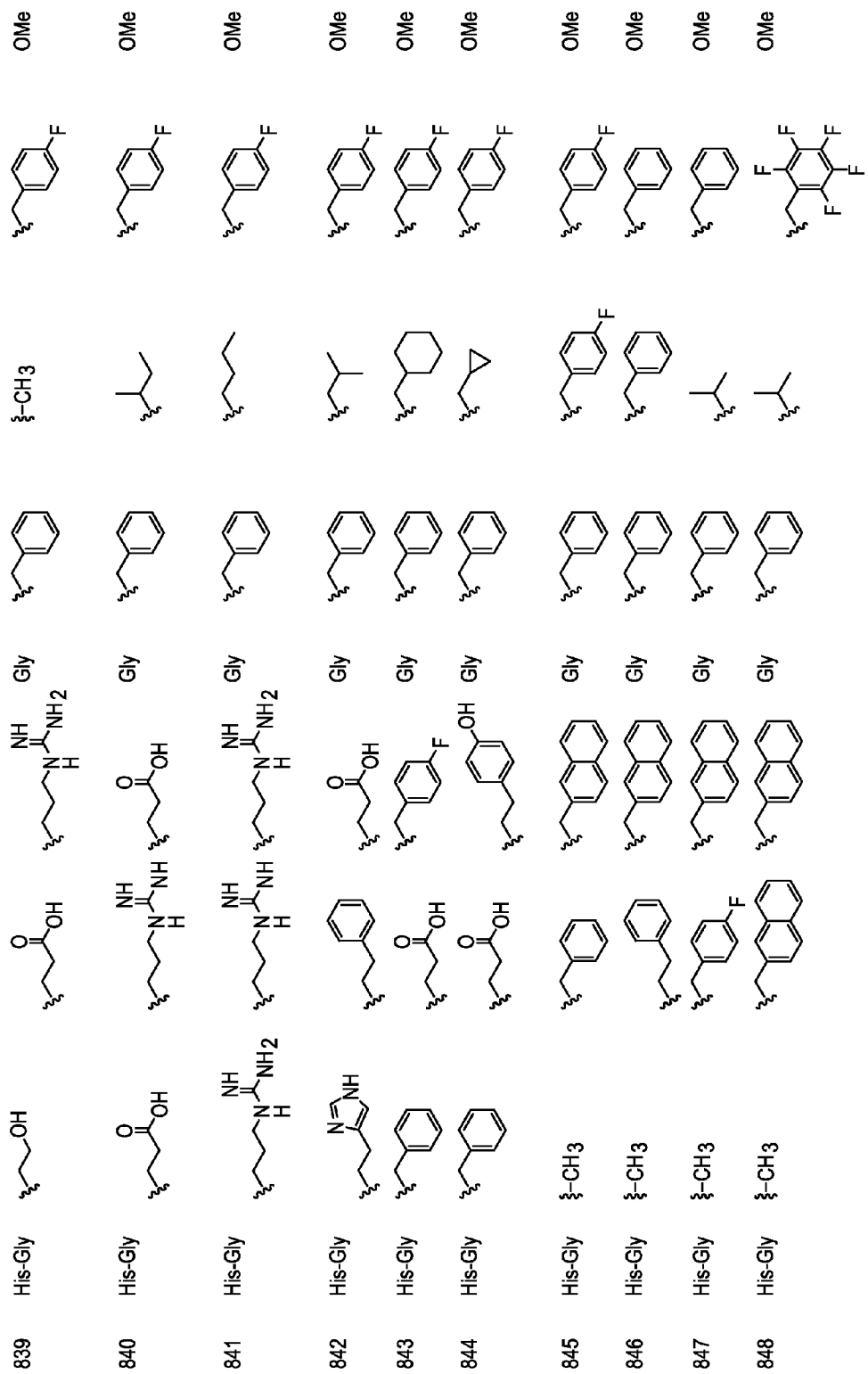
Figures 7, 18J:
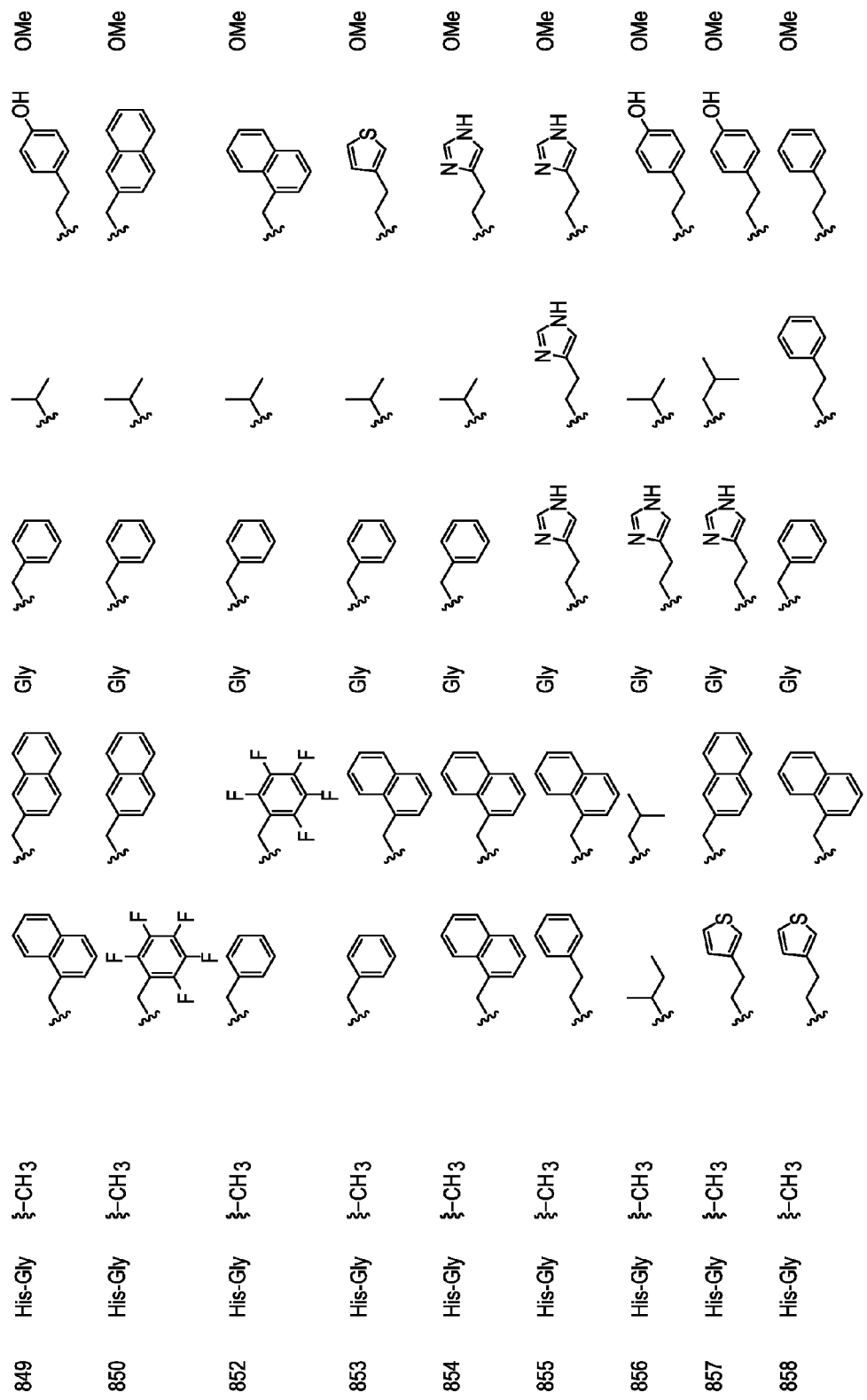
Figures 8, 18J:
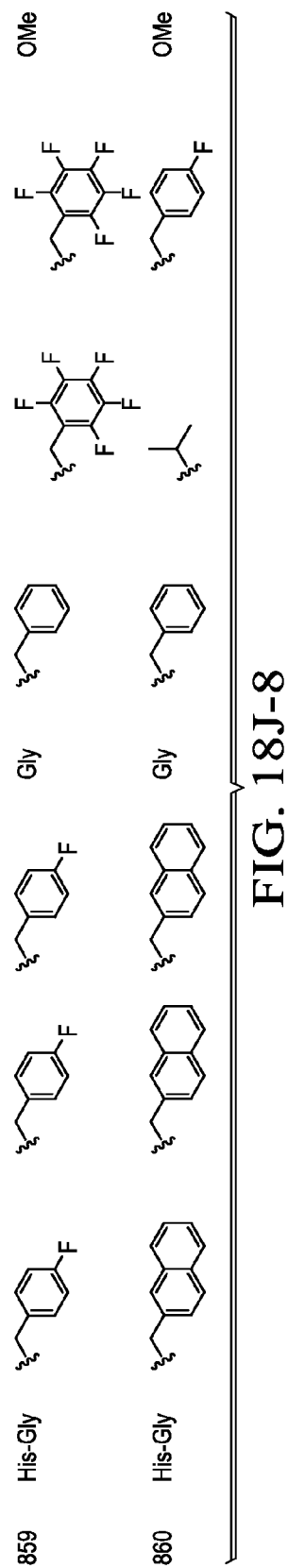
Figures 1, 18K:
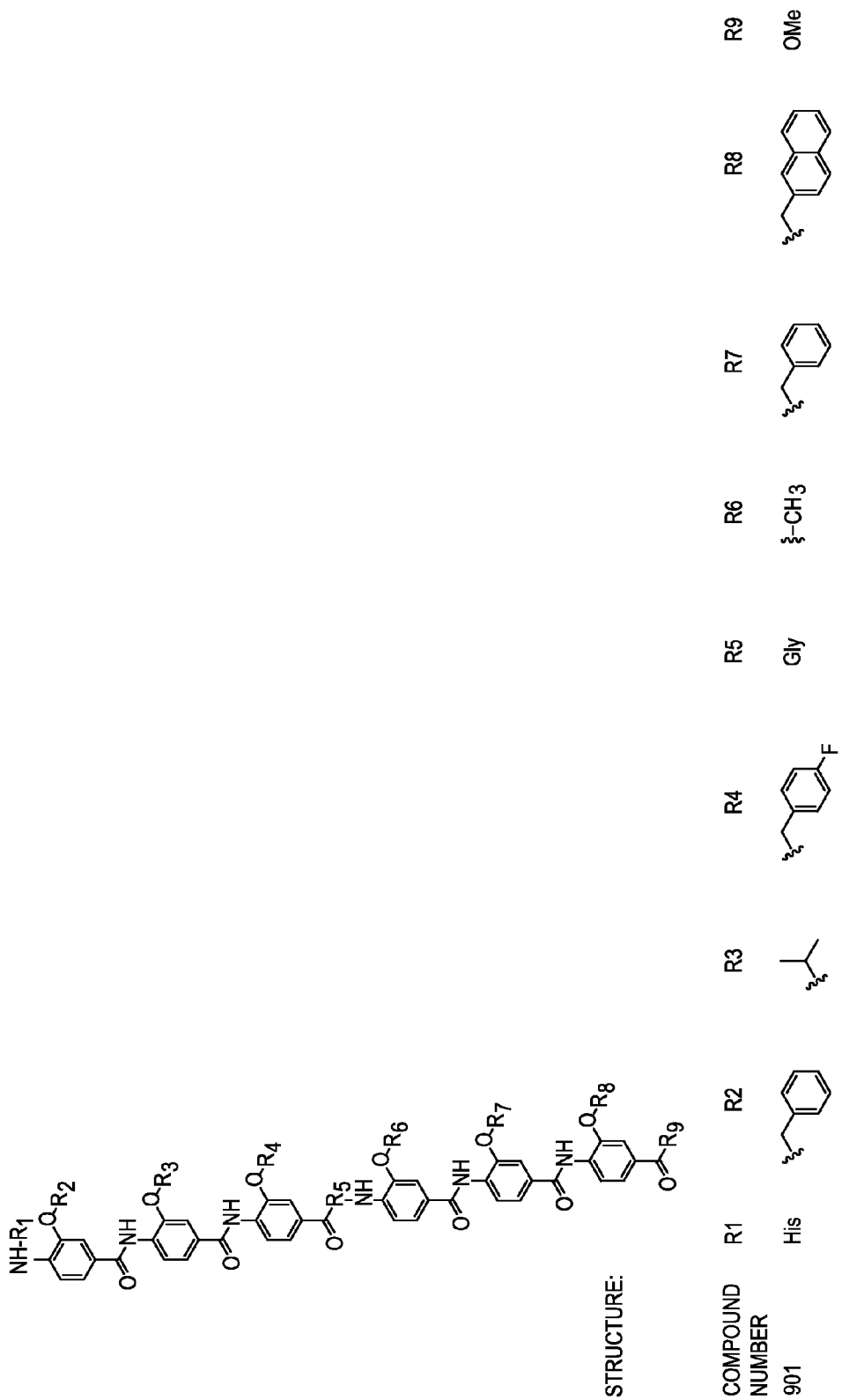
Figures 2, 18K:
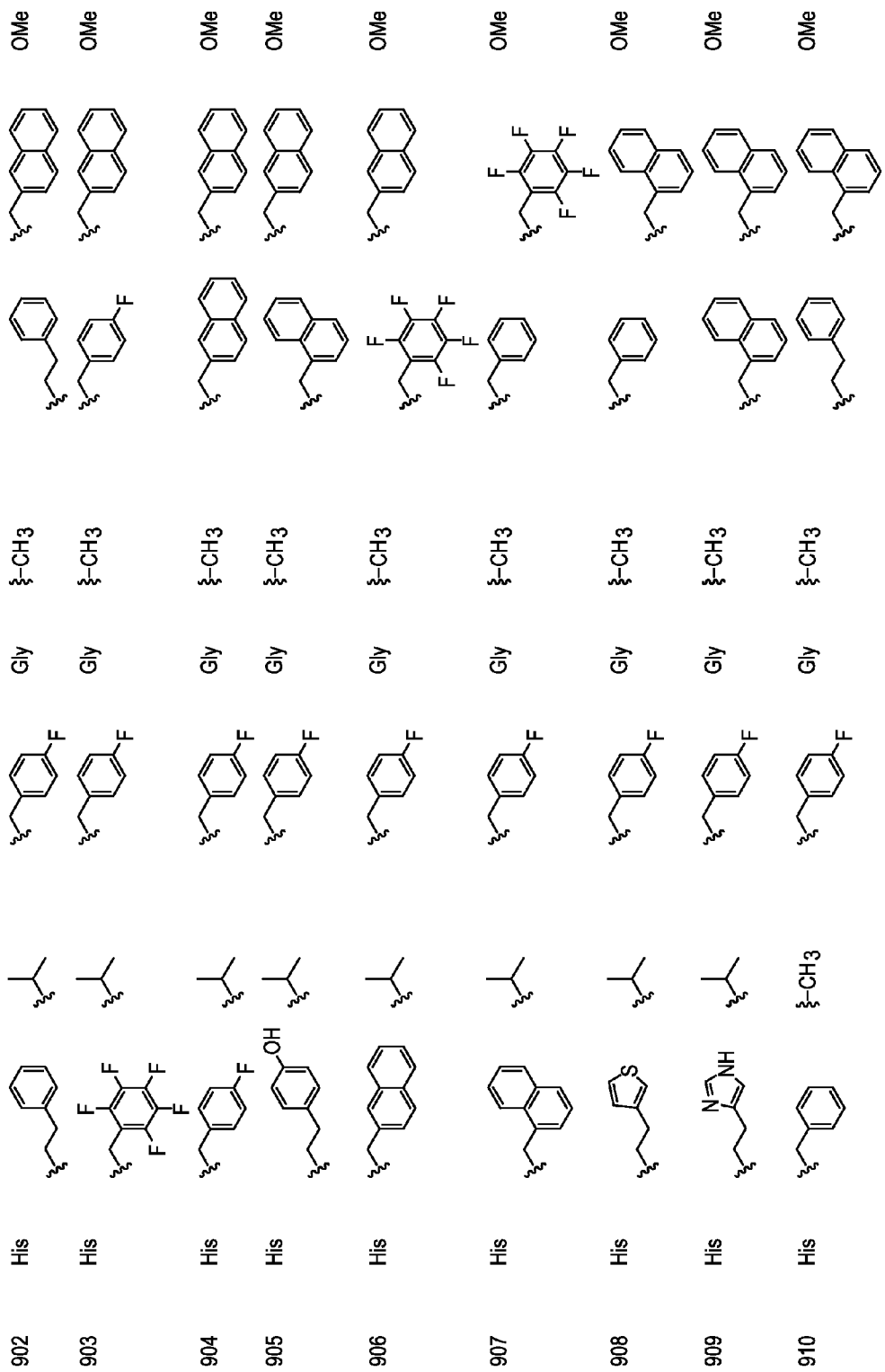
Figures 3, 18K:
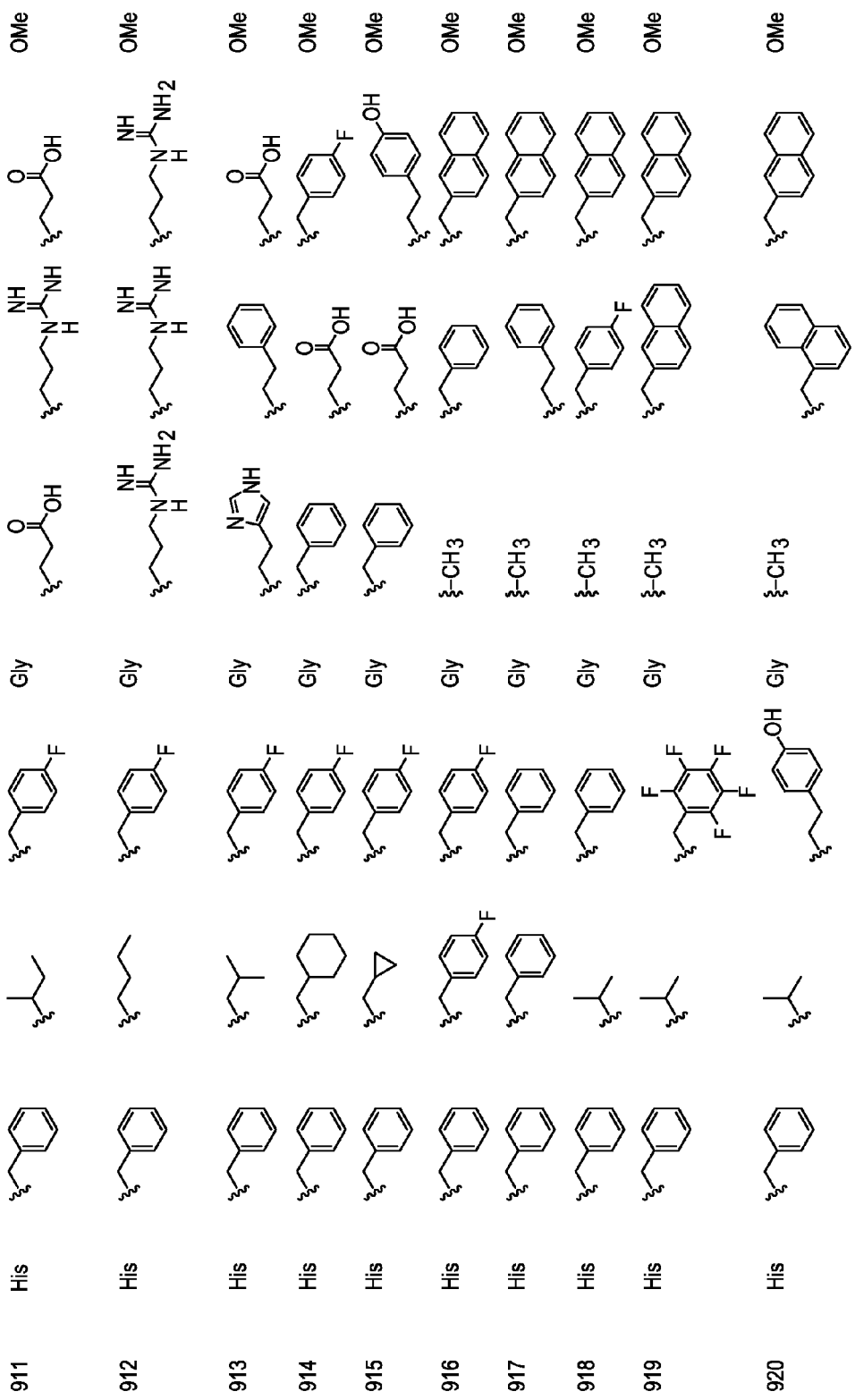
Figures 4, 18K:
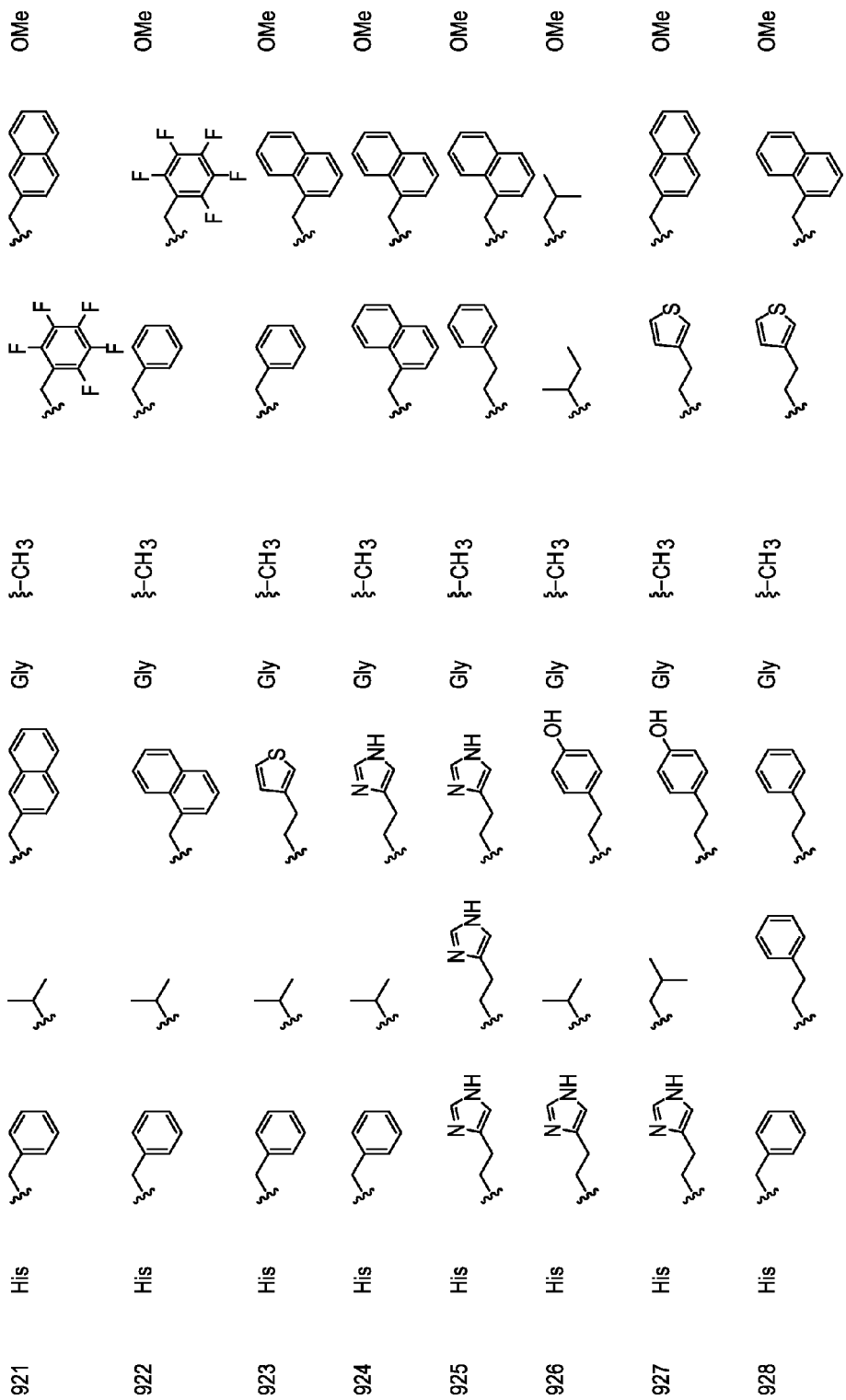
Figures 5, 18K:
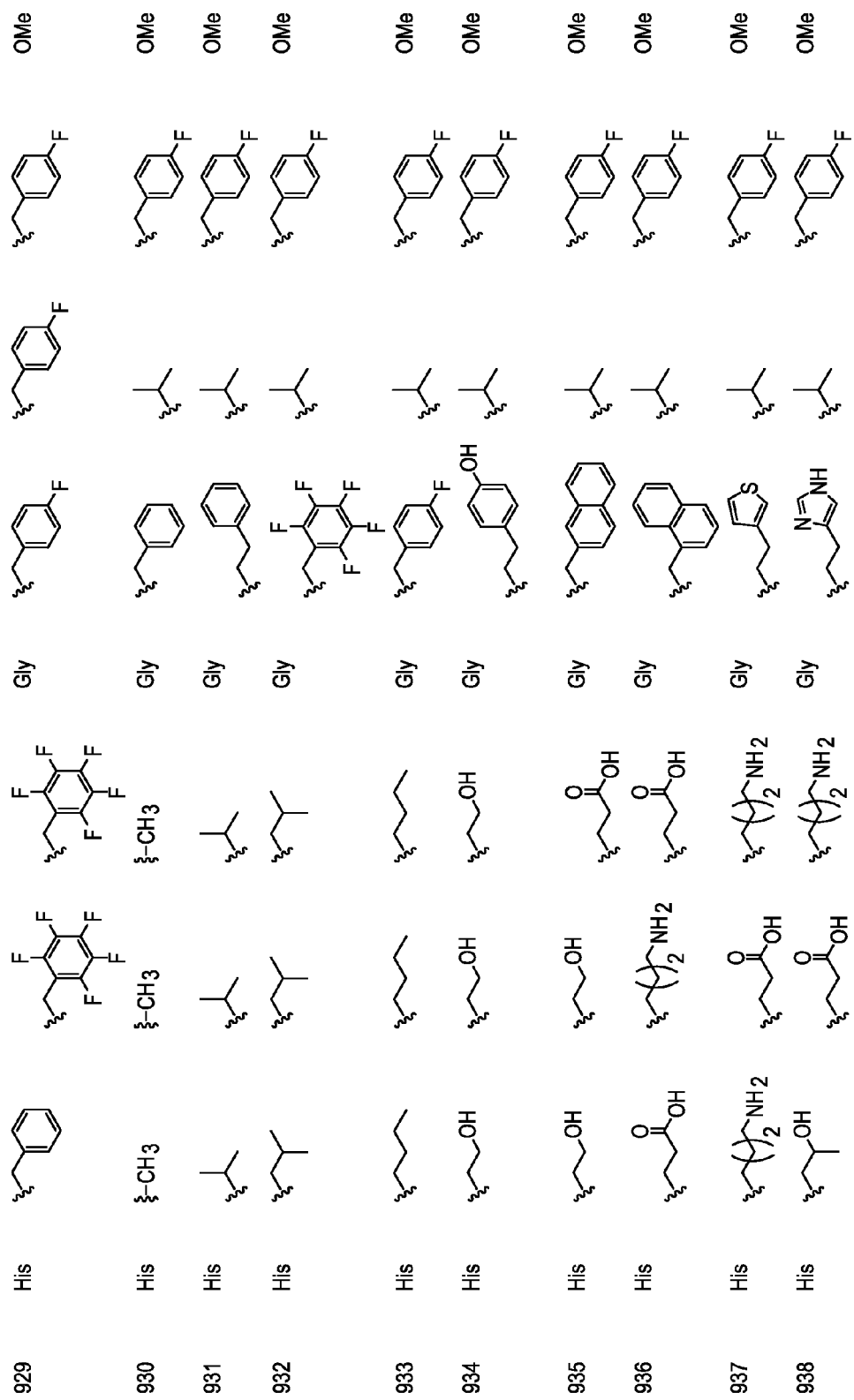
Figures 6, 18K:
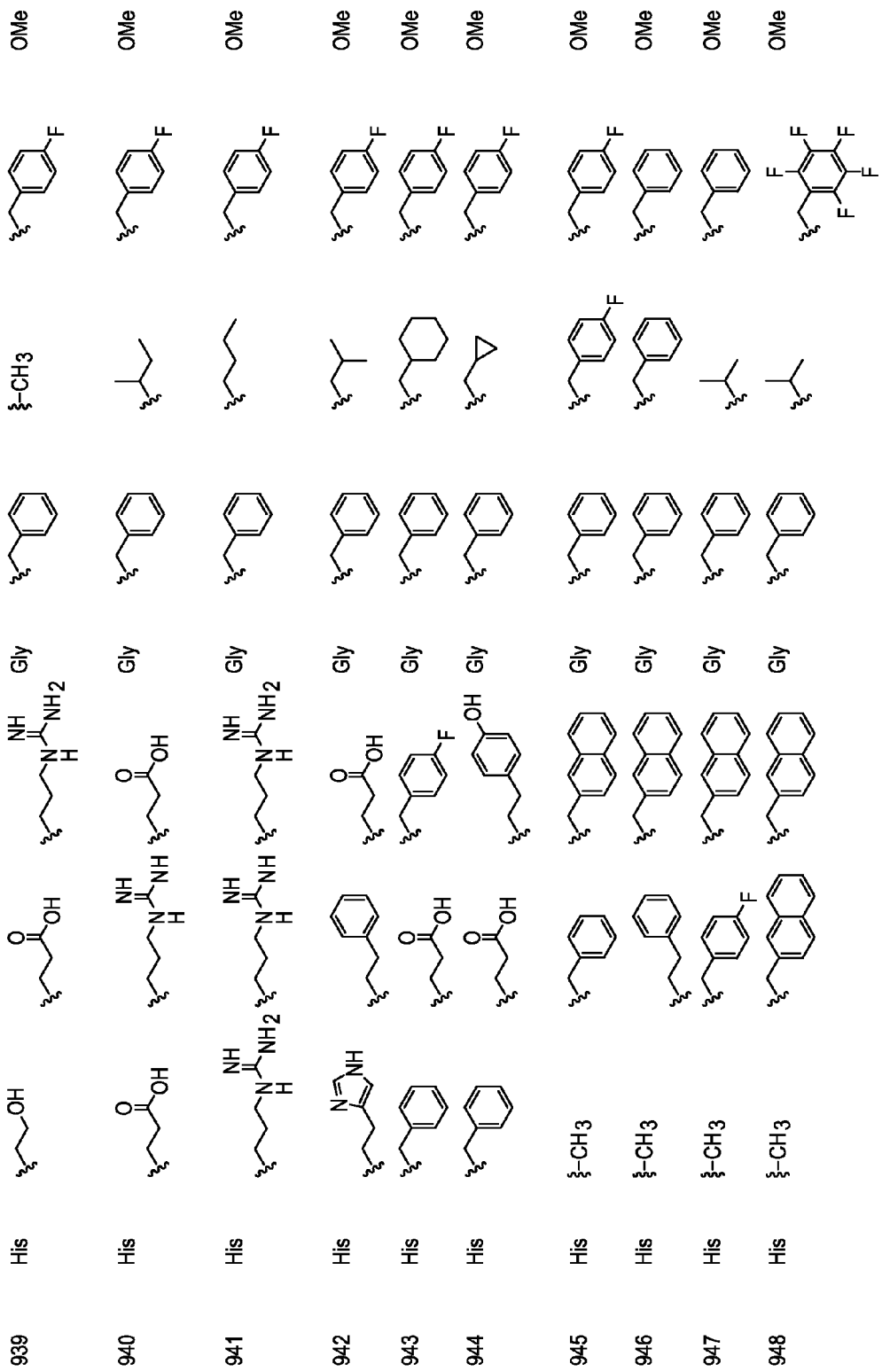
Figures 7, 18K:
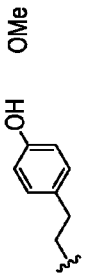
Figures 8, 18K:
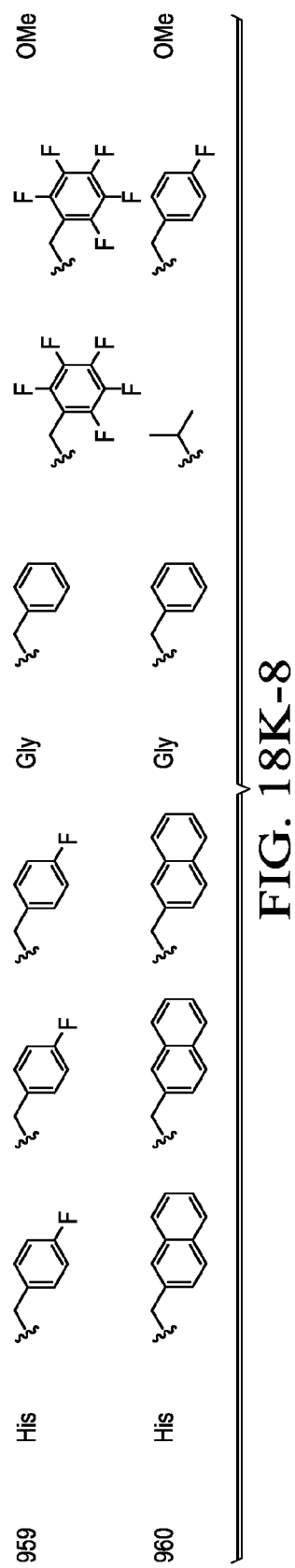

The helical wheel plots of FIG. 3 illustrates that the helical segments in GLP-1 are amphiphilic, presenting hydrophobic functional groups on one side and hydrophilic functional groups on the opposite side. The present invention provides amphiphilic α-helix mimetic compounds having functionalities found on both sides of the α-helix to confer higher potency.

Figure 6A:
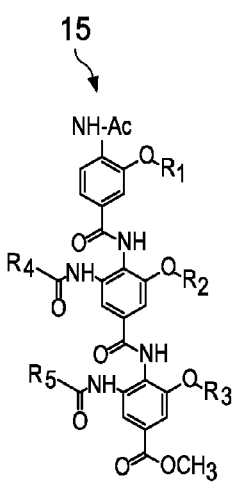
FIGS. 6A-6C are images that illustrate the structures of α-helix peptidomimetic compounds that represent two α-helical faces of a peptide.
Figure 6B:
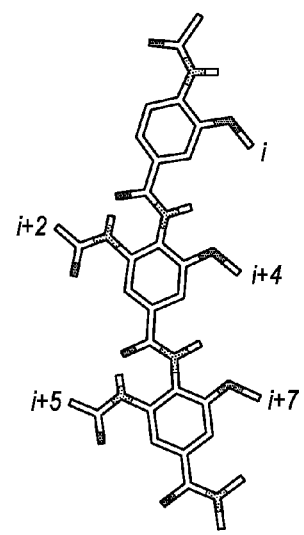
Figure 6C:
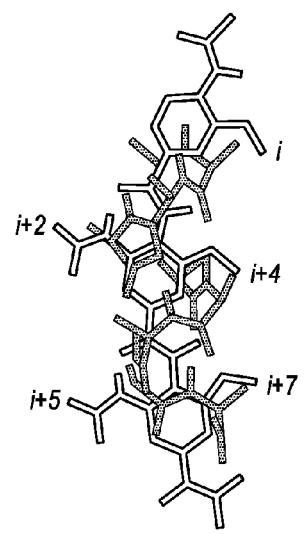

FIGS. 6A-6C are images that illustrates the structures of amphiphilic α-helix mimetics. FIG. 6A is an image of an amphiphilic α-helix mimetic compound, FIG. 6B is an image of an energy-minimized structure of an amphiphilic α-helix mimetic compound, FIG. 6C is an image of a superimposition of an amphiphilic α-helix mimetic compound (orange) with an α-helix (green). The helical wheel plots of GLP-1 suggested five amphiphilic helix mimetics to represent the N-terminal helical segment. Another five amphiphilic mimetics were designed to represent the C-terminal helical segment.

Figure 7:
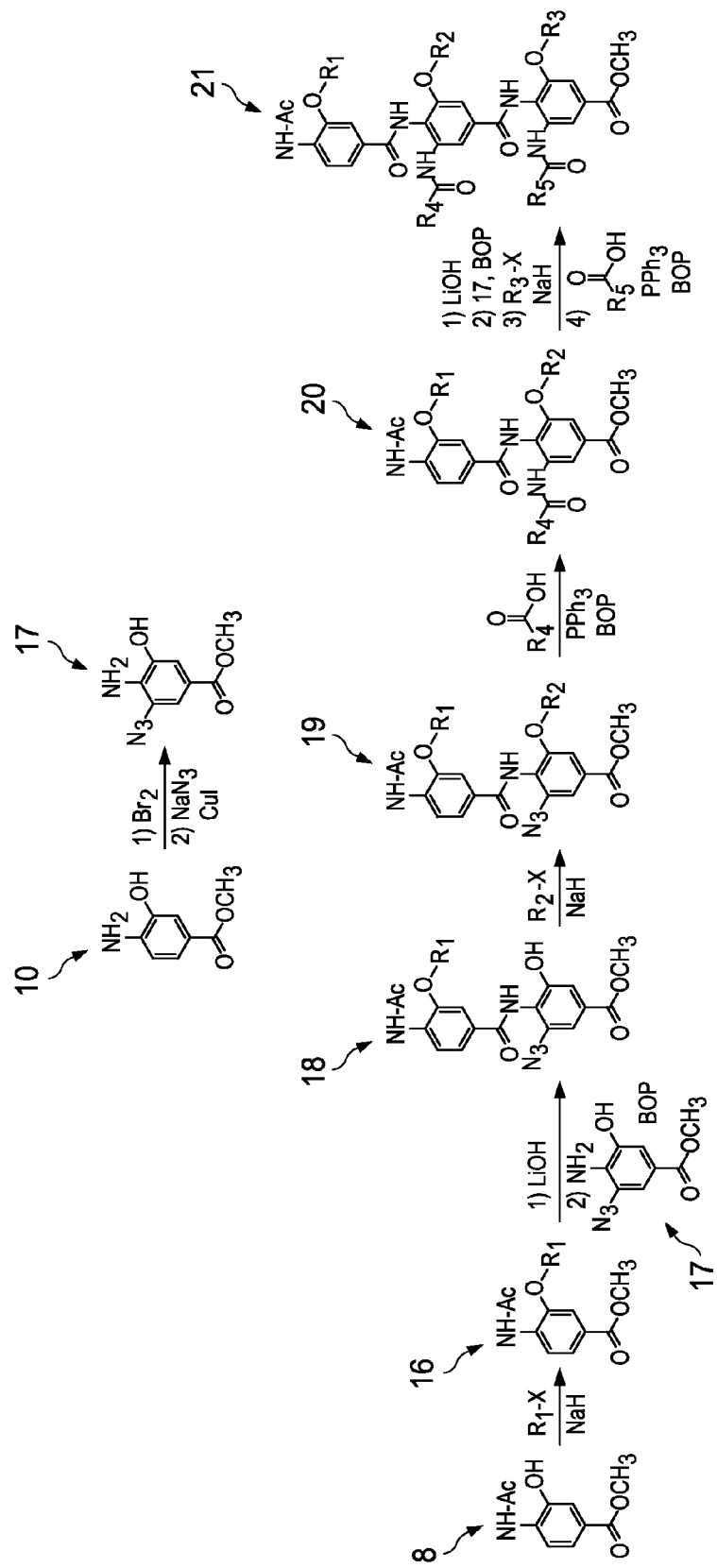
FIG. 7 is a scheme for the synthesis of peptidomimetic compounds of the present invention that represent two α-helical faces of a peptide.

FIG. 7 is a synthetic scheme for the preparation of amphiphilic α-helix mimetics of the present invention. The present invention provides amphiphilic α-helix mimetic compounds that present functional groups on both helical faces by modifying a benzamide scaffold and using a 3-azido-4-amino-5-hydroxybenzoic acid as a building block as seen in FIG. 7. The hydroxyl group at the 5-position carries a functional group corresponding to the side chain at the i+3 (or i+4) or i+7 position on one face of a helix, and the azide at the 3-position is converted to an amine to hold the functional group corresponding to the side chain at the i+2 or i+5 position on the opposite face of the helix.

Figures 8A, 8B:
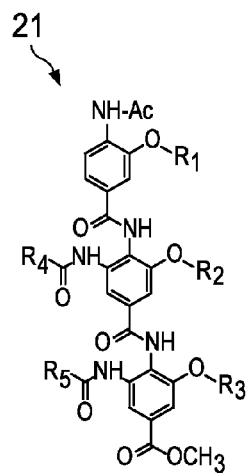
FIGS. 8A and 8B illustrate the structures of various additional peptidomimetic compounds of the present invention that represent two α-helical faces of a peptide.

In FIG. 7, the synthesis of amphiphilic α-helix mimetics started with bromination of methyl 3-hydroxy-4-aminobenzoate compound 10 followed by displacement with an azide. An alkylation reaction using methyl N-Ac-4-amino-3-hydroxybenzoate compound 8 and a variety of alkyl halides and a base like NaH introduced a functional group corresponding to the i position of the α-helix. The methyl ester compound 16 was hydrolyzed by LiOH, and the methyl 3-azido-4-amino-5-hydroxybenzoate compound 17 was coupled with BOP. A second alkylation reaction added a functional group to the free 5-hydroxyl group corresponding to the i+3 (or i+4) position. A Staudinger coupling reaction using a suitable carboxylic acid and PPh$_3$ was used to place a functional group at the i+2 position.[84] These steps were repeated to introduce functional groups corresponding to the i+7 and i+5 positions in order to complete the synthesis and to produce amphiphilic α-helix mimetic compounds as seen in FIG. 8B compounds 21A-21J. The incorporated hydrophilic functional groups not only results in a higher potency but also in a higher solubility in water. Corresponding compounds therefore require less organic solvent, which is an advantage for biological evaluation.

FIGS. 8A and 8B illustrate the structures of amphiphilic α-helix mimetic compounds of the present invention. The general amphiphilic α-helix mimetic structure is given in FIG. 8A and includes groups R1, R2 and R3 on one face and groups R4 and R5 on another face of the α-helix. FIG. 8B is a table of some of the possible substitutions for groups R1, R2, R3, R4 and R5 of the general amphiphilic α-helix mimetic compound given in FIG. 8A. The resulting amphiphilic α-helix mimetic compounds 21A-21J were analyzed by molecular modeling using MacroModel[80] (version 9, Schrodinger, New York, N.Y.), and the five functional groups in the energy-minimized structure were found to be superimposed well on the corresponding side chain groups of an ideal α-helix, as seen in FIG. 6C. The amphiphilic α-helix mimetic compounds were examined for receptor binding and their ability to stimulate cAMP production and luciferase activity to identify potent GLP-1 peptidomimetics.

The α-helix mimetic compounds 1 and 2 represent only small segments of the entire GLP-1 sequence, and other multifunctional GLP-1 peptidomimetics were constructed with the ability of occupying multiple binding sites in the receptor. For example, His$^7$ of GLP-1 is considered one of the most important amino acids for the function of GLP-1.[85] The lack of this amino acid (or its equivalent) in α-helix mimetic compounds contributes to suboptimal activity.

FIGS. 9A-9E are schematics of the peptide chains of GLP-1 where helical segments were sequentially substituted by α-helix mimetic compounds. GLP-1 mimetic compounds were constructed having the C-terminal helical peptide segment replaced, the N-terminal helical peptide segment replaced, both the C-terminal and the N-terminal helical peptide segments replaced simultaneously, or the entire GLP-1 peptide sequence replaced. The GLP-1 mimetic compounds were examined for receptor-binding affinity and ability to stimulate cAMP production and luciferase activity.

Figure 9A:
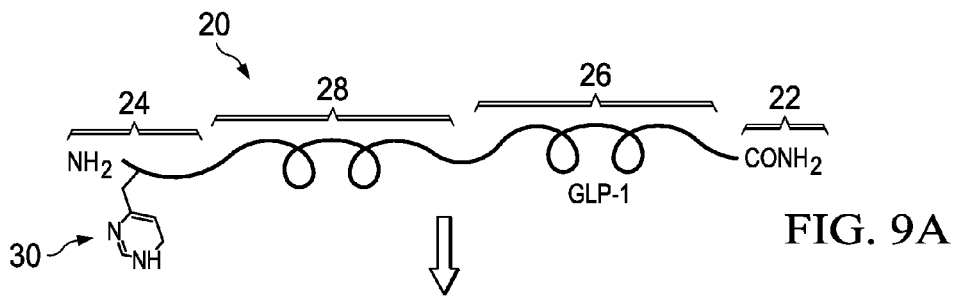
FIGS. 9A-9E are schematics of the peptide chain of GLP-1 in which increasing segments are substituted by peptidomimetic structure.

FIG. 9A illustrates the GLP-1 peptide chain 20 having a C-terminus 22 and an N-terminus 24. The GLP-1 peptide chain 20 also includes a C-terminal helical peptide segment 26, an N-terminal helical peptide segment 28 and a His$^7$ functional group 30. When the GLP-1 complementary portions of the peptide chain 20 are attached to an α-helix mimetic compound, the former provide the missing functional groups that are not present in the latter thereby increasing binding affinity to the receptor, compared to the corresponding α-helix mimetic compound per se.

Figure 9B:
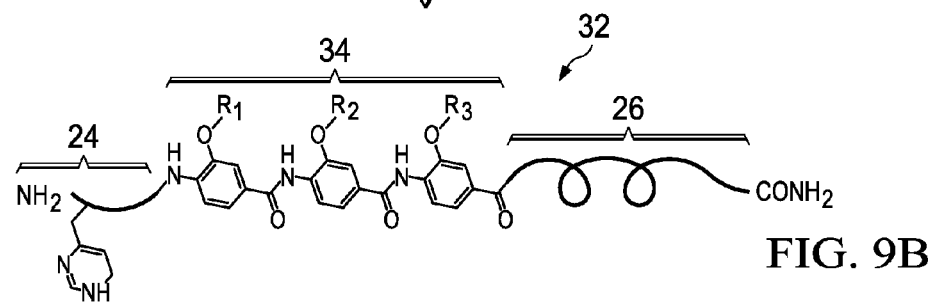

FIG. 9B illustrates the modified GLP-1 peptide chain 32 that includes a C-terminus 22 and an N-terminus 24. The modified GLP-1 peptide chain 32 also includes a C-terminal helical peptide segment 26, an α-helix mimetic moiety 34 and a His$^7$ functional group 30. The modified GLP-1 peptide chain 32 has the α-helix mimetic 34 incorporated to replace the corresponding peptide segment in 20.

Figure 9C:
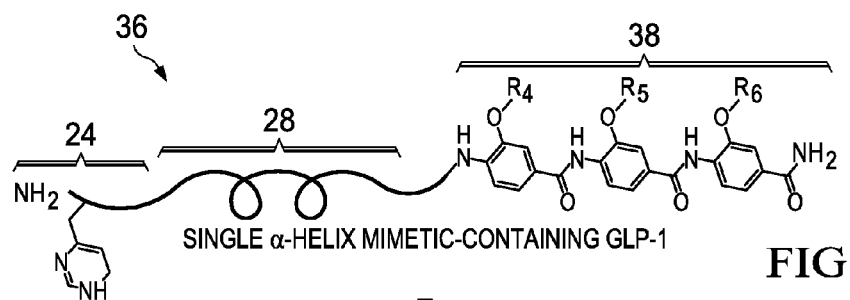
Figure 9D:
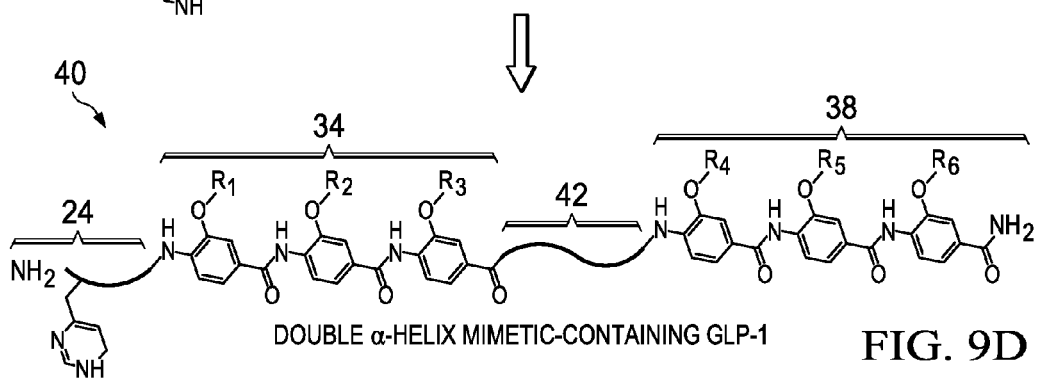

FIG. 9C illustrates the modified GLP-1 peptide chain 36 that includes a C-terminus 22 and an N-terminus 24. The modified GLP-1 peptide chain 36 also includes an α-helix mimetic moiety 38, an N-terminal helical peptide segment 28 and a His$^7$ functional group 30. The modified GLP-1 peptide chain 36 has the α-helix mimetic compound 38 incorporated to replace the corresponding peptide segment in 20. FIG. 9D illustrates the modified GLP-1 peptide chain 40 that includes a C-terminus 22 and an N-terminus 24. The modified GLP-1 peptide chain 40 also includes a C-terminal α-helix mimetic moiety 38 connected by a linker peptide chain 42 to an N-terminal α-helix mimetic moiety 34 and a His[7] functional group 30. Although the modified GLP-1 peptide chain 40 contains two α-helix mimetic compounds as well as peptide chains including the His[7] functional group 30 and the linker peptide chain 42, the majority of its sequence is converted into an organic non-peptide structure represented by the two α-helix mimetic compounds.

Figure 9E:
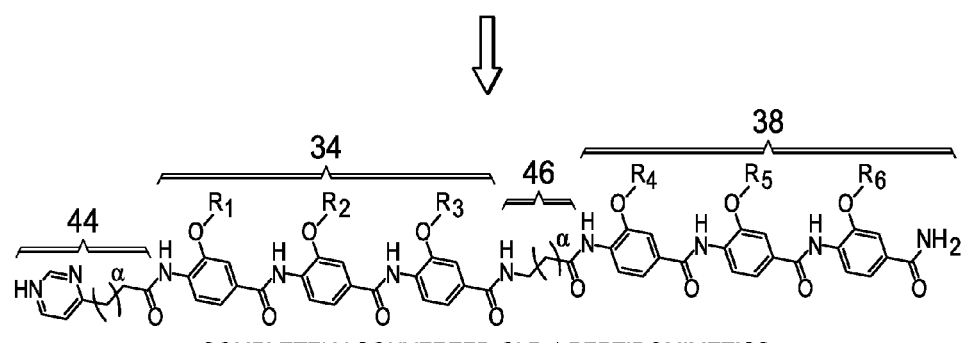

FIG. 9E illustrates a completely converted GLP-1 peptidomimetic including a GLP-1 α-helix mimetic compound 44 having a C-terminus 22 and an N-terminus 24. The GLP-1 mimetic 44 also includes a C-terminal α-helix mimetic moiety 38 connected by a non-peptide chain 46 to an N-terminal α-helix mimetic moiety 34 and a His[7] analog group. Various organic tethers (e.g., ω-amino acids in different lengths) were added to create a molecule that completely lacks peptide bonds and generally conserves GLP-1 bioactivity by retaining equivalents of the crucial pharmacophores (in particular, His[7] and the two α-helices).

One example of the chemical synthesis of the present invention is shown herein; however, the skilled artisan will be able to modify the synthetic scheme to create different functional groups and create the same product using different materials. $^1$H- and $^{13}$C-NMR spectra were recorded on a JEOL Model DELTA-270 (270 MHz) spectrometer. Tetramethylsilane (TMS) was used as the internal standard and the chemical shifts are listed in ppm. Data are expressed as follows: chemical shift (δ), multiplicity (s, singlet; d, doublet; dd, doublet of doublet; t, triplet; q, quartet; br s, broad singlet; m, multiplet), coupling constants (Hz). HRMS (FAB) were measured on JEOL HX-110 sector (EB). Silica gel used for column chromatography was Silica Gel Standard Grade (Sorbent Technologies, 230-400 mesh).

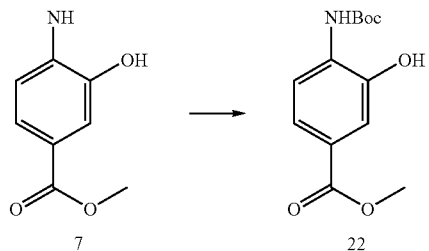

A solution of methyl 4-amino-3-hydroxy benzoate compound 7 (5 g, 30.0 mmol) and triethylamine (4.6 ml) in 100 ml $CH_2Cl_2$ was added drop-wise to a solution of di-tert-butyl dicarbonate (7.2 g, 32.9 mmol) in 20 ml $CH_2Cl_2$ at room temperature. After additional stirring for 12 hours at room temperature, the mixture was poured into water and extracted with $CH_2Cl_2$ (3×20 ml). The combined organic layers were washed with brine, dried over $Na_2SO_4$, filtered and concentrated under reduced pressure. The residue was purified by column chromatography (n-Hex/Ethyl Acetate (EA)=9/1 to n-Hex/EA=4/1) to give 7.2 g of compound 22 (90%). $^1$H NMR (270 MHz, CDCl$_3$) δ 1.56 (s, 9H), 3.85 (s, 3H), 4.21 (br s, 2H), 6.74 (d, 1H, J=8.42 Hz), 7.73 (dd, 1H, J=8.42, 1.97 Hz), 7.81 (d, 1H, J=1.97 Hz). $^{13}$C NMR (68 MHz, CDCl$_3$) δ 27.7, 51.9, 84.2, 115.4, 119.9, 124.1, 128.7, 137.2, 143.1, 151.3, 166.6. HRMS (FAB): calcd for $C_{13}H_{18}NO_5$ (M+H)$^+$ 268.1185, found 268.1190.

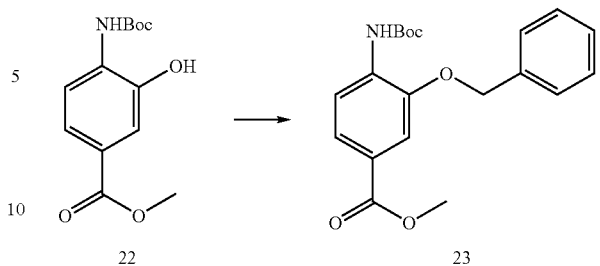

A solution of phenol compound 22 (0.20 g, 0.75 mmol) and NaH (33 mg in 60% oil, 0.82 mmol) in 10 ml dry DMF was stirred for 0.5 hours at room temperature and benzyl bromide (0.15 g, 0.82 mmol) was added slowly. The mixture was stirred for an additional hour and poured into water and extracted with ethyl acetate (3×20 ml). The combined organic layers were washed with brine, dried over $Na_2SO_4$, filtered, and concentrated under reduced pressure. The residue was purified by column chromatography (n-Hex/EA=9/1 to n-Hex/EA=4/1) to give 0.22 g of compound 23 (83%). $^1$H NMR (270 MHz, CDCl$_3$) δ 1.52 (s, 9H), 3.89 (s, 3H), 5.16 (s, 2H), 7.27 (br s, 1H), 7.35-7.45 (m, 5H), 7.62 (d, 1H, J=1.73 Hz), 7.69 (d, 1H, J=8.40, 1.73 Hz), 8.20 (d, 1H, J=8.40 Hz). $^{13}$C NMR (68 MHz, CDCl$_3$) δ 28.4, 52.1, 71.1, 81.2, 112.3, 117.1, 123.7, 123.8, 128.0, 128.6, 128.9, 133.1, 136.1, 146.1, 152.4, 166.9. HRMS (FAB): calculated for $C_{20}H_{24}NO_5$ (M+H)$^+$ 358.1654, found 358.1664.

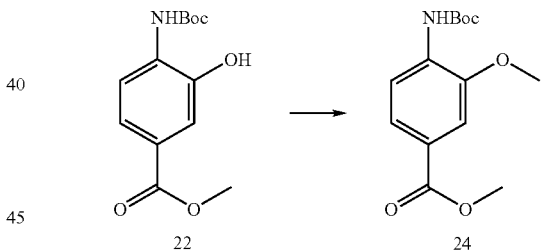

A solution of phenol compound 22 (0.2 g, 0.75 mmol) and NaH (33 mg in 60% oil, 0.82 mmol) in 10 ml dry DMF was stirred for 0.5 hour at room temperature and iodomethane (0.12 g, 0.82 mmol) was added slowly and the mixture was stirred for an additional hour. The mixture was diluted with water and extracted with ethyl acetate (3×20 ml). The combined organic layer was washed with brine, dried over $Na_2SO_4$, filtered, and concentrated under reduced pressure. The residue was purified by column chromatography (n-Hex/EA=19/1) to give 0.18 g of compound 24 (86%). $^1$H NMR (270 MHz, CDCl$_3$) δ 1.53 (s, 9H), 3.89 (s, 3H), 3.92 (s, 3H), 7.28 (br s, 1H), 7.51 (d, 1H, J=1.73 Hz), 7.67 (dd, 1H, J=8.42, 1.73 Hz), 8.17 (d, 1H, J=8.42 Hz). $^{13}$C NMR (68 MHz, CDCl$_3$) δ 28.4, 52.0, 55.9, 81.0, 110.7, 116.8, 123.5, 123.7, 132.7, 146.9, 152.5, 167.0. HRMS (FAB): calculated for $C_{14}H_{20}NO_5$ (M+H)$^+$ 282.1341, found 282.1336.

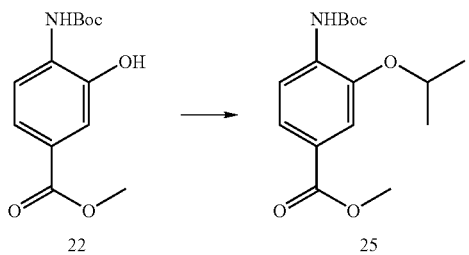

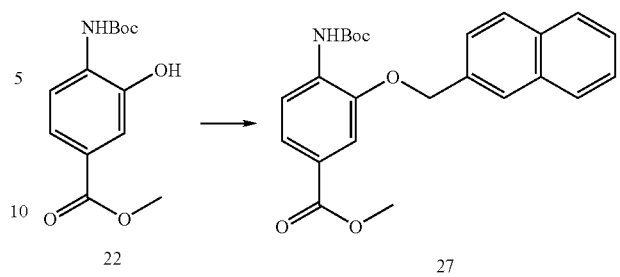

A solution of phenol compound 22 (0.2 g, 0.75 mmol) and NaH (33 mg in 60% oil, 0.82 mmol) were mixed in 10 ml dry DMF and stirred for 0.5 hours at room temperature. Then 2-bromopropane (0.22 g, 1.8 mmol) was added slowly and the mixture was stirred for an additional 24 hours, diluted with water and extracted with ethyl acetate (3×20 ml). The combined organic layer was washed with brine, dried over Na2SO4, filtered, and concentrated under reduced pressure. The residue was purified by column chromatography (n-Hex/EA=19/1) to give 0.18 g of compound 25 (78%). 1H NMR (270 MHz, CDCl$_3$) δ 1.40 (d, 6H, J=6.18 Hz), 1.55 (s, 9H), 3.89 (s, 3H), 4.70 (septet, 1H, J=6.18 Hz), 7.52 (d, 1H, J=1.73 Hz), 7.63 (dd, 1H, J=8.42, 1.73 Hz), 8.17 (d, 1H, J=8.42 Hz). 13C NMR (68 MHz, CDCl$_3$) δ 22.1, 28.4, 52.0, 71.4, 81.0, 113.0, 116.9, 123.2, 123.6, 133.6, 145.0, 152.4, 167.0. HRMS (FAB): calculated for C16H24NO5 (M+H)+ 310.1654, found 310.1668.

A solution of phenol compound 22 (0.2 g, 0.75 mmol) and NaH (33 mg in 60% oil, 0.82 mmol) was stirred in 10 ml dry DMF for 0.5 hours at room temperature and 2-bromomethylnaphthalene (0.18 g, 0.82 mmol) was added slowly. The mixture was stirred for an additional hour. The mixture was diluted with water, extracted with ethyl acetate (3×20 ml), and the combined organic layer was washed with brine, dried over Na$_2$SO$_4$, filtered and concentrated under reduced pressure. The residue was purified by column chromatography (n-Hex/EA=10/1 to n-Hex/EA=4/1) to give 0.25 g of compound 27 (82%). $^1$H NMR (270 MHz, CDCl$_3$) δ 1.50 (s, 9H), 3.87 (s, 3H), 5.30 (s, 2H), 7.30 (br s, 1H), 7.48-7.57 (m, 3H), 7.65-7.73 (m, 2H), 7.82-7.94 (m, 4H), 8.22 (d, 1H, J=8.40 Hz). $^{13}$C NMR (68 MHz, CDCl$_3$) δ 28.4, 52.1, 71.3, 81.2, 112.4, 117.1, 123.8, 123.9, 125.5, 126.5, 126.6, 127.1, 127.9, 128.1, 128.8, 133.1, 133.3, 133.5, 146.2, 152.4, 166.9. HRMS (FAB): calculated for $C_{24}H_{26}NO_5$ (M+H)$^+$ 408.1811, found 408.1833.

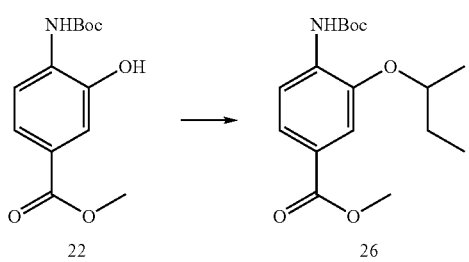

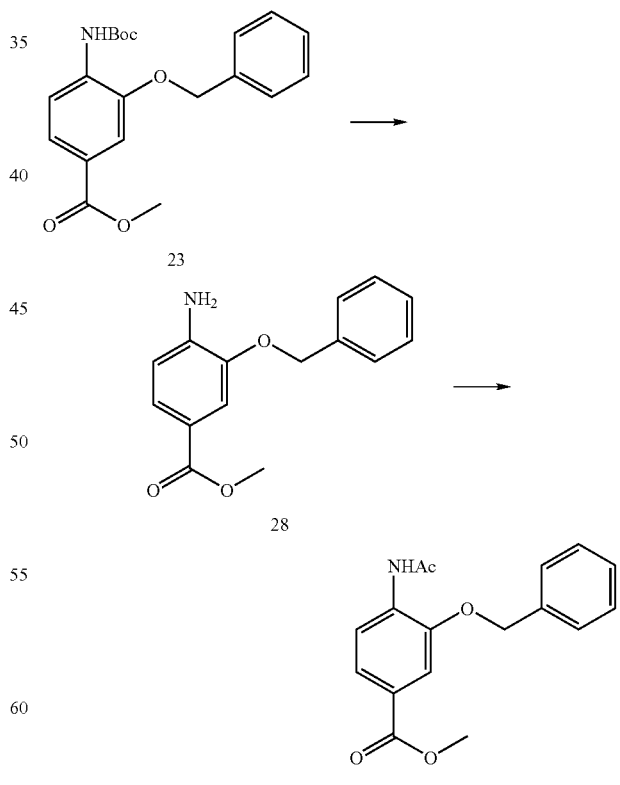

A solution of phenol compound 22 (0.2 g, 0.75 mmol) and NaH (33 mg in 60% oil, 0.82 mmol) was stirred in 10 ml dry DMF for 0.5 hour at room temperature and then 2-bromobutane (0.25 g, 1.8 mmol) was added slowly. The mixture was stirred for an additional 24 hours, diluted with water, extracted with ethyl acetate (3×20 ml), the combined organic layer was washed with brine, dried over Na$_2$SO$_4$, filtered, and concentrated under reduced pressure. The residue was purified by column chromatography (n-Hex/EA=19/1) to give 0.18 g of compound 26 (73%). $^1$H NMR (270 MHz, CDCl$_3$) δ 1.00 (t, 3H, J=7.40), 1.34 (d, 3H, J=6.18 Hz), 1.54 (s, 9H), 1.62-1.90 (m, 2H), 3.89 (s, 3H), 4.46 (sextet, 1H, J=6.18 Hz), 7.51 (d, 1H, J=1.73 Hz), 7.64 (dd, 1H, J=8.40, 1.73 Hz), 8.17 (d, 1H, J=8.40 Hz). $^{13}$C NMR (68 MHz, CDCl$_3$) δ 9.9, 19.3, 28.4, 29.2, 52.0, 76.5, 81.0, 113.1, 117.0, 123.2, 123.6, 133.6, 145.2, 152.5, 167.0. HRMS (FAB): calculated for $C_{17}H_{26}NO_5$ (M+H)$^+$ 324.1811, found 324.1810.

To a solution of compound 23 (2 g, 5.60 mmol) in 16 ml CH$_2$Cl$_2$, 4 ml trifluoroacetic acid was added in an ice-water bath. The reaction solution was stirred at room temperature for 2 hours and the excess trifluoroacetic acid and $CH_2Cl_2$ were removed under reduced pressure. The residue was dissolved in $CH_2Cl_2$, washed with saturated $NaHCO_3$ and brine and dried over $Na_2SO_4$. The organic layer was concentrated under reduced pressure to give the corresponding aniline, which was used in the next step without purification. A solution of aniline and DMAP (68 mg, 0.56 mmol) in acetic anhydride was stirred at room temperature for 12 hours. The reaction mixture was poured into water and extracted with $CH_2Cl_2$. The organic layer was washed with 1N HCl, water, and saturated $NaHCO_3$ solution, dried and concentrated to give compounds 28 and 29. The mixture was purified by column chromatography (n-Hex/EA=4/1 to n-Hex/EA=2/1) to give 1.62 g of compound 29 (97%). $^1$H NMR (270 MHz, $CDCl_3$) δ 2.17 (s, 3H), 3.89 (s, 3H), 5.16 (s, 2H), 7.36-7.46 (m, 5H), 7.65 (d, 1H, J=1.73 Hz), 7.69 (dd, 1H, J=8.40, 1.73 Hz), 7.92 (br s, 1H), 8.48 (d, 1H, J=8.67 Hz). $^{13}$C NMR (68 MHz, $CDCl_3$) δ 25.1, 52.2, 71.3, 112.4, 118.9, 123.8, 125.0, 128.0, 128.7, 128.9, 132.4, 135.9, 146.4, 166.7, 168.5. HRMS (FAB): calculated for $C_{17}H_{18}NO_4$ $(M+H)^+$ 300.1236, found 300.1235.

Compound 29 (1.62 g, 5.68 mmol) was dissolved in 1N NaOH (10 ml)/MeOH (20 ml)/THF (40 ml) and stirred at 60° C. for 2 hours. Methanol and THF were carefully concentrated and the mixture was acidified with 1N HCl, and the suspension was extracted with ethyl acetate, dried over $Na_2SO_4$ and evaporated under reduced pressure to give the corresponding acid, which was used in the next step without purification. The solution of acid, DMF (cat.) and $SOCl_2$ (2.7 g, 22.7 mmol) in 20 ml THF was heated at 60° C. for 2 hours. After the reaction mixture was cooled, the reaction mixture was concentrated under reduced pressure. The residue was dissolved in $CH_2Cl_2$ and cooled at 0° C. To this acid chloride DIPEA (5.14 g, 39.8 mmol) and methyl 4-amino-3-hydroxy-benzoate compound 7 (1.42 g, 8.51 mmol) were added and stirred at room temperature for 2 hours. The reaction mixture was concentrated under reduced pressure and the residue was purified by column chromatography (n-Hex/EA=2/1 to n-Hex/EA=1/1) to give 2.02 g of compound 30 (82% in three steps). $^1$H NMR (270 MHz, $CDCl_3$) δ 2.20 (s, 3H), 3.85 (s, 3H), 4.11 (br s, 2H), 5.20 (s, 2H), 6.80 (d, 1H, J=8.91 Hz), 7.36-7.47 (m, 5H), 7.74-7.82 (m, 3H), 7.88 (dd, 1H, J=8.42, 1.73 Hz), 7.99 (br s, 1H), 8.56 (d, 1H, J=8.42 Hz). $^{13}$C NMR (68 MHz, $CDCl_3$) δ 25.2, 51.9, 71.4, 112.9, 115.6, 119.0, 120.3, 123.5, 124.59, 124.63, 128.0, 128.8, 128.9, 129.0, 133.4, 135.7, 136.9, 143.3, 146.5, 164.1, 166.6, 168.7. HRMS (FAB): calculated for $C_{24}H_{23}N_2O_6$ $(M+H)^+$ 435.1556, found 435.1568.

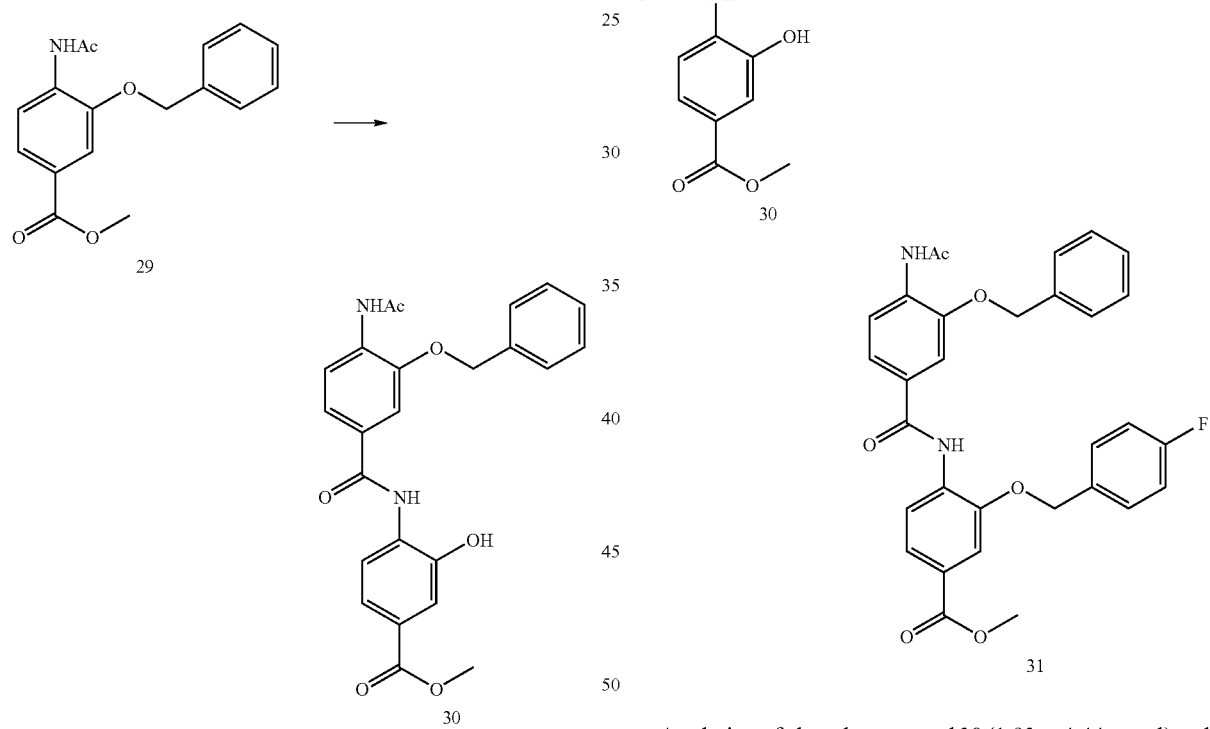

A solution of phenol compound 30 (1.93 g, 4.44 mmol) and NaH (0.20 g in 60% oil, 4.88 mmol) in 50 ml dry DMF was stirred for 0.5 hour at room temperature and then 4-fluorobenzyl bromide (1.01 g, 5.33 mmol) was added slowly. The mixture was stirred for an additional 2 hours, diluted with water, and extracted with ethyl acetate (3×40 ml). The combined organic layer was washed with brine, dried ($Na_2SO_4$) and concentrated under reduced pressure. The residue was purified by column chromatography (n-Hex/EA=4/1 to n-Hex/EA=2/1) to give 1.86 g of compound 31 (77%). $^1$H NMR (270 MHz, $CDCl_3$) δ 2.18 (s, 3H), 3.91 (s, 3H), 5.11 (s, 2H), 5.17 (s, 2H), 7.09 (t, 2H, J=8.42 Hz), 7.27 (dd, 1H, J=8.64, 1.73 Hz), 7.35-7.48 (m, 7H), 7.57 (d, 1H, J=1.73 Hz), 7.67 (d, 1H, J=1.73 Hz), 7.75 (dd, 1H, J=8.42, 1.73 Hz), 8.46 (d, 1H, J=8.42 Hz), 8.62 (d, 1H, J=8.64 Hz), 8.72 (br s, 1H). $^{13}$C NMR (68 MHz, $CDCl_3$) δ 25.1, 52.2, 70.8, 71.3, 111.0, 112.4, 116.0 (d, J=21.3 Hz), 118.8, 119.1, 119.6, 124.1, 125.1, 128.0, 128.8, 129.0, 129.4, 129.8 (d, J=8.3 Hz), 131.7, 132.5, 135.7, 146.7, 147.1, 162.9 (d, J=248.1 Hz), 164.5, 166.7, 168.6. HRMS (FAB): calculated for $C_{31}H_{28}FN_2O_6$ $(M+H)^+$ 543.1931, found 543.1942.

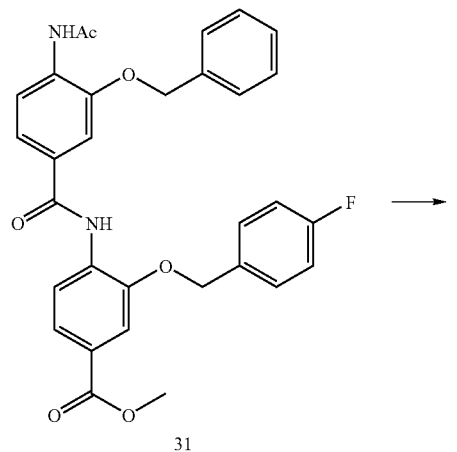

31

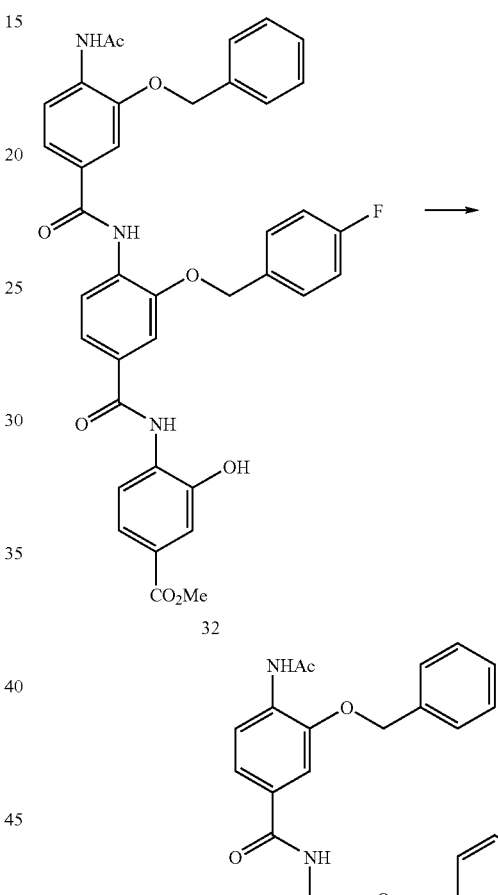

32

Dimer compound 31 (1.86 g, 3.43 mmol) was dissolved in 1N NaOH (10 ml)/MeOH (20 ml)/THF (40 ml) and heated at 60° C. for 2 hours. Methanol and THF were carefully concentrated and the mixture was acidified with 1N HCl, and the suspension was extracted with ethyl acetate, dried over $Na_2SO_4$ and evaporated under reduced pressure to give the corresponding acid, which was used in the next step without purification. The solution of acid, BOP (1.92 g, 4.11 mmol) and DIPEA (1.11 g, 8.57 mmol) in $CH_2Cl_2$ was stirred at 0° C. for 0.5 hour. Methyl 4-amino-3-hydroxybenzoate compound 7 (0.57 g, 2.86 mmol) was added and stirred at room temperature for 2 hours. The mixture was poured into water and extracted with $CH_2Cl_2$ (3×40 ml), and the combined organic layer was washed with brine, dried over $Na_2SO_4$, filtered, and concentrated under reduced pressure. The residue was purified by column chromatography (dichloromethane/ethyl ether=19/1) to give 1.72 g of compound 32 (74% in two steps). $^1$H NMR (270 MHz, $CDCl_3$) δ 2.19 (s, 3H), 3.85 (s, 3H), 4.15 (br s, 2H), 5.19 (s, 2H), 5.20 (s, 2H), 6.82 (d, 2H, J=8.88 Hz), 7.10 (t, 2H, J=8.65 Hz), 7.30 (dd, 1H, J=8.40, 1.73 Hz), 7.34-7.50 (m, 7H), 7.59 (d, 1H, J=1.73 Hz), 7.75-7.81 (m, 3H), 7.88 (m, 1H), 8.48 (d, 1H, J=8.40 Hz), 8.70 (d, 1H, J=8.40 Hz), 8.79 (br s, 1H). $^{13}$C NMR (68 MHz, $CDCl_3$) δ 25.1, 51.9, 70.9, 71.3, 111.1, 112.9, 115.6, 116.1 (d, J=21.8 Hz), 119.0, 119.1, 119.6, 120.4, 123.6, 124.7, 124.8, 128.0, 128.8, 129.0, 129.3, 129.8 (d, J=8.3 Hz), 131.5 (d, J=3.6 Hz), 131.8, 133.5, 135.7, 136.9, 143.2, 146.9, 147.1, 162.7 (d, J=216.4 Hz), 164.1, 164.5, 166.6, 168.6. HRMS (FAB): calculated for $C_{38}H_{33}FN_3O_8$ $(M+H)^+$ 678.2252, found 678.2262.

33

A solution of phenol compound 32 (1.72 g, 2.54 mmol) and NaH (0.11 g in 60% oil, 2.79 mol) in 50 ml dry DMF was stirred for 0.5 hours at room temperature and then 4-fluorobenzyl bromide (3.05 mmol) was added slowly. The mixture was stirred for an additional 2 hours. The mixture was diluted with water and extracted into ethyl acetate (3×40 ml). The combined organic layer was washed with brine, dried (Na$_2$SO$_4$) and concentrated under reduced pressure. The residue was purified by column chromatography (dichloromethane/ethyl ether=19/1) to give 1.20 g of compound 33 (61%). $^1$H NMR (270 MHz, DMSO-d6) δ 2.15 (s, 3H), 3.86 (s, 3H), 5.23 (s, 2H), 5.27 (s, 2H), 5.29 (s, 2H), 7.12-7.74 (m, 19H), 8.03-8.15 (m, 3H), 9.34 (br s, 1H), 9.51 (br s, 1H), 9.59 (br s, 1H) $^{13}$C NMR (68 MHz, CDCl$_3$) δ 24.6, 52.7, 70.1, 70.6, 112.4, 112.5, 113.6, 115.8 (d, J=21.8 Hz), 120.8, 120.9, 121.8, 123.0, 123.1, 123.4, 126.5, 128.0, 128.5, 129.0, 130.0, 130.3 (d, J=7.8 Hz), 131.2, 131.5, 132.0, 132.7, 133.38, 133.42, 133.48, 137.2, 148.6, 149.9, 150.1, 162.4 (d, J=243.4 Hz), 164.9, 166.4, 169.5. HRMS (FAB): calculated for C$_{45}$H$_{38}$F$_2$N$_3$O$_8$ (M+H)$^+$ 786.2627, found 786.2598.

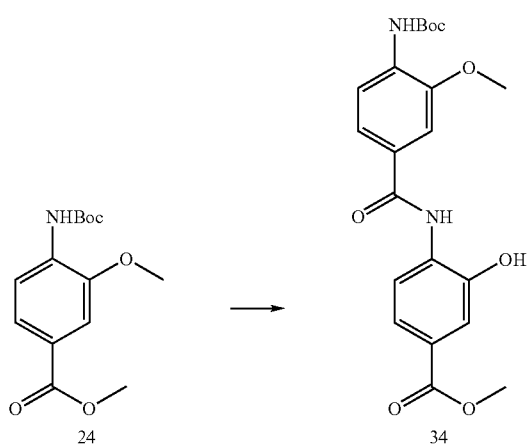

Compound 24 (2 g, 7.11 mmol) was dissolved in 1N NaOH (10 ml)/MeOH (20 ml)/THF (40 ml) and heated at 60° C. for 2 hours. Methanol and THF were carefully concentrated and the mixture was acidified with 1N HCl. The suspension was extracted with ethyl acetate, dried over Na2SO4 and evaporated under reduced pressure to give the corresponding acid, which was used in the next step without purification. The solution of acid, DMF (cat.) and SOCl2 (3.38 g, 28.4 mmol) in 20 ml THF was heated at 60° C. for 2 hours. The reaction mixture was cooled and concentrated under reduced pressure. The residue was dissolved in CH$_2$Cl$_2$ and cooled at 0° C. To this acid chloride DIPEA (9.19 g, 71.1 mmol) and methyl 4-amino-3-hydroxybenzoate compound 7 (1.42 g, 8.53 mmol) were added and stirred at room temperature for 2 hours. The reaction mixture was concentrated under reduced pressure and purified by column chromatography (n-Hex/EA=4/1 to n-Hex/EA=2/1) to give 2.28 g of compound 34 (77% in three steps). $^1$H NMR (270 MHz, CDCl$_3$) δ 1.55 (s, 3H), 3.84 (s, 3H), 3.95 (s, 3H), 4.16 (br s, 2H), 6.80 (d, 1H, J=8.88 Hz), 7.37 (br s, 1H), 7.63 (d, 1H, J=1.73 Hz), 7.74-7.82 (m, 2H), 7.85 (dd, 1H, J=8.42, 1.73 Hz), 8.56 (d, 1H, J=8.67 Hz). $^{13}$C NMR (68 MHz, CDCl$_3$) δ 28.4, 51.8, 56.1, 81.3, 111.2, 115.6, 116.9, 120.2, 122.1, 124.4, 124.7, 128.8, 133.8, 137.0, 143.4, 147.1, 152.3, 164.4, 166.6. HRMS (FAB): calculated for C$_{21}$H$_{25}$N$_2$O$_7$ (M+H)+ 417.1662, found 417.1645.

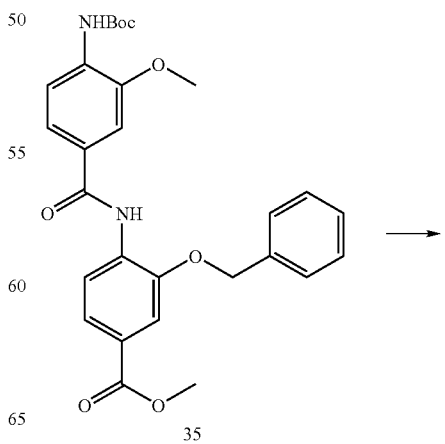

A solution of compound 34 (2.28 g, 5.48 mmol) and NaH (0.24 g in 60% oil, 6.02 mol) in 50 ml dry DMF was stirred for 0.5 hour at room temperature and benzyl bromide (1.13 g, 6.57 mmol) was added slowly. The mixture was stirred for an additional 2 hours, diluted with water and extracted with ethyl acetate (3×40 ml). The combined organic layer was washed with brine, dried (Na2SO4) and concentrated under reduced pressure. The residue was purified by column chromatography (n-Hex/EA=4/1 to n-Hex/EA=2/1) to give 2.21 g of compound 35 (80%). $^1$H NMR (270 MHz, CDCl$_3$) δ 1.54 (s, 3H), 3.84 (s, 3H), 3.92 (s, 3H), 5.20 (s, 2H), 7.24-7.52 (m, 8H), 7.71 (d, 1H, J=1.73 Hz), 7.77 (dd, 1H, J=8.42, 1.73 Hz), 8.13 (d, 1H, J=8.42 Hz), 8.65 (d, 1H, J=8.67 Hz), 8.78 (br s, 1H). $^{13}$C NMR (68 MHz, CDCl$_3$) δ 28.4, 52.2, 55.9, 71.5, 81.1, 109.3, 112.3, 117.0, 118.6, 119.6, 124.0, 125.0, 128.0, 128.1, 128.8, 129.0, 132.0, 132.7, 135.9, 146.9, 147.5, 152.4, 164.7, 166.8. HRMS (FAB): calculated for C$_{28}$H$_{31}$N$_2$O$_7$ (M+H)+ 507.2131, found 507.2133.

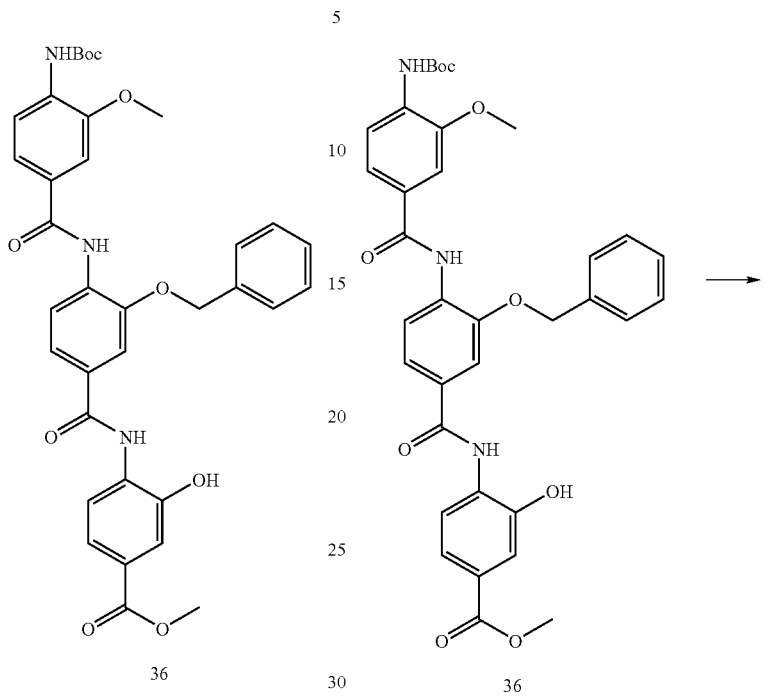

Compound 35 (2.21 g, 4.49 mmol) was dissolved in 1N NaOH (10 ml)/MeOH (20 ml)/THF (40 ml) and heated at 60° C. for 2 hours. Methanol and THF were carefully concentrated and the mixture was acidified with 1N HCl. The suspension was extracted with ethyl acetate, dried over Na2SO4 and evaporated under reduced pressure to give the corresponding acid, which was used in the next step without purification. The solution of acid, DMF (cat.) and SOCl2 (2.14 g, 17.9 mmol) in 20 ml THF was refluxed for 2 hours. The reaction mixture was cooled and concentrated under reduced pressure. The residue was dissolved in $CH_2Cl_2$ and cooled at 0° C. To this acid chloride, DIPEA (5.80 g, 44.9 mmol) and methyl 4-amino-3-hydroxybenzoate 5 (0.90 g, 5.38 mmol) were added and stirred at room temperature for 2 hours. The reaction mixture was concentrated under reduced pressure and purified by column chromatography (n-Hex/EA=9/1 to n-Hex/EA=2/1) to give 2.19 g of compound 36 (76% in three steps). $^1$H NMR (270 MHz, $CDCl_3$) δ 1.55 (s, 3H), 3.86 (s, 6H), 5.24 (s, 3H), 6.82 (d, 1H, J=6.87 Hz), 7.78-7.86 (m, 3H), 7.69 (dd, 1H, J=8.67, 1.73 Hz), 8.15 (d, 1H, J=8.42 Hz), 8.73 (d, 1H, J=8.64 Hz), 8.85 (br s, 1H). $^{13}$C NMR (68 MHz, $CDCl_3$) δ 28.4, 51.9, 55.9, 71.6, 81.2, 109.3, 112.8, 115.6, 117.0, 118.8, 119.6, 120.2, 123.4, 124.7, 124.8, 127.9, 128.0, 128.9, 129.0, 132.2, 133.6, 135.7, 136.9, 143.4, 147.0, 147.5, 152.4, 164.2, 164.7, 166.6. HRMS (FAB): calculated for $C_{35}H_{36}N_3O_9$ (M+H)+ 642.2452, found 642.2432.

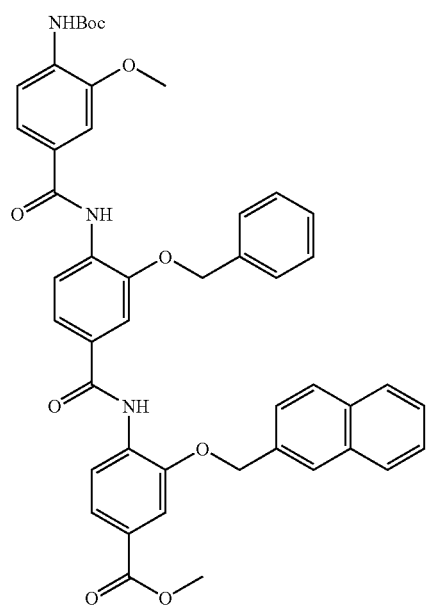

A solution of trimer compound 36 (2.19 g, 3.41 mmol) and NaH (0.15 g in 60% oil, 3.75 mmol) in 50 ml dry DMF was stirred for 0.5 hour at room temperature. 2-bromomethyl naphthalene (0.91 g, 4.10 mmol) was added slowly to the solution. The solution was stirred for an additional 2 hours, diluted with water and extracted with ethyl acetate (3×40 ml). The combined organic layer was washed with brine, dried (Na2SO4) and concentrated under reduced pressure. The residue was purified by column chromatography (n-Hex/EA=4/1 to n-Hex/EA=1/1) to give 2.29 g of compound 37 (86%). $^1$H NMR (270 MHz, CDCl$_3$) δ 1.55 (s, 3H), 3.82 (s, 3H), 3.91 (s, 3H), 5.03 (s, 2H), 5.37 (s, 2H), 7.22-7.60 (m, 13H), 7.74-7.94 (m, 6H), 8.11 (d, 1H, J=8.40 Hz), 8.58 (d, 1H, J=8.40 Hz), 8.66 (d, 1H, J=8.40 Hz), 8.70 (br s, 1H), 8.84 (br s, 1H). $^{13}$C NMR (68 MHz, CDCl$_3$) δ 28.5, 52.4, 56.0, 71.5, 71.9, 81.3, 109.3, 110.8, 112.6, 117.1, 118.9, 119.0, 119.8, 120.2, 124.2, 125.3, 126.8, 126.9, 127.2, 128.1, 128.2, 129.0, 129.1, 129.4, 132.1, 132.2, 132.8, 133.4, 133.5, 135.9, 147.1, 147.5, 147.6, 152.6, 164.6, 164.8, 166.9. HRMS (FAB): calculated for $C_{46}H_{44}N_3O_9$ (M+H)+ 782.3078, found 782.3065.

The synthesis of benzamides includes an alkylation reaction to place a functional group corresponding to an amino acid in a helix. The reaction is given below:

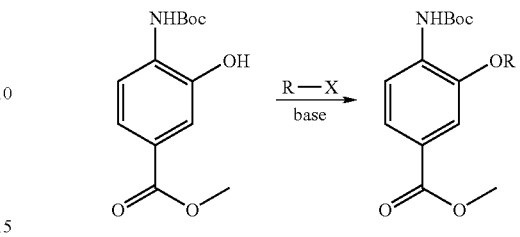

The hydroxyl group in methyl 4-(t-butoxycarbonylamino)-3-hydroxybenzoate was reacted with a series of alkyl halides in the presence of bases as described in Table 1.

| Product | R-X | Reaction Condition | Yield (%)$^a$ |
|---|---|---|---|
| 2a | PhCH$_2$Br | K$_2$CO$_3$ (1.2 eq), acetone, reflux, 24 h | 33 |
| 2a | PhCH$_2$Br | NaH (1.1 eq), DMF, rt, 1.5 h | 83 |
| 2a | PhCH$_2$Br | NaH (1.1 eq), THF, reflux, 2.5 h | 53 |
| 2a | PhCH$_2$Br | NaOMe (1.2 eq), DMF, rt, 1.5 h | 73 |
| 2a | PhCH$_2$Br | NaOMe (1.2 eq), THF, reflux, 2.5 h | 72 |
| 2a | PhCH$_2$Br | DBU (5 eq), DMF, rt, 12 h | 19 |
| 2b | CH$_3$I | NaH (1.1 eq), DMF, rt, 1.5 h | 86 |
| 2c | iPrBr | NaH (1.1 eq), DMF, rt, 24 h | 78 |
| 2d | sec-BuBr | NaH (1.1 eq), DMF, rt, 24 h | 73 |
| 2e | 2-(bromomethyl)naphthalene | NaH (1.1 eq), DMF, rt, 1.5 h | 83 |

Several bases and solvents were screened to optimize the reaction condition and the use of NaH in DMF at room temperature resulted in high yield. Sodium methoxide also provided good yield and less byproducts than NaH, whereas $K_2CO_3$ and a hindered organic base, 1,8-diazabicyclo[5.4.0]undec-7-ene (DBU) were found to be inefficient. As a solvent, DMF appears to be more effective than THF since the benzylation in THF required refluxing even with the most efficient base found (NaH), whereas DMF provided higher yield at much lower ambient temperature. The alkylation reaction was carried out with various alkyl halides under the optimized reaction condition, resulting in the desired products in high yield (70-80%). Methyl and benzyl halides mimicking Ala and Phe, respectively, gave slightly better yields compared to aliphatic alkyl halides, such as 2-bromopropane and 2-bromobutane representing Val and Ile, respectively. 2-Naphthylmethyl group was introduced in an attempt to replace the indole side chain of Trp. The coupling reaction was performed using an unalkylated hydroxybenzoate instead of the alkylated. Using $SOCl_2$ or BOP as a coupling reagent, the alkoxybenzamide was synthesized in high yield (70-80%), and a subsequent alkylation produced the desired dialkoxybenzamide which possesses two functional groups in a helix.

Figure 10:
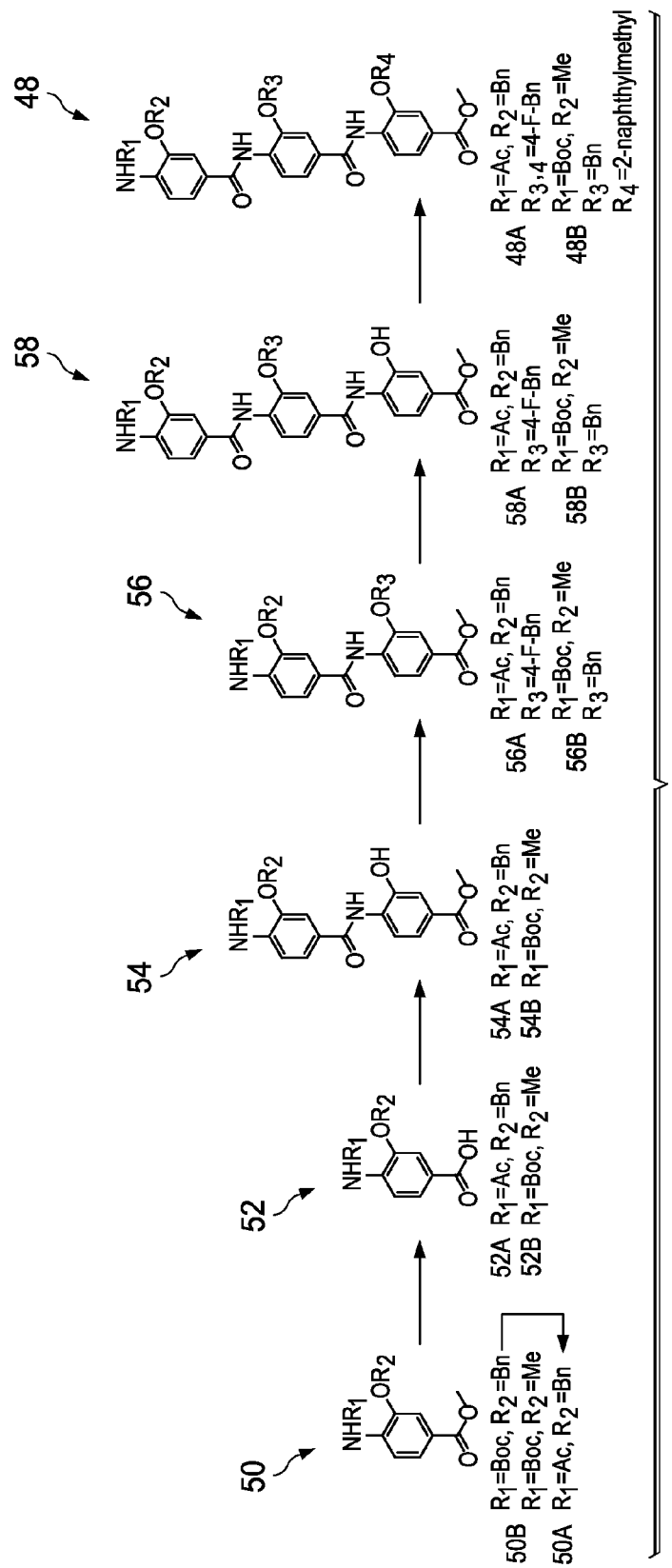
FIG. 10 is a scheme for the synthesis of additional α-helix peptidomimetic compounds.

FIG. 10 is a scheme for the synthesis of two tris-benzamides 48A and 48B, where tris-benzamides 48A includes a R1 that is an Acetyl (Ac) group, R2 is a Benzyl (Bn) group and R3 and R4 are 4-fluorobenzyl groups and tris-benzamides 48B includes a R1 is a t-butoxycarbonyl (Boc) group, R2 is a Methyl (Me) group and R3 is a Benzyl (Bn) group and R4 is a 2-naphthylmethyl.

After the alkylation of the hydroxybenzoate compound 50, the methyl ester was hydrolyzed using NaOH, and methyl 4-amino-3-hydroxybenzoate was coupled to the benzoic acid (compound 52A where R1 is an Acetyl (Ac) group and R2 as a Benzyl (Bn) group and compound 52B where R1 as a t-butyloxycarbonyl (Boc) group and R as a Methyl (Me) group) using $SOCl_2$, resulting in a bis-benzamide containing one alkyl group (compound 54A where R1 as an Acetyl (Ac) group and R2 as a Benzyl (Bn) group and compound 54B where R1 as a t-butyloxycarbonyl (Boc) group and R2 as a Methyl (Me) group) corresponding to the i position of a helix. The alkylation and coupling reactions were repeated twice to place two other functional groups corresponding to the i+4 (or i+3) and i+7 positions as seen in compound 56A where R1 is an Acetyl (Ac) group, R2 is a Benzyl (Bn) group and R3 is a 4-fluorobenzyl group; compound 56B where R1 is a t-butyloxycarbonyl (Boc) group, R2 is a Methyl (Me) group and R3 is a Benzyl (Bn) group; compound 58A where R1 is an Acetyl (Ac) group, R2 is a Benzyl (Bn) group and R3 is a 4-fluorobenzyl group; and compound 58B where R1 is a t-butoxycarbonyl (Boc) group, R2 is a Methyl (Me) group and R3 is a Benzyl (Bn) group.

Figure 11A:
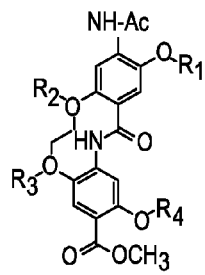
FIG. 11A is an image of a bis-benzamide structure that is used to generate α-helix peptidomimetic compounds of the present invention.
Figure 11B:
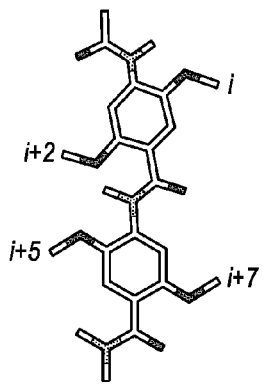
FIGS. 11B and 11C are images of the energy-minimized structure of an α-helix peptidomimetic compound.

The present invention also provides an amphiphilic α-helix mimetic using a different template. The template used to mimic an amphiphilic α-helix, is a bis-benzamide structure that constitutes two 4-amino-2,5-dihydroxybenzoic acid moieties as seen in FIGS. 11A and 11B. Analogous to the building block of the original amphiphilic α-helix mimetic (3,4-diamino-5-hydroxybenzoic acid), the building block of the alternative scaffold (4-amino-2,5-dihydroxybenzoic acid) also has two hydroxyl groups at the 2- and 5-positions to present two functional groups found on opposite faces of an α-helix. However, the structure of the alternative scaffold is quite different compared to the original one. Its structure was again analyzed by molecular modeling using MacroModel (a Monte Carlo conformational search).

Figure 11C:
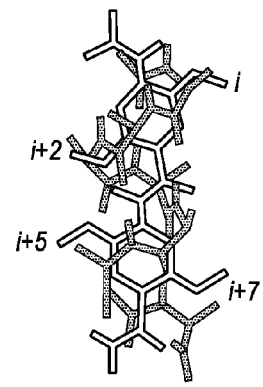

FIG. 11C is an image of the energy minimized structure of the lowest energy conformation was analyzed by molecular modeling using MacroModel. The energy minimized structure of the lowest energy conformation showed significantly enhanced rigidity in the structure, resulting from two hydrogen bonds made by the benzamide proton and two nearby alkoxy groups (R2 and R3), one from the 2-position in the upper benzene ring and the other from the 5-position in the lower benzene ring. These hydrogen bonds tightly secure the relative orientation of two benzene rings, and direct two alkyl groups (R2 and R3) at the 2-position in the upper ring and the 5-position in the lower ring on the same side of the structure. This results in the remaining two alkyl groups (R1 and R4) at the 5-position in the upper ring and the 2-position in the lower ring being on the same side, opposite to the former two groups (R2 and R3). Superimposition of this alternative amphiphilic α-helix mimetic over an α-helix reveals that 4 alkyl groups (R1-4) in the mimetic represent 4 side chains of the helix extremely well as seen in FIG. 11C. The hydrogen bonds increase the distance between two alkyl groups (R1 and R4) at the 5-position in the upper ring and the 2-position in the lower ring, well representing the i and i+7 positions. On the other hand, the two alkyl groups (R2 and R3) being in close proximity due to the hydrogen bonds overlay well to the side chain groups at the i+2 and i+5 positions on the opposite face of a helix.

Figure 12:
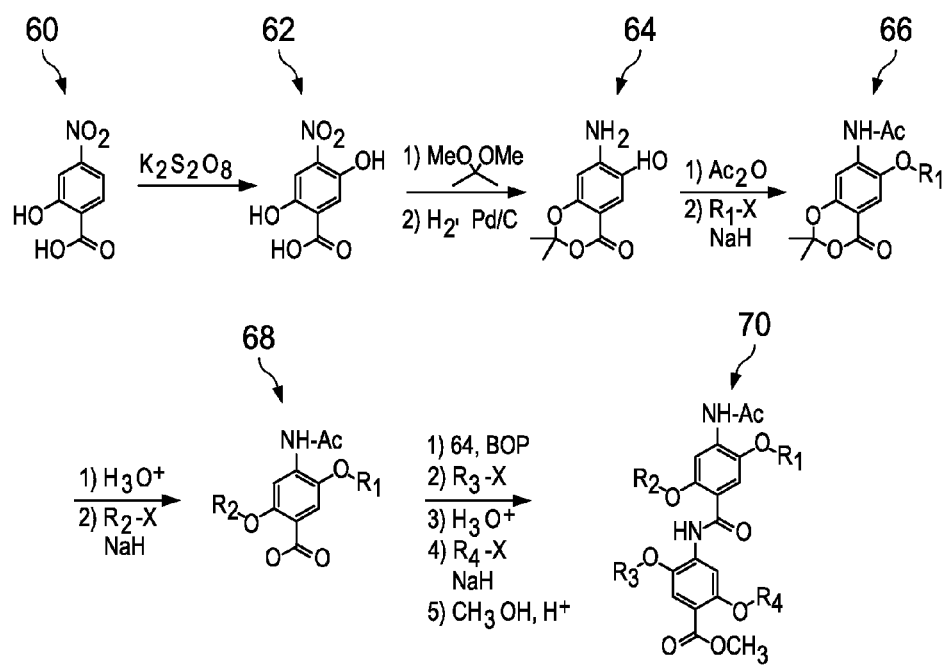
FIG. 12 is a scheme for the synthesis of another α-helix peptidomimetic compound of the present invention.
Figure 13A:
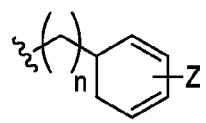
FIGS. 13A-13N are images of various structures of substituted groups that may be placed at the R positions of the α-helix peptidomimetic compounds.
Figure 13B:
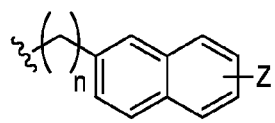
Figure 13C:
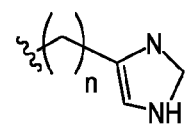
Figure 13D:
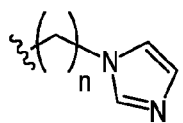
Figure 13E:
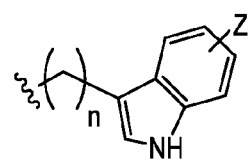
Figure 13F:
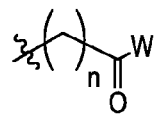
Figure 13G:
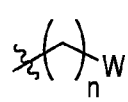
Figure 13H:
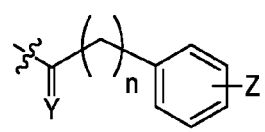
Figure 13I:
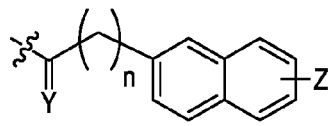
Figure 13J:
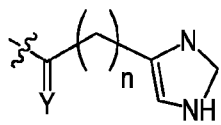
Figure 13K:
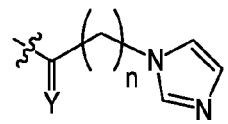
Figure 13L:
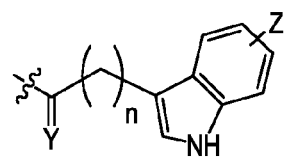
Figure 13M:
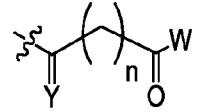
Figure 13N:
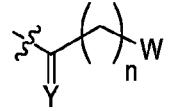

FIG. 12 is a scheme for the synthesis of the alternative amphiphilic α-helix mimetics of the present invention. The 4-aminosalicylic acid compound 60 was protected as N-Boc methyl ester compound 62, which was oxidized with persulfate. The Boyland-Sim oxidation reaction produced methyl N-Boc-4-amino-2,5-dihydroxybenzoate compound 62, and the N-Boc protecting group was removed by TFA. Then, the 4-amino and 5-hydroxyl groups were protected as a ketal by the treatment of 2,2-dimethoxypropane. After the 4-amino group of the building block compound was acetylated, an alkyl group (R1) was introduced to the free 5-hydroxyl group using various alkyl halides and a base (NaH or NaOMe) for the side chain functionality at the i position. Subsequently, the ketal was removed by an acidic treatment and a second alkylation reaction was carried out to place a functional group (R2) for the i+2 position. The second building block (compound 64) was coupled using BOP or PyBrOP to form a bis-benzamide. The steps (alkylation, deprotection, and another alkylation) were repeated to prepare the compounds 64, 66, 68 and 70.

For example, the present invention includes an oligo-benzamide peptidomimetic compound having the following formula:

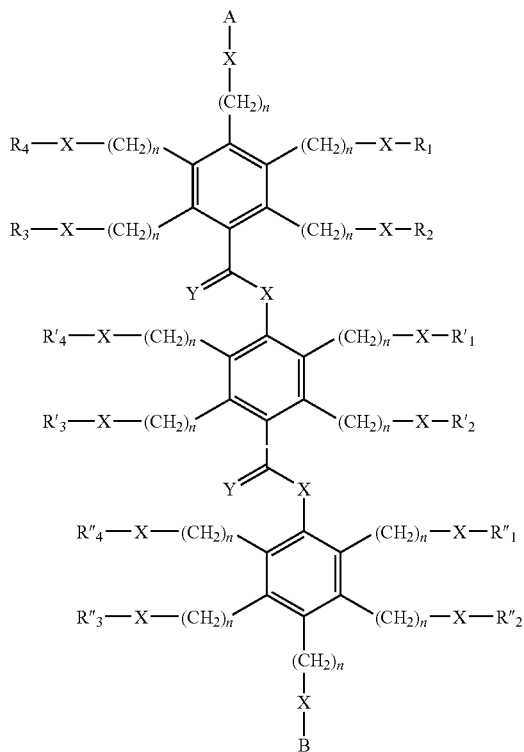

wherein X is independently a C, a N, a O, a S, a H, —CH₂CH₂—, —CH═CH—, —C≡C—, —NH—, —NR—, —NH—NH—, —NH(CH₂)ₙNH, —NR(CH₂)ₙNR'— NR—NR'—, —NH—O—, —NR—O—, —NH(CH₂)O—, NR(CH₂)ₙO—, —NH(CH₂)ₙS—, —NR(CH₂)ₙS—, —O(CH₂)ₙO—, —O(CH₂)ₙS—, —S(CH₂)ₙS—, —CO—, —CO₂—, —COS—, —CONH—, —CONR—, —OC(O)NH—, —NHCONH—, —CONHCO—, —CO(CH₂)ₙCO—, or combination thereof, wherein Y is independently a N, a O, a S or 2Hs; wherein R1, R2, R3, R4, R'1, R'2, R'3, R'4, R"1, R"2, R'3, and R"4, comprise independently a H, optionally substituted alkyl, lower alkyl, alkoxy, alkoxyalkyl, hydroxy, hydroxyalkyl, alkenyl, amino, imino, nitrate, alkylamino, dialkylamino, nitro, nitroso, aryl, biaryl, polycyclic aromatic, alkylaryl, arylalkyl, arylalkoxy, arylalkylamino, cycloalkyl, bridged cycloalkyl, cycloalkoxy, cycloalkylalkyl, arylthio, alkylthio, alkylsulfinyl, alkylsulfonyl, arylsulfonyl, arylsulfinyl, carboxamido, carbamoyl, carboxyl, carbonyl, alkoxycarbonyl, halogen, haloalkyl, haloalkoxy, heteroaryl, heterocyclic ring, arylheterocyclic ring, heterocyclic compounds, amido, imido, guanidino, hydrazido, aminoxy, alkoxyamino, alkylamido, urea, carboxylic ester, thioethers, carboxylic acids, phosphoryl groups, polycyclic aromatic substituted with a OH, NH₂, SH, F, Cl, Br, I, NHR, NRR', CN₃H₄, a N, a O, a S, a H, or combination thereof. And, n is 0, 1, 2, 3, 4, 5, 6, 7 etc. For example R1, R2, R3, R4, R'1, R'2, R'3, R'4, R"1, R"2, R"3, and R"4, may include independently one or more of the structures listed in FIG. 13, where Z is a OH, NH₂, SH, F, Cl, Br or I; W is a OH, OR, NH₂, NHR, NRR' or CN₃H₄; n is 0, 1, 2, 3, 4, 5, 6, 7 etc.; and Y is a N, a O, a S or 2Hs.

"A" may be a substituent (R1, R2, R3, R4, R'1, R'2, R'3, R'4, R"1, R"2, R"3, or R"4), an acetyl, Boc (t-butoxycarbonyl), a Fmoc (9-fluorenylmethoxycarbonyl), a Cbz (benzyloxycarbonyl), an Aloc (allyloxycarbonyl), an amino acid, an amino acid analogue, an artificial amino acid, a dipeptide, a tripeptide, a tetrapeptide, or a pentapeptide. "A" may be a peptide sequence of between 2 and 30 amino acids that has greater than 50% homology to a portion of the GLP-1 sequence SEQ. ID.: 1. FIG. 14 is the sequence of GLP-1 from amino acid 7 to amino acid 36. "A" may be a linker of 1-20 amino acids, an optionally substituted lower alkyl, an optionally substituted C1-C7 alkyl, a linker as listed below:

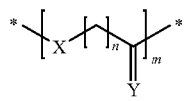

or a combination thereof.

"B" may be a substituent (R1, R2, R3, R4, R'1, R'2, R'3, R'4, R"1, R'2, R"3, or R"4), an optionally substituted alkyl, lower alkyl, an optionally substituted C1-C7 alkyl, an amino acid, an amino acid analogue, an artificial amino acid, a dipeptide, a tripeptide, a tetrapeptide, or a pentapeptide; a peptide sequence of between 2 and 30 amino acids that has greater than 50% homology to a portion of the GLP-1 sequence SEQ. ID.:1 (FIG. 14); a linker of 1-20 amino acids, an optionally substituted C1-C7 alkyl or a linker as listed below:

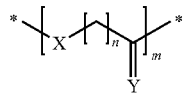

or a combination thereof, which may be optionally connected to one or more of the compounds M1-M12 listed in FIG. 15, or 19A of FIG. 19; or a combinations thereof.

FIGS. 16A-16K are images that illustrate various α-helix mimetic compounds of the present invention. FIGS. 16A-16C provide general structures indicating examples of the modification to the bonds that link the individual benzamides. FIGS. 16D-16K are images that illustrate various α-helix mimetic compounds of the present invention. This provides the basic structure indicating examples of the locations on the rings that may be substituted with various groups to provide different characteristics. In addition, R may individually be substituted with various groups to provide different characteristics, e.g., optionally substituted alkyl, lower alkyl, C1-C7 alkyl, alkoxy groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, carboxamido groups, carbamoyl groups, urea groups, carboxyl groups, carbonyl groups, alkoxycarbonyl groups, halogen groups, haloalkyl groups, haloalkoxy groups, heteroaryl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or a combination thereof. For example, R may include independently one or more of the structures listed in FIG. 13, where Z is a OH, NH$_2$, SH, F, Cl, Br or I; W is a OH, OR, NH$_2$, NHR, NRR' or CN$_3$H$_4$; n is 0, 1, 2, 3, 4, 5, 6, 7 etc.; and Y is a N, a O, a S or 2Hs.

Figure 17A:
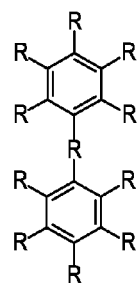
FIGS. 17A-17M are structures of another subset of the α-helix peptidomimetics compounds described in the current invention.
Figure 17B:
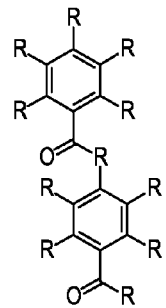
Figure 17C:
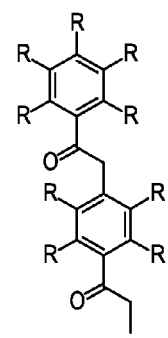
Figure 17D:
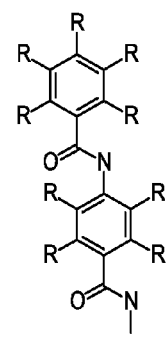
Figure 17E:
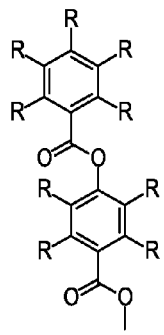
Figure 17F:
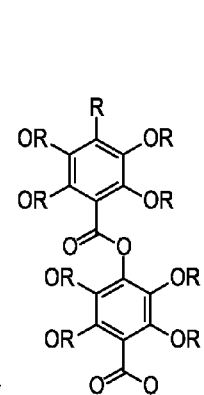
Figures 17G, 17H:
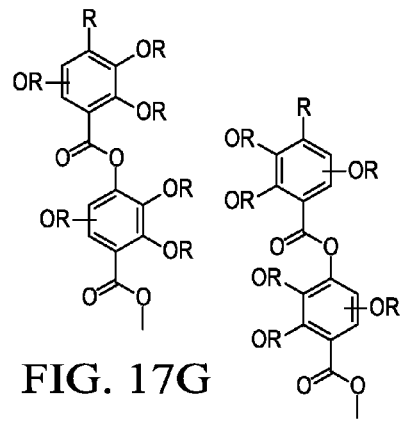
Figure 17I:
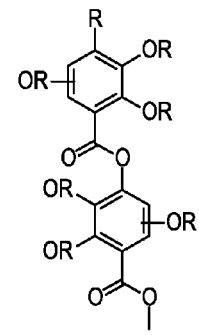
Figure 17J:
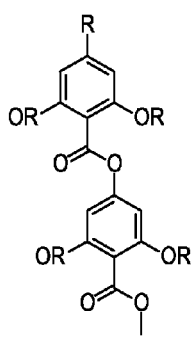
Figure 17K:
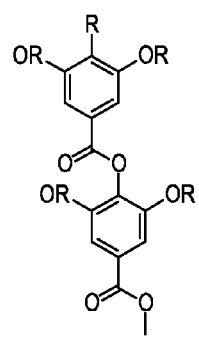
Figure 17L:
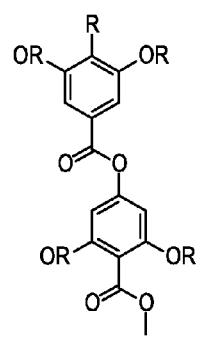
Figure 17M:
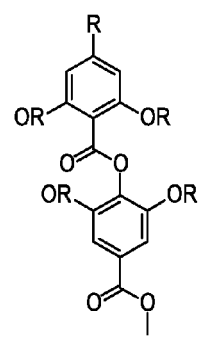

FIGS. 17A-17M are images that illustrate various α-helix mimetic compounds of the present invention. FIGS. 17A-17B provide the general structures indicating examples of the modification to the bonds that link the 2 individual benzamides. FIGS. 17C-17E provide specific examples of the general structure of the modification to the bonds that link the individual benzamides. FIGS. 17F-17M are images that illustrate various α-helix mimetic compounds of the present invention. This provides the basic structure indicating examples of the locations on the rings that may be substituted with various groups to provide different characteristics. In addition, R may individually be substituted with various groups to provide different characteristics, e.g., R may be optionally substituted alkyl, lower alkyl, C1-C7 alkyl, alkoxy groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, carboxamido groups, carbamoyl groups, carboxyl groups, carbonyl groups, alkoxycarbonyl groups, urea groups, halogen groups, haloalkyl groups, haloalkoxy groups, heteroaryl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof. For example, R may include independently one or more of the structures listed in FIG. 13, where Z is a OH, NH$_2$, SH, F, Cl, Br or I; W is a OH, OR, NH$_2$, NHR, NRR' or CN$_3$H$_4$; n is 0, 1, 2, 3, 4, 5, 6, 7 and so forth; and Y is a N, a O, a S or 2Hs.

FIGS. 18A-18K provide specific examples of the structure of the various individual α-helix mimetic compounds of the present invention. FIGS. 18A-18K provide the general structure of the compound with the R group positions indicated. The table lists the compound numbers 100-960 and indicates the functional groups at each R group on the general structure of the α-helix mimetic compound to provide different characteristics.

FIGS. 19A-19E are images that illustrate various α-helix mimetic compounds of the present invention. FIG. 19A provides the general structure of the α-helix mimetic compounds. X may independently be a C, a N, a O, a S, a H, —CH$_2$CH$_2$—, —CH═CH—, —C≡C—, —NH—, —NR—, —NH—NH—, —NH(CH$_2$)$_n$NH, —NR(CH$_2$)$_n$NR'— —NR—NR'—, —NH—O—, —NR—O—, —NH(CH$_2$)$_n$O—, —NR(CH$_2$)$_n$O—, —NH(CH$_2$)$_n$S—, —NR(CH$_2$)$_n$S—, —O(CH$_2$)$_n$O—, —O(CH$_2$)$_n$S—, —S(CH$_2$)$_n$S—, —CO—, —CO$_2$—, —COS—, —CONH—, —CONR—, —OC(O)NH—, —NHCONH—, —CONHCO—, —CO(CH$_2$)$_n$CO—, or combination thereof, and Y may be independently a N, a O, a S or 2H's. And, n is 0, 1, 2, 3, 4, 5, 6, 7 etc. R1, R2, R3, R4, R'1, R'2, R'3, R'4, R"1, R"2, R"3, and R"4, comprise independently a H, optionally substituted alkyl, lower alkyl, alkoxy, alkoxyalkyl, hydroxy, hydroxyalkyl, alkenyl, amino, imino, nitrate, alkylamino, dialkylamino, nitro, nitroso, aryl, biaryl, polycyclic aromatic, alkylaryl, arylalkyl, arylalkoxy, arylalkylamino, cycloalkyl, bridged cycloalkyl, cycloalkoxy, cycloalkyl-alkyl, arylthio, alkylthio, alkylsulfinyl, alkylsulfonyl, arylsulfonyl, arylsulfinyl, carboxamido, carbamoyl, carboxyl, carbonyl, alkoxycarbonyl, halogen, haloalkyl, haloalkoxy, heteroaryl, heterocyclic ring, arylheterocyclic ring, heterocyclic compounds, amido, imido, guanidino, hydrazido, aminoxy, alkoxyamino, alkylamido, urea, carboxylic ester, thioethers, carboxylic acids, phosphoryl groups, polycyclic aromatic substituted with a OH, NH$_2$, SH, F, Cl, Br, I, NHR, NRR', CN$_3$H$_4$, a N, a O, a S, a H, or combination thereof. FIGS. 19B-19E provide several specific examples of the general structure. The compositions of the present invention may be an agonist, an inverse agonist, an antagonist, a partial agonist, a partial antagonist, a co-agonist or a combination thereof depending on the receptor and the functional groups of the composition.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. U.K. Prospective Diabetes Study Group, United Kingdom prospective diabetes study 16, Overview of 6 years' therapy of type II diabetes: A progressive disease. Diabetes 1995, 44, 1249-1258.
2. Zhang, B. B.; Moller, D. E., New approaches in the treatment of type 2 diabetes. Curr. Opin. Chem. Biol. 2000, 4, 461-467.
3. Kahn, B. B., Type 2 diabetes: when insulin secretion fails to compensate for insulin resistance. Cell 1998, 92, 593-596.
4. Cavaghan, M. K.; Ehrmann, D. A.; Polonsky, K. S., Interactions between insulin resistance and insulin secretion in the development of glucose intolerance. J. Clin. Invest. 2000, 106, 329-333.
5. Mojsov, S.; Heinrich, G.; Wilson, I. B.; Ravazzola, M.; Orci, L.; Habener, J. F., Preproglucagon gene expression in pancreas and intestine diversifies at the level of post-translational processing. J. Biol. Chem. 1986, 261, 11880-11889.
6. Nauck, M. A.; Kleine, N.; Orskov, C.; Holst, J. J.; Willms, B.; Creuzfeldt, W., Normalization of fasting hyperglycemia by exogenous glucagon-like peptide-1 (7-36 amide) in type-2 (non-insulindependent) diabetic patients. Diabetologia 1993, 36, 741-744.
7. Bell, G. I.; Sanchez-Pescadore, R.; Layboum, P. L.; Najarian, R. C., Exon duplication and divergence in the human preproglucagon gene. Nature 1983, 304, 368-371.
8. Kieffer, T. J.; Habener, J. F., The glucagon-like peptides. Endocr. Rev. 1999, 20, 876-913.
9. Gutniak, M.; Orskov, C.; Holst, J. J.; Ahren, B.; Efendc, S., Antidiabetogenic effect of glucagon-like peptide-1 (7-36) amide in normal subjects and patients with diabetes mellitus. N. Engl. J. Med. 1992, 326, 1316-1322.
10. Thorens, B., Expression cloning of the pancreatic beta cell receptor for the gluco-incretin hormone glucagon-like peptide 1. Proc. Natl. Acad. Sci. U.S.A. 1992, 89, 8641-8645.
11. Holst, J. J.; Orskov, C.; Knuhtsen, S.; Baldissera, F. A. G.; Poulsen, S. S.; Nielsen, O. V., Truncated glucagon-like peptide I, an insulin-releasing hormone from the distal gut. FEBS Lett. 1987, 211, 169-174.
12. Mojsov, S.; Weir, C. G.; Habener, J. F., Insulinotropin: glucagon-like peptide I (7-37) co-encoded in the glucagon gene is a potent stimulator of insulin release in the perfused rat pancreas. J. Clin. Invest. 1987, 79, 616-619.
13. Kreymann, B.; Ghatei, M. A.; Williams, G.; Bloom, S. R., Glucagon-like peptide-17-36: a physiological incretin in man. Lancet 1987, 2, 1300-1303.
14. Drucker, D. J.; Philippe, J.; Mosjov, S.; Chick, W. L.; Habener, J. F., Glucagon-like peptide I stimulates insulin gene expression and increases cyclic AMP levels in a rat islet cell line. Proc. Natl. Acad. Sci. U.S.A. 1987, 84, 3434-3438.
15. Holz, G. G.; Kuhtreiber, W. M.; Habener, J. F., Pancreatic beta-cells are rendered glucosecompetent by the insulinotropic hormone glucagon-like peptide-1 (7-37). Nature 1993, 361, 362-365.
16. Bulotta, A.; Hui, H.; Anastasi, E.; Bertolotto, C.; Boros, L. G.; Di Mario, U.; Perfetti, R., Cultured pancreatic ductal cells undergo cell cycle re-distribution and beta-cell-like differentiation in response to glucagon-like peptide-1. J. Mol. Endocrinol. 2002, 29, 347-360.
17. Egan, J. M.; Bulotta, A.; Hui, H.; Perfetti, R., GLP-1 receptor agonists are growth and differentiation factors for pancreatic islet beta cells. Diabetes/Metab. Res. Rev. 2003, 19, 115-123.
18. Stoffers, D. A.; Kieffer, T. J.; Hussain, M. A.; Drucker, D. J.; Bonner-Weir, S.; Habener, J. F.; Egan, J. M., Insulinotropic glucagon-like peptide 1 agonists stimulate expression of homeodomain protein IDX-1 and increase islet size in mouse pancreas, Diabetes 2000, 49, 741-748.
19. Unger, R. H., Role of glucagon in the pathogenesis of diabetes: the status of the controversy. Metabolism 1978, 27, 1691-1709.
20. Ørskov, C.; Holst, J. J.; Neilsen, O. V., Effect of truncated glucagon-like peptide-1 [proglucagon(78-107) amide] on endocrine secretion from pig pancreas, antrum, and nonantral stomach. Endocrinology 1988, 123, 2009-2013.
21. Wettergren, A.; Schjoldager, B.; Mortensen, P. E.; Myhre, J.; Christiansen, J.; Holst, J. J., Truncated GLP-1 (proglucagon 78-107-amide) inhibits gastric and pancreatic functions in man. Dig. Dis. Sci. 1993, 38, 665-673.
22. Flint, A.; Raben, A.; Astrup, A.; Holst, J. J., Glucagon-like peptide 1 promotes satiety and suppresses energy intake in humans. J. Clin. Invest. 1998, 101, 515-520.
23. Zander, M.; Madsbad, S.; Madsen, J. L.; Holst, J. J., Effect of 6-week course of glucagon-like peptide 1 on glycaemic control, insulin sensitivity, and beta-cell function in type 2 diabetes: a parallel-group study. Lancet 2002, 359, 824-830.
24. Knudsen, L. B., Glucagon-like peptide-1: the basis of a new class of treatment for type 2 diabetes. J. Med. Chem. 2004, 47, 4128-4134.
25. Toft-Nielsen, M. B.; Madsbad, S.; Holst, J. J., Determinants of the effectiveness of glucagon-like peptide-1 in type 2 diabetes. J. Clin. Endocrinol. Metab. 2001, 86, 3853-3860.
26. Vilsboll, T.; Krarup, T.; Madsbad, S.; Holst, J. J., No reactive hypoglycemia in type 2 diabetic patients after subcutaneous administration of GLP-1 and intravenous glucose. Diabetic Med. 2001, 18, 144-149.
27. Eng, J.; Kleinman, W. A.; Singh, L.; Singh, G.; Raufman, J. P., Isolation and characterization of exendin-4, an exendin-3 analogue, from Heloderma suspectum venom. Further evidence for an exendin receptor on dispersed acini from guinea pig pancreas. J. Biol. Chem. 1992, 267, 7402-7405.
28. Göke, R.; Fehmann, H. C.; Linn, T.; Schmidt, H.; Krause, M.; Eng, J.; Göke, B., Exendin-4 is a high potency agonist and truncated exendin-(9-39)-amide an antagonist at the glucagon-like peptide 1-(7-36)-amide receptor of insulin-secreting beta-cells. J. Biol. Chem. 1993, 268, 19650-19655.
29. Young, A. A.; Gedulin, B. R.; Bhavsar, S.; Bodkin, N.; Jodka, C.; Hansen, B.; Denaro, M., Glucose-lowering and insulin-sensitizing actions of exendin-4. Diabetes 1999, 48, 1026-1034.

30. Edwards, C. M. B.; Stanley, S. A.; Davis, R.; Brynes, A. E.; Frost, G. S.; Seal, L. J.; Ghatei, M. A.; Bloom, S. R., Exendin-4 reduces fasting and postprandial glucose and decreases energy intake in healthy volunteers. Am. J. Physiol. Endocrinol. Metab. 2001, 281, E155-E161.
31. DeFronzo, R. A.; Ratner, R. E.; Han, J.; Kim, D. D.; Fineman, M. S.; Baron, A. D., Effects of exenatide (exendin-4) on glycemic control and weight over 30 weeks in metformin-treated patients with type 2 diabetes. Diabetes Care 2005, 28, 1092-1100.
32. Elbronds, B.; Jakobsen, G.; Larsen, S.; Agerso, H.; Jensen, L. B.; Rolan, P.; Sturis, J.; Hatorp, V.; Zdravkovic, M., Pharmacokinetics, pharmacodynamics, safety, and tolerability of a single-dose of NN2211, a long-acting glucagon-like peptide 1 derivative, in healthy male subjects. Diabetes Care 2002, 25, 1398-1404.
33. Deacon, C. F.; Johnsen, A. H.; Holst, J. J., Degradation of glucagon-like peptide-1 by human plasma in vitro yields an N-terminally truncated peptide that is a major endogenous metabolite in vivo. J. Clin. Endocrinol. Metab. 1995, 80, 952-957.
34. Kieffer, T. J.; McIntosh, C. H. S.; Pederson, R. A., Degradation of GIP and truncated GLP-1 in vitro and in vivo by dipeptidyl peptidase IV. Endocrinology 1995, 136, 3585-3596.
35. Perry, T. A.; Greig, N. H., The glucagon-like peptides: a double-edged therapeutic sword? Trends Pharmacol. Sci. 2003, 24, 377-383.
36. Knudsen, L. B.; Pridal, L., GLP-1(9-36) amide is major metabolite of GLP-1(7-36) amide after in vivo administration to dogs, and it acts as an antagonist on the pancreatic receptor. Eur. J. Pharmacol. 1996, 318, 429-435.
37. Drucker, D. J.; Nauck, M. A., The incretin system: glucagon-like peptide-1 receptor agonists and dipeptidyl peptidase-4 inhibitors in type 2 diabetes. Lancet 2006, 368, 1696-1705.
38. Murphy, K. G.; Bloom, S. R., Nonpeptidic glucagon-like peptide 1 receptor agonists: A magic bullet for diabetes? Proc. Natl. Acad. Sci. U.S.A. 2007, 104, 689-690.
39. Pauletti, G. M.; Gangwar, S.; Siahaan, T. J.; Aubé, J.; Borchardt, R. T., Improvement of oral peptide bioavailability: Peptidomimetics and prodrug strategies. Adv. Drug Delivery Rev. 1997, 27, (235-256).
40. Mahato, R. I.; Narang, A. S.; Thoma, L.; Miller, D. D., Emerging trends in oral delivery of peptide and protein drugs. Critical Reviews in Therapeutic Drug Carrier Systems 2003, 20, 153-214.
41. Kolterman, O. G.; Buse, J. B.; Fineman, M. S.; Gaines, E.; Heintz, S.; Bicsak, T. A.; Taylor, K.; Kim, D.; Aisporna, M.; Wang, Y.; Baron, A. D., Synthetic exendin-4 (exenatide) significantly reduces postprandial and fasting plasma glucose in subjects with type 2 diabetes. J. Clin. Endocrinol. Metab. 2003, 88, 3082-3089.
42. Collins, J. L.; Dambek, P. J.; Goldstein, S. W.; Faraci, W. S., CP-99, 711: A non-peptide glucagon receptor antagonist. Bioorg. Med. Chem. Lett. 1992, 2, 915-918.
43. Madsen, P.; Knudsen, L. B.; Wiberg, F. C.; Carr, R. D., Discovery and structure-activity relationship of the first non-peptide competitive human glucagon receptor antagonists. J. Med. Chem. 1998, 41, 5150-5157.
44. Cascieri, M. A.; Koch, G. E.; Ber, E.; Sandowski, S. J.; Louizides, D.; de Laszlo, S. E.; Hacker, C.; Hagmann, W. K.; MacCoss, M.; Chicchi, G. G.; Vicario, P. P., Characterization of a novel, nonpeptidyl antagonist of the human glucagon receptor. J. Biol. Chem. 1999, 271, 8694-8697.
45. Chang, L. L.; Sidler, K. L.; Cascieri, M. A.; De Laszlo, S. E.; Koch, G.; Li, B.; MacCoss, M.; Mantlo, N.; O'Keefe, S.; Pang, M.; Rolando, A.; Hagmann, W. K., Substituted imidazoles as glucagon receptor antagonists. Bioorg. Med. Chem. Lett. 2001, 11, 2549-2553.
46. Ling, A.; Hong, Y.; Gonzalez, J.; Gregor, V.; Polinsky, A.; Kuki, A.; Shi, S.; Teston, K.; Murphy, D.; Porter, J.; Kiel, D.; Lakis, J.; Anderes, K.; May, J., Identification of alkylidene hydrazides as glucagon receptor antagonists. J. Med. Chem. 2001, 44, 3141-3149.
47. Tibaduiza, E. C.; Chen, C.; Beinborn, M., A small molecule ligand of the glucagon-like peptide 1 receptor targets its amino-terminal hormone binding domain. J. Biol. Chem. 2001, 276, 37787-37793.
48. Madsen, P.; Ling, A.; Plewe, M.; Sams, C. K.; Knudsen, L. B.; Sidelmann, U. G.; Ynddal, L.; Brand, C. L.; Andersen, B.; Murphy, D.; Teng, M.; Truesdale, L.; Kiel, D.; May, J.; Kuki, A.; Shi, S.; Johnson, M. D.; Teston, K. A.; Feng, J.; Lakis, J.; Anderes, K.; Gregor, V.; Lau, J., Optimization of alkylidene hydrazide based human glucagon receptor antagonists. Discovery of the highly potent and orally available 3-cyano-4-hydroxybenzoic acid [1-(2,3,5,6-tetramethylbenzyl)-1H-indol-4-ylmethylene]hydrazide. J. Med. Chem. 2002, 45, 5755-5775.
49. Hoare, S. R. J., Mechanisms of peptide and nonpeptide ligand binding to class B G-proteincoupled receptors. Drug Discovery Today 2005, 10, 417-427.
50. Knudsen, L. B.; Kiel, D.; Teng, M.; Behrens, C.; Bhumralkar, D.; Kodra, J. T.; Holst, J. J.; Jeppesen, C. B.; Johnson, M. D.; de Jong, J. C.; Jorgensen, A. S.; Kercher, T.; Kostrowicki, J.; Madsen, P.; Olesen, P. H.; Petersen, J. S.; Poulsen, F.; Sidelmann, U. G.; Sturis, J.; Truesdale, L.; May, J.; Lau, J., Small-molecule agonists for the glucagon-like peptide 1 receptor. Proc. Natl. Acad. Sci. U.S.A. 2007, 104, 937-942.
51. Chen, D.; Liao, J.; Li, N.; Zhou, C.; Liu, Q.; Wang, G.; Zhang, R.; Zhang, S.; Lin, L.; Chen, K.; Xie, X.; Nan, F.; Young, A. A.; Wang, M.-W., A nonpeptidic agonist of glucagon-like peptide 1 receptors with efficacy in diabetic db/db mice. Proc. Natl. Acad. Sci. U.S.A. 2007, 104, 943-948.
52. Marshall, G. R., A hierarchical approach to peptidomimetic design. Tetrahedron 1993, 49, 3547-3558.
53. Ahn, J.-M.; Boyle, N. A.; MacDonald, M. T.; Janda, K. D., Peptidomimetics and peptide backbone modifications. Mini-Reviews in Medicinal Chemistry 2002, 2, 463-473.
54. Olson, G. L.; Bolin, D. R.; Bonner, M. P.; Bös, M.; Cook, C. M.; Fry, D. C.; Graves, B. J.; Hatada, M.; Hill, D. E.; Kahn, M.; Madison, V. S.; Rusiecki, V. K.; Sarabu, R.; Sepinwall, J.; Vincent, G. P.; Voss, M. E., Concepts and progress in the development of peptide mimetics. J. Med. Chem. 1993, 36, 3039-3049.
55. Gante, J., Peptidomimetics—tailored enzyme inhibitors. Angew. Chem. Int. Ed. 1994, 33, 1699-1720.
56. Hirschmann, R.; Nicolaou, K. C.; Pietranico, S.; Salvino, J.; Leahy, E. M.; Sprengeler, P. A.; Furst, G.; Smith, A. B.; Strader, C. D.; Cascieri, M. A.; Candelore, M. R.; Donaldson, C.; Vale, W.; Maechler, L., Nonpeptidal peptidomimetics with β-D-glucose scaffolding. A partial somatostatin agonist bearing a close structural relationship to a potent, selective substance P antagonist. J. Am. Chem. Soc. 1992, 114, 9217-9218.
57. Hirschmann, R.; Nicolaou, K. C.; Pietranico, S.; Leahy, E. M.; Salvino, J.; Arison, B.; Cichy, M. A.; Spoors, P. G.; Shakespeare, W. C.; Sprengeler, P. A.; Hamley, P.; Smith, A. B.; Reisine, T.; Raynor, K.; Maechler, L.; Donaldson, C.; Vale, W.; Freidinger, R. M.; Cascieri, M. R.; Strader, C. D., De novo design and synthesis of somatostatin non- 57. peptide peptidomimetics utilizing β-D-glucose as a novel scaffolding. J. Am. Chem. Soc. 1993, 115, 12550-12568.
58. Hruby, V. J., Design in topographical space of peptide and peptidomimetic ligands that affect behavior a chemist's glimpse at the mind-body problem. Acc. Chem. Res. 2001, 34, 389-397.
59. Peczuh, M. W.; Hamilton, A. D., Peptide and protein recognition by designed molecules. Chem. Rev. 2000, 100, 2479-2494.
60. Segre, G. V.; Goldring, S. R., Receptors for secretin, calcitonin, parathyroid hormone (PTH)/PTH related peptide, vasoactive intestinal peptide, glucagonlike peptide 1, growth hormone-releasing hormone, and glucagon belong to a newly discovered G-protein-linked receptor family. Trends in Endocrinology and Metabolism 1993, 4, 309-314.
61. Konig, W., Peptides and protein hormones. Pharmaceuticals 2000, 3, 1339-1492.
62. Ahn, J.-M.; Medeiros, M.; Trivedi, D.; Hruby, V. J., Development of potent truncated glucagon antagonists. J. Med. Chem. 2001, 44, 1372-1379.
63. Runge, S.; Wulff, B. S.; Madsen, K.; Bräuner-Osborne, H.; Knudsen, L. B., Different domains of the glucagon and glucagon-like peptide-1 receptors provide the critical determinants of ligand selectivity. Br. J. Pharmacol. 2003, 138, 787-794.
64. Ahn, J.-M.; Gitu, P. M.; Medeiros, M.; Swift, J.; Trivedi, D.; Hruby, V. J., A new approach to search for the bioactive conformation of glucagon: positional cyclization scanning. J. Med. Chem. 2001, 44, 3109-3116.
65. Thornton, K.; Gorenstein, D. G., Structure of glucagon-like peptide (7-36) amide in a dodecylphosphocholine micelle as determined by 2D NMR. Biochemistry 1994, 33, 3532-3539.
66. Neidigh, J. W.; Fesinmeyer, R. M.; Prickett, K. S.; Andersen, N. H., Exendin-4 and glucagon-like peptide-1: NMR structural comparisons in the solution and micelle-associated states. Biochemistry 2001, 40, 13188-13200.
67. Rizo, J.; Gierasch, L. M., Constrained peptides: models of bioactive peptides and protein substructures. Annu. Rev. Biochem. 1992, 61, 387-418.
68. Widmer, H.; Widmer, A.; Braun, W., Extensive distance geometry calculations with different NOE calibrations: new criteria for structure selection applied to sandostatin and BPTI. J. Biomol. NMR 1993, 3, 307-324.
69. Marqusee, S.; Baldwin, R. L., Helix stabilization by Glu- . . . Lys+ salt bridges in short peptides of de novo design. Proc. Natl. Acad. Sci. U.S.A. 1987, 84, 8898-8902.
70. Ösapay, G.; Taylor, J. W., Multicyclic polypeptide model compounds. 1. Synthesis of a tricyclic amphiphilic α-helical peptide using an oxime resin, segment-condensation approach. J. Am. Chem. Soc. 1990, 112, 6046-6051.
71. Bogan, A. A.; Thorn, K. S., Anatomy of hot spots in protein interfaces. J. Mol. Biol. 1998, 280, 1-9.
72. Burgess, K., Solid-phase syntheses of β-turn analogues to mimic or disrupt protein-protein interactions. Acc. Chem. Res. 2001, 34, 826-835.
73. Souers, A. J.; Ellman, J. A., β-Turn mimetic library synthesis: scaffolds and applications. Tetrahedron 2001, 57, 7431-7448.
74. Figuera, N. D. L.; Martin-Martinez, M.; Herranz, R.; García-López, M. T.; Latorre, M.; Cenarruzabeitia, E.; Río, J. D.; González-Muñiz, R., Highly constrained dipeptoid analogues containing a type II' b-turn mimic as novel and selective CCK-A receptor ligands. Bioorg. Med. Chem. Lett. 1999, 9, 43-48.
75. Horwell, D. C.; Howson, W.; Ratcliffe, G. S.; Willems, H. M., The design of dipeptide helical mimetics: the synthesis, tachykinin receptor affinity and conformational analysis of 1,1,6-trisubstituted indanes. Bioorg. Med. Chem. 1996, 4, 33-42.
76. Jacoby, E., Biphenyls as potential mimetics of protein α-helix. Bioorg. Med. Chem. Lett. 2002, 12, 891-893.
77. Orner, B. P.; Ernst, J. T.; Hamilton, A. D., Toward proteomimetics: Terphenyl derivatives as structural and functional mimics of extended regions of an α-helix. J. Am. Chem. Soc. 2001, 123, 5382-5383.
78. Ernst, J. T.; Becerril, J.; Park, H. S.; Yin, H.; Hamilton, A. D., Design and application of an α-helixmimetic scaffold based on an oligoamide-foldamer strategy: antagonism of the Bak BH3/Bcl-xL complex. Angew. Chem. Int. Ed. 2003, 42, 535-539.
79. Oguri, H.; Oomura, A.; Tanabe, S.; Hirama, M., Design and synthesis of a trans-fused polycyclic ether skeleton as an α-helix mimetic scaffold. Tetrahedron Lett. 2005, 46, 2179-2183.
80. Mohamadi, F.; Richards, N. G. J.; Guida, W. C.; Liskamp, R.; Lipton, M.; Caufield, C.; Chang, G.; Hendrickson, T.; Still, W. C., MacroModel—An integrated software system for modeling organic and bioorganic molecules using molecular mechanics. J. Comput. Chem. 1990, 11, 440-467.
81. Allinger, N. L.; Yuh, Y. H.; Lii, J.-H., Molecular mechanics. The MM3 force field for hydrocarbones. 1. J. Am. Chem. Soc. 1989, 111, 8551-8565.
82. Ahn, J.-M.; Han, S.-Y., Facile synthesis of benzamides to mimic an α-helix. Tetrahedron Lett. Accepted.
83. Rickard, D. J.; Wang, F.-L.; Rodriguez-Rojas, A.-M.; Wu, Z.; Trice, W. J.; Hoffman, S. J.; Votta, B.; Stroup, G. B.; Kumar, S.; Nuttall, M. E., Intermittent treatment with parathyroid hormone (PTH) as well as a non-peptide small molecule agonist of the PTH1 receptor inhibits adipocyte differentiation in human bone marrow stromal cells. Bone 2006, 39, 1361-1372.
84. Chapuis, H.; Strazewski, P., Shorter puromycin analog synthesis by means of an efficient Staudinger-Vilarrasa coupling. Tetrahedron 2006, 62, 12108-12115.
85. Adelhorst, K.; Hedegaard, B. B.; Knudsen, L. B.; Kirk, O., Structure-activity studies of glucagonlike peptide-1. J. Biol. Chem. 1994, 269, 6275-6278.

What is claimed is:

1. A tris-benzamide peptidomimetic that binds to a glucagon-like peptide 1 receptor consisting of the formula:

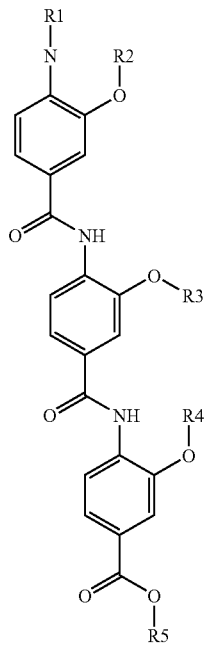

wherein i) R1 is acetyl, R2 is benzyl, R3 and R4 are 4-fluorobenzyl, and R5 is GLP-1 (22-36) amide;

ii) R1 is t-butoxycarbonyl, R2 is methyl, R3 is benzyl, R4 is 2-naphthylmethyl and R5 is GLP-1 (22-36) amide;

iii) R1 is the dipeptide His-Gly, R2 is benzyl, R3 is isopropyl, R4 is 4-fluorobenzyl group and R5 is GLP-1 (22-36) amide; or iv) R1 is histidine, R2 is benzyl, R3 is isopropyl, R4 is 4-fluorobenzyl and R5 is GLP-1 (22-36) amide.

2. The tris-benzamide peptidomimetic composition of claim 1, wherein R1 is t-butoxycarbonyl, R2 is methyl, R3 is benzyl, R4 is 2 naphthylmethyl, and R5 is GLP-1 (22-36) amide.

3. The tris-benzamide peptidomimetic of claim 1, wherein R1 is the dipeptide His-Gly, R2 is benzyl, R3 is isopropyl, R4 is 4-fluorobenzyl group and R5 is GLP-1 (22-36) amide.

4. The tris-benzamide peptidomimetic of claim 1, wherein R1 is histidine, R2 is benzyl, R3 is isopropyl, R4 is 4-fluorobenzyl, and R5 is GLP-1 (22-36) amide.

5. The tris-benzamide peptidomimetic of claim 1, wherein R1 is acetyl, R2 is benzyl, R3 and R4 are 4-fluorobenzyl and R5 is GLP-1 (22-36) amide.

6. A pharmaceutical composition comprising the tris-benzamide peptidomimetic of claim 1 and one or more pharmaceutically acceptable carriers.

* * * * *

UNITED STATES PATENT AND TRADEMARK OFFICE
CERTIFICATE OF CORRECTION

| | | |
|---|---|---|
| PATENT NO. | : 7,816,324 B2 | Page 1 of 1 |
| APPLICATION NO. | : 12/048199 | |
| DATED | : October 19, 2010 | |
| INVENTOR(S) | : Ahn et al. | |

It is certified that error appears in the above-identified patent and that said Letters Patent is hereby corrected as shown below:

Title Page, item [73] Assignee - Add

New England Medical Center Hospitals, Inc.
750 Washington Street
Boston, Massachusetts 02111

Signed and Sealed this
Third Day of May, 2011

David J. Kappos
*Director of the United States Patent and Trademark Office*